(12) United States Patent
Erstling et al.

(10) Patent No.: US 12,188,939 B2
(45) Date of Patent: Jan. 7, 2025

(54) SUPER-RESOLUTION OPTICAL MICROSCOPY USING ALUMINOSILICATE NANOPARTICLES

(71) Applicant: CORNELL UNIVERSITY, Ithaca, NY (US)

(72) Inventors: Jacob Erstling, Ithaca, NY (US); Joshua A. Hinckley, Framingham, MA (US); Nirmalya Bag, Ithaca, NY (US); Ulrich B. Wiesner, Ithaca, NY (US)

(73) Assignee: Cornell University, Ithaca, NY (US)

( * ) Notice: Subject to any disclaimer, the term of this patent is extended or adjusted under 35 U.S.C. 154(b) by 387 days.

(21) Appl. No.: 17/501,854

(22) Filed: Oct. 14, 2021

(65) Prior Publication Data
US 2022/0113315 A1 Apr. 14, 2022

Related U.S. Application Data

(60) Provisional application No. 63/091,796, filed on Oct. 14, 2020.

(51) Int. Cl.
G01N 33/58 (2006.01)
A61K 49/00 (2006.01)
G01N 21/64 (2006.01)

(52) U.S. Cl.
CPC ......... *G01N 33/587* (2013.01); *A61K 49/005* (2013.01); *G01N 21/6428* (2013.01); *G01N 21/6458* (2013.01); *G01N 2021/6439* (2013.01)

(58) Field of Classification Search
CPC ............. G01N 33/587; G01N 21/6428; G01N 21/6458; G01N 21/6439; G01N 21/6408; A61K 49/005; G02B 21/367; G02B 21/16
See application file for complete search history.

(56) References Cited

FOREIGN PATENT DOCUMENTS

WO 2016/179260 A1 11/2016
WO WO 2018191316 * 10/2018

* cited by examiner

Primary Examiner — Zohreh A Fay
(74) Attorney, Agent, or Firm — Hodgson Russ LLP; Paul Joseph Roman, Jr.

(57) ABSTRACT

Methods of obtaining and kits that can be used to obtain an optical super-resolution image of a sample or a portion thereof or an individual or a portion thereof. In various examples, the individual is an individual with cancer. In various examples, a method includes contacting a sample or individual with one or more aluminosilicate nanoparticle(s) that have at least one organic fluorophore molecule covalently bonded to the aluminosilicate network of the nanoparticle(s), or a composition including the aluminosilicate nanoparticle(s); irradiating the sample or the individual, thereby exciting at least one of the fluorophore molecules of an individual aluminosilicate nanoparticle; and obtaining a fluorescence image or a sequence of fluorescence images, which can be processed to obtain a super-resolution image of the sample or the individual. In various examples, the sample is a biological sample, living or fixed tissues and/or cells, or a biopsy obtained from an individual.

18 Claims, 49 Drawing Sheets

SUPER-RESOLUTION OPTICAL MICROSCOPY USING ALUMINOSILICATE NANOPARTICLES

CROSS-REFERENCE TO RELATED APPLICATIONS

This application claims the benefit of U.S. Provisional Patent Application No. 63/091,796 filed Oct. 14, 2020, the contents of which are hereby fully incorporated herein by reference in their entirety.

STATEMENT REGARDING FEDERALLY SPONSORED RESEARCH

This invention was made with government support under grant no. CA199081 awarded by the National Institutes of Health. The government has certain rights in the invention.

BACKGROUND OF THE DISCLOSURE

Single molecule localization based optical super-resolution microscopy (SRM) techniques, and in particular stochastic optical reconstruction microscopy (STORM), are powerful imaging tools to resolve structures below the diffraction limit of light, deepening our understanding of nanoscale interactions in chemical and biological systems. Imaging via STORM rests on stochastic blinking of organic fluorophores attached to their target structures such that only a subset of fluorophores is imaged with each frame of a time-lapse diffraction-limited fluorescence movie. Precise localizations of these sparsely emitting fluorophores in all frames are then reconstructed into a super-resolved STORM image. Optimal STORM probes include those with high brightness, high photostability, and low on-off duty cycle (ratio of "on" over "off" time) in cases of high labeling density, as localization precision is proportional to the square root of brightness and low duty cycle stable probes are less likely to have overlapping point spread functions (PSFs). In practice, dye blinking is conventionally achieved by exciting the fluorophores with two different light sources in a complex STORM imaging buffer cocktail, consisting of, e.g., thiol compound beta-mercaptoethanol (βME) and an oxygen scavenging (OS) system. The OS system is typically a combination of glucose, glucose oxidase, and oxygen catalase. Fluorophore blinking is caused by the formation of reversible long-lived dark states through dye interactions, e.g., with a primary thiol, which can be recovered to its ground state when aided by a UV light source. The typical imaging medium uses a non-neutral buffer and thiols that are toxic to many cell types, however, which limits the application of STORM in long-term live cell imaging. Moreover, the conventional requirement of two light sources/lasers for single-color STORM imaging puts an additional burden on the experiments and often poses technical challenges for non-experts. Nevertheless, STORM is considered an attractive SRM technique relative to other methods such as stimulated emission depletion (STED) as it does not require specialized microscopy systems and provides high resolving power.

Previous work on STORM systems has produced simpler and less toxic protocols, typically involving self-healing dyes as well as heavy-atom-containing quantum dots. Additionally, it has been shown that certain probes can be used for live-cell STORM, but only in specific organelles, such as the mitochondria, that have increased levels of thiol compound glutathione. An experimental strategy to induce blinking with only one excitation light source by using an imaging buffer that contains both oxidizing and reducing agents has been described. Through stochastic photo-induced oxidation and/or reduction of the fluorophore, it is forced into a radical cationic or radical anionic dark state. The fluorophore can then be recovered back to its ground state via another photo-induced redox interaction. While these and other methods are marked improvements upon the classic STORM setup, and some have enabled live cell super-resolution imaging, they still do not avert all of the complex light source and/or imaging buffer requirements as well as cytotoxicity issues that render live-cell imaging challenging.

SUMMARY OF THE DISCLOSURE

In an aspect, the present disclosure provides imaging methods. The imaging methods may be optical super-resolution imaging methods. The methods are based on use of aluminosilicate nanoparticles. This disclosure provides methods for imaging biological materials, such as, for example, cells (e.g., living cells, fixed cells, and the like), extracellular components, or tissues. In an example, a method of obtaining an image of a sample comprising a biological material comprises: contacting the sample (e.g., the individual) with one or more aluminosilicate nanoparticle(s) and/or one or more composition(s) of the present disclosure; irradiating the sample (e.g., individual or a portion thereof); and obtaining one or more (e.g., a plurality of) fluorescence image(s) of the sample (e.g., the individual or a portion thereof). The fluorescent image(s) may be used to generate an optical super-resolution image. In another example, a method for imaging of a region within an individual comprises (a) administering to the individual one or more aluminosilicate nanoparticle(s) and/or one or more composition(s) of the present disclosure; (b) irradiating the individual or a portion thereof with electromagnetic radiation (e.g., directing electromagnetic radiation, which may be referred to as, excitation light into the individual), thereby exciting at least one of the one or more dye molecule(s) of the aluminosilicate nanoparticles; and obtaining one or more fluorescent image(s) of the region within the individual (e.g., (c) detecting emitted light, the detected light having been emitted by the one or more dye molecule(s) in the individual as a result of excitation by the excitation light; and (d) processing signals corresponding to the detected light to provide one or more image(s) (e.g., a real-time video stream), which may be one or more optical super-resolution image(s), of the region within the individual). Imaging methods of the present disclosure can provide sub-diffraction limit resolution. The imaging methods can be referred to as super-resolution (SR) imaging methods. In various examples, an imaging method provides (e.g., exhibits) sub-diffraction limit resolution, where the diffraction limit is $\lambda/2$ and $\lambda$ is the wavelength of the excitation light. In various examples, an imaging method provides (e.g., exhibits) a resolution 10% or less, 20% or less, or 50% or less than the diffraction limit. Following administration of aluminosilicate nanoparticles or a composition comprising the aluminosilicate nanoparticles, the path, location, and clearance of the aluminosilicate nanoparticles may be monitored using one or more imaging technique(s) of the present disclosure. In various examples, the spatial and/or temporal distribution of the nanoparticles in a sample or one or more portion(s) thereof.

Various aluminosilicate nanoparticles can be used. The aluminosilicate nanoparticles may be the same or may be a combination of two or more different aluminosilicate nanoparticles. Two or more or all of the aluminosilicate nanoparticles may be different in terms of one or more or all of size, fluorophore composition (e.g., dye composition or the like), number of fluorophores (e.g., dyes or the like), or the like. In various examples, the nanoparticle(s) are those described in or made by a method disclosed in International Patent Application No. PCT/US16/30752 (titled "Ultrasmall Nanoparticles and Methods of Making and Using Same"; and published as International Patent Application Publication No. WO 2016/179260 on Nov. 10, 2016).

In as aspect, the present disclosure provides methods of treatment. A method of the present disclosure can be used to treat an individual (e.g., an individual diagnosed with or suspected of having cancer). In various examples, a method of treating an individual for cancer comprises: obtaining an image of a sample (e.g., a biological material) or a portion thereof or an individual or a portion thereof. In various examples, a method further comprises subjecting (e.g., administering or the like) to the individual one or more additional cancer treatment(s). In various examples, the additional cancer treatment is chosen from surgery, radiotherapy, chemotherapy, toxin therapy, immunotherapy, cryotherapy, gene therapy, and combinations thereof.

In an aspect, the present disclosure provides compositions. The compositions comprise a plurality of aluminosilicate nanoparticles of the present disclosure. In various examples, at least a portion of or all of the nanoparticles are surface functionalized with one or more type(s) of polyethylene glycol groups (e.g., polyethylene glycol groups, functionalized (e.g., functionalized with one or more ligand(s) and/or reactive group(s)) polyethylene glycol groups, or any combination thereof). In various examples, a composition further comprises an aqueous medium and the nanoparticles are present as a dispersion in the aqueous medium. In various examples, a composition further comprises a buffer suitable for administration to an individual (e.g., a mammal such as, for example, a human). In various examples, a composition comprises one or more pharmaceutically acceptable carrier(s) and/or excipient(s).

In an aspect, the present disclosure provides kits. A kit comprises one of more aluminosilicate nanoparticle(s) and/or one or more composition(s) of the present disclosure. In various examples, a kit comprises one or more aluminosilicate nanoparticle(s) of the present disclosure and/or one or more composition(s) of the present disclosure, and instructions for use of the nanoparticle(s) and/or composition(s) for treatment of (e.g., administration to) an individual. In various examples, a kit is or comprises a closed or sealed package that contains the aluminosilicate nanoparticle(s) and/or composition(s). In certain examples, the package comprises one or more closed or sealed vial(s), bottle(s), blister (bubble) pack(s), or any other suitable packaging for the sale, or distribution, or use of the nanoparticle(s) and/or composition(s). The printed material can include printed information (e.g., printed information that includes information that identifies the compound in the package, the amounts and types of other active and/or inactive ingredients, and instructions for taking the composition, such as, for example, the number of doses to take over a given period of time, and/or information directed to a pharmacist and/or another health care provider, such as, for example, a physician, or a patient, an indication that the pharmaceutical composition and/or any other agent provided with it is for treatment of cancer and/or any disorder associated with cancer, or the like.

BRIEF DESCRIPTION OF THE FIGURES

For a fuller understanding of the nature and objects of the disclosure, reference should be made to the following detailed description taken in conjunction with the accompanying figures in the Example.

(FIG. 1A) a rendering of internal environment of aC' dot encapsulating Cy5 (Si, white; O, gray; Al, blue); (FIG. 1B) a normalized gel permeation chromatography (GPC) elution profile of PEG-Cy5-aC' dots; (FIG. 1C) a normalized and absorbance-matched absorbance (left) and emission (right) spectra of Cy5 dye and PEG-Cy5-aC' dots in water; (FIG. 1D) a confocal fluorescence correlation spectroscopy (FCS) autocorrelation curve with fit of PEG-Cy5-aC' dots diffusing in water; and (FIG. 1E) photobleaching experiments of Cy5 dye and PEG-Cy5-aC' dots in water with single exponential fit. BE: Brightness Enhancement; SE: Stability Enhancement.

(FIGS. 2A-2D) single-molecule fluorescence traces for Cy5-biotin dye, (FIGS. 2E-211) PEG-Cy5-C' dot, and (FIGS. 2I-2J) PEG-Cy5-aC' dot under different conditions (50 ms (ms=millisecond(s)) integration times): (FIGS. 2A, 2E, 2I) red laser; (FIGS. 2B, 2F) red and UV laser; (FIGS. 2C, 2J) red and UV laser with βME and OS; (FIGS. 2D, 2H) red laser and Al salt; and (Fig. J) red laser and OS. Different color lines represent traces from different emitters. Numbers above the spectra represent the average equilibrium duty cycles. Red laser and UV laser signify a 640 nm and a 405 nm light source, respectively. βME is β-mercaptoethanol. OS is an oxygen scavenging system. Al salt is dissolved sodium aluminate. HBSS was used as the imaging buffer in all cases.

(FIGS. 3A-3D) single molecule fluorescence traces (50 ms integration time) of Cy5-dye with sodium aluminate (FIGS. 3A-3B) as well as PEG-Cy5-aC' dots (FIGS. 3C-3D) without radical scavenger, tert-butanol (FIGS. 3A, 3C) and with radical scavenger, tert-butanol (FIGS. 3B, 3D), suggesting that blinking occurs via a radical ion mechanism; (FIGS. 3E, 3H) single-molecule fluorescence traces of immobilized PEG-Cy5-aC' dots (top) and PEG-Cy5-C' dots (bottom) in HBSS and exposed to 640 nm laser excitation (1 ms integration times); (FIGS. 3F, 3I) imaging FCS autocorrelation of fluorescence traces with fits to single exponential functions. Only the first 10 seconds of FIG. 311 were autocorrelated in FIG. 3I. Inset in FIG. 3I has a rescaled y axis to visualize entire data range; and (FIGS. 3G, 3J) suggested Jablonski diagrams depicting relevant dye electronic states and transitions for each system investigated.

Figure 4A:
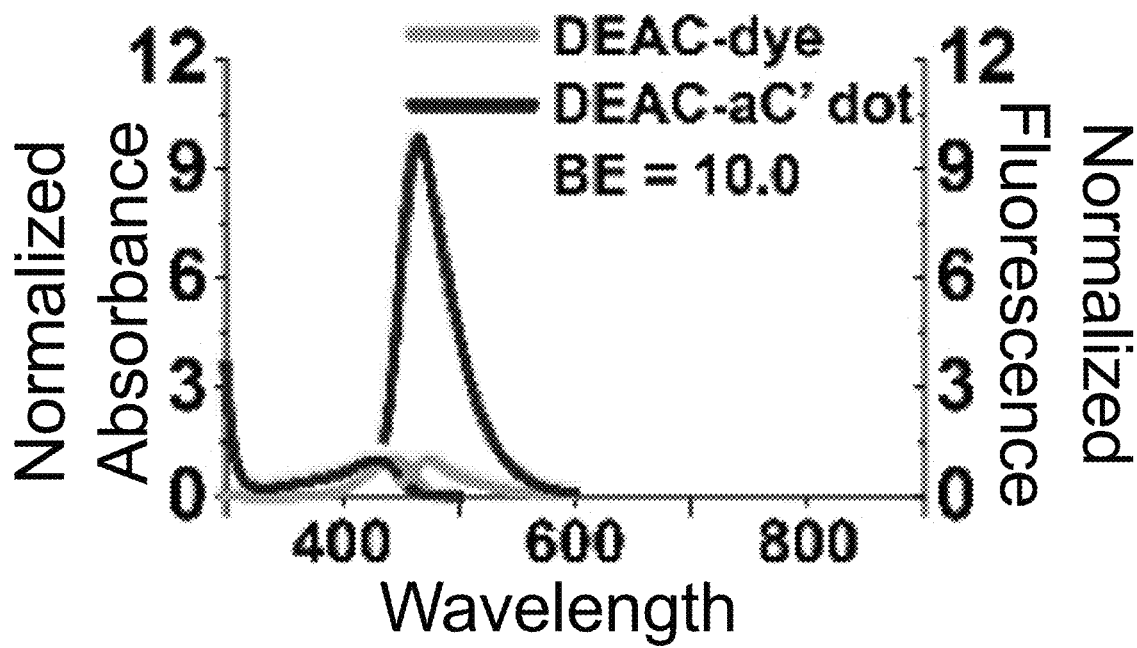
FIGS. 4A-4O show.
Figure 4B:
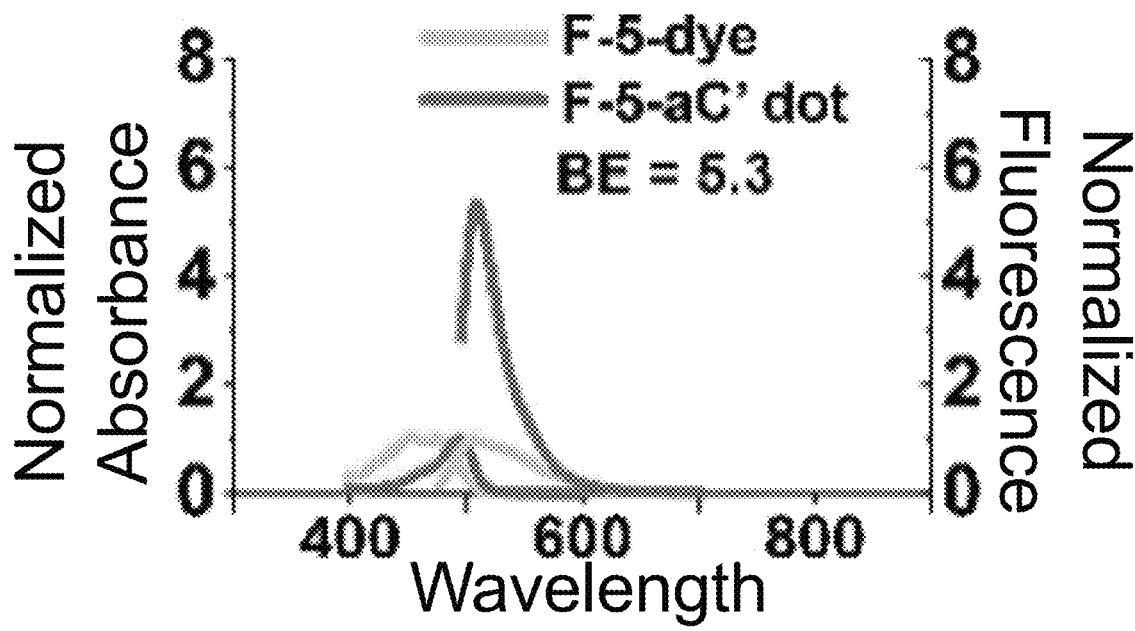
Figure 4C:
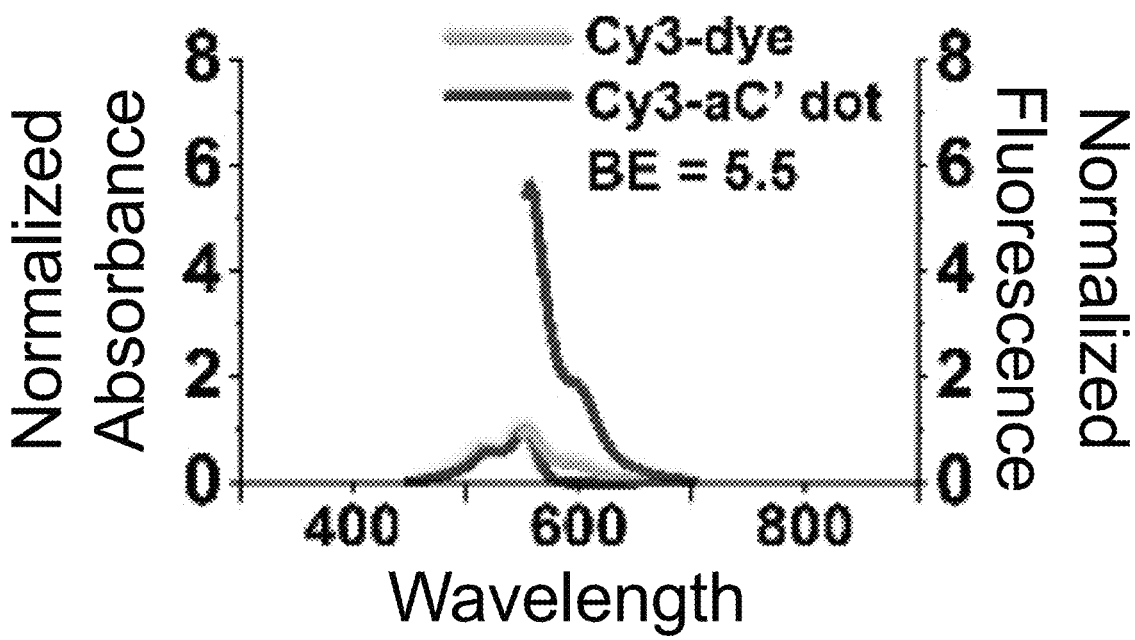
Figure 4D:
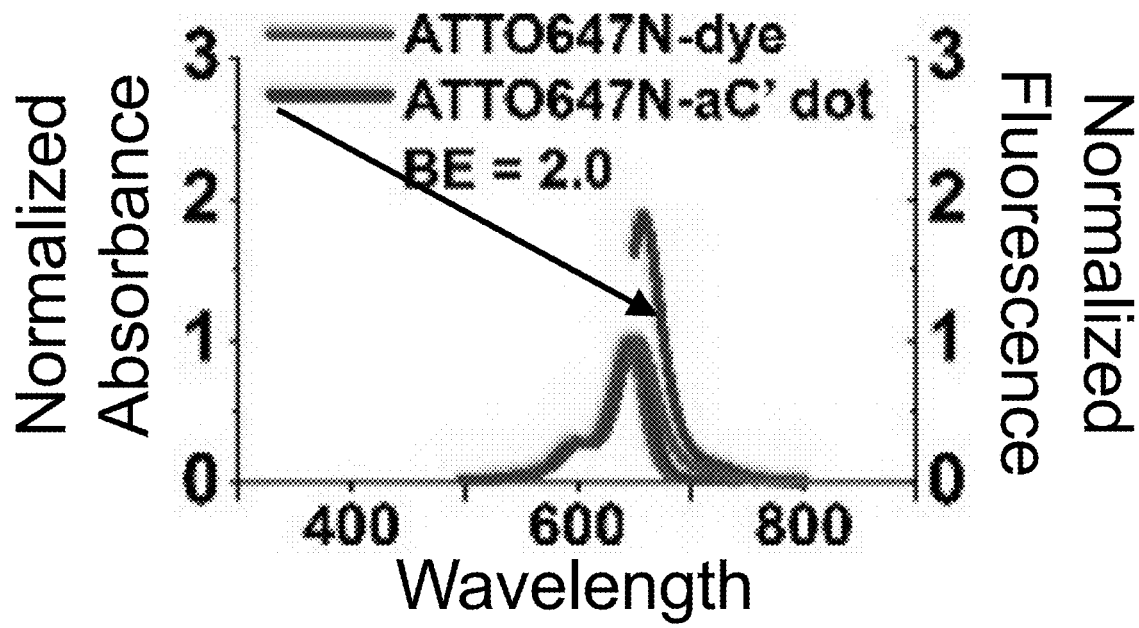
Figure 4E:
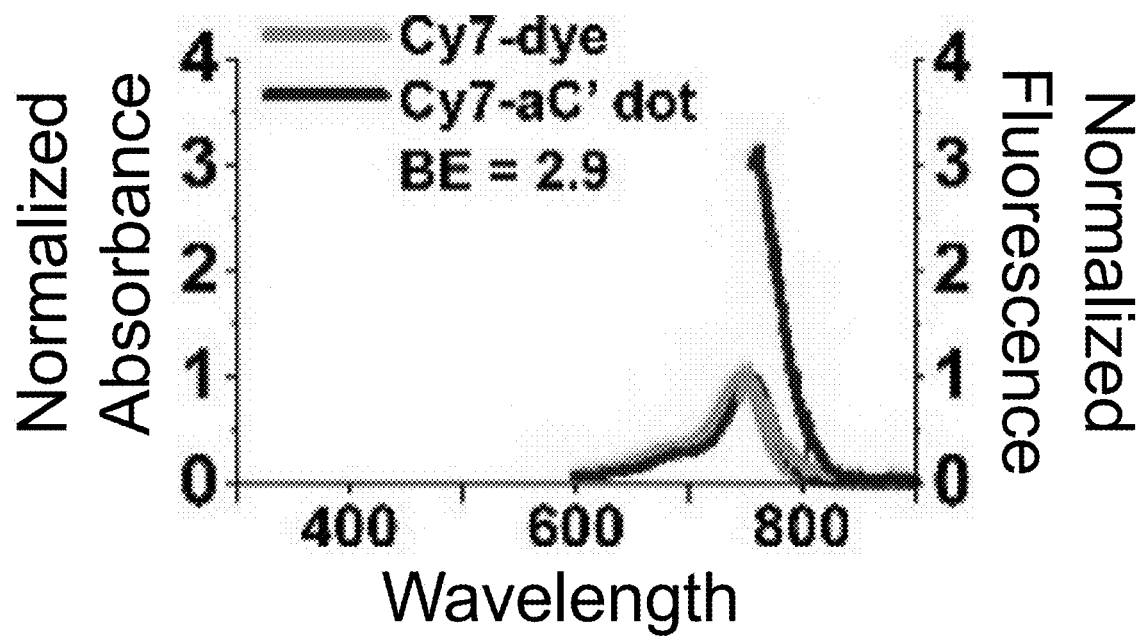
Figure 4F:
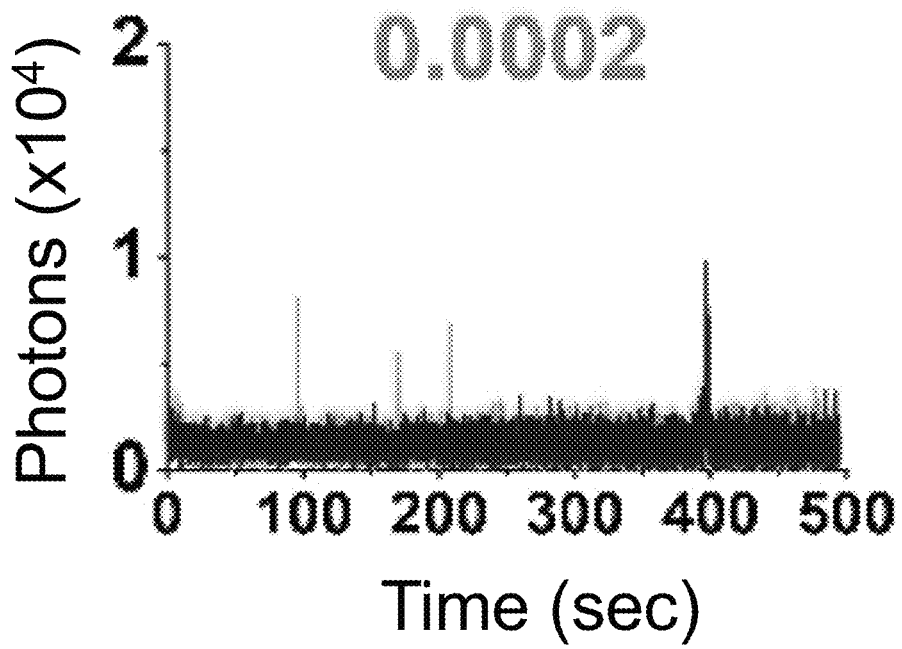
(FIGS. 4F-4J) single-molecule fluorescence traces (50 ms integration time) of immobilized PEG-DEAC-aC' dots (FIG. 4F), PEG-F-5-aC' dots (FIG. 4G), PEG-Cy3-aC' dots (FIG. 411), PEG-ATTO647N-aC' dots (FIG. 4I), and PEG-Cy7-aC' dots (FIG. 4J), corresponding equilibrium duty cycles are shown above the spectra.
Figure 4G:
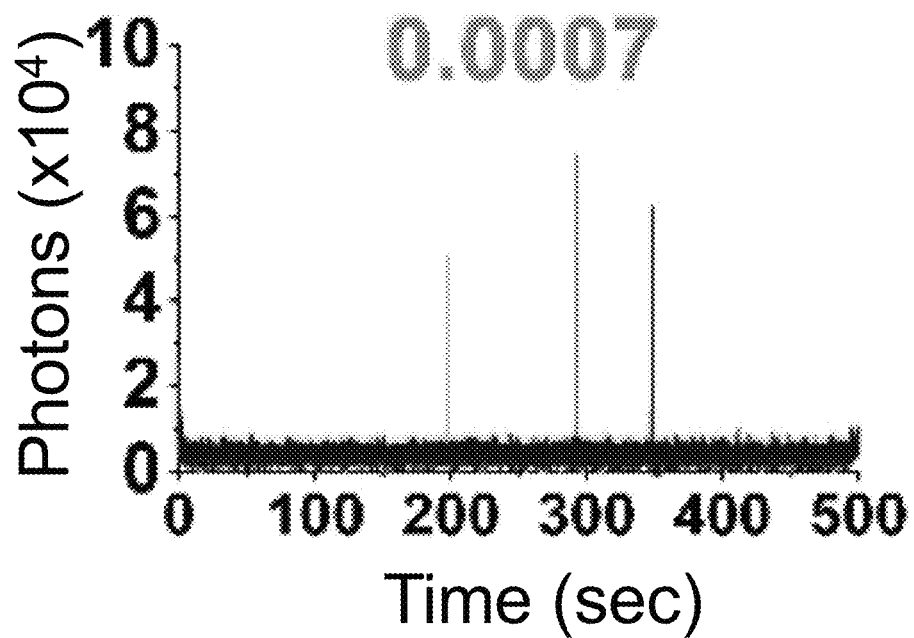
Figure 4H:
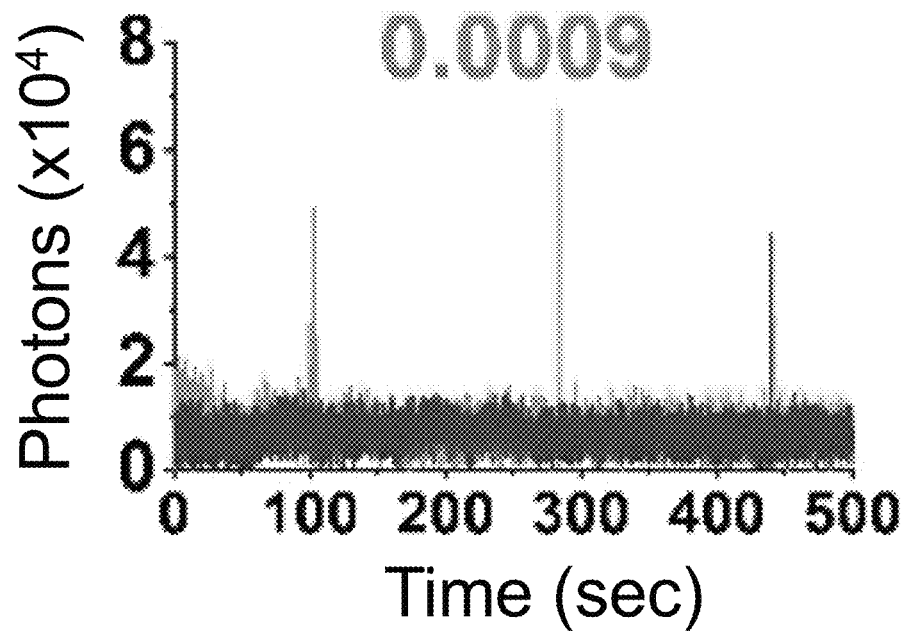
Figure 4I:
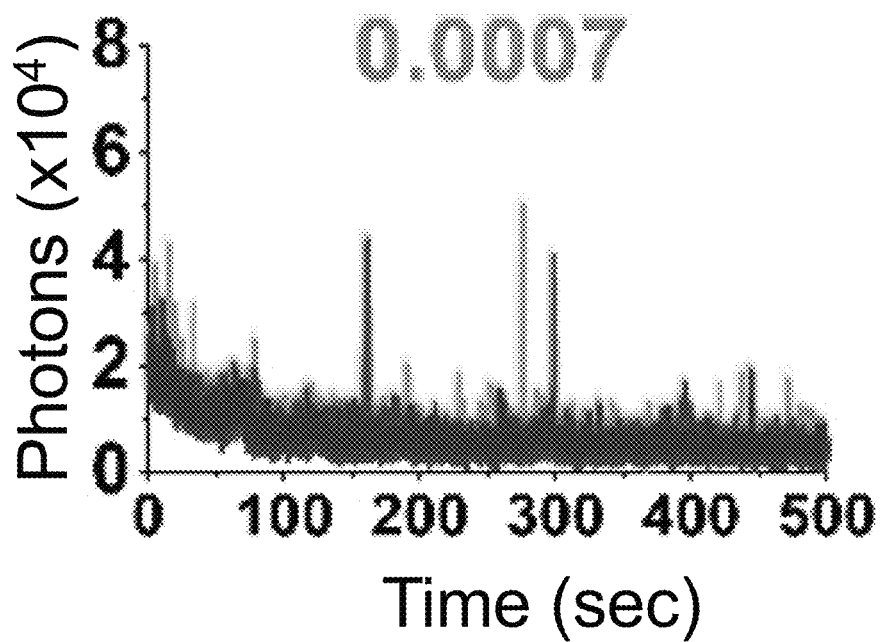
Figure 4J:
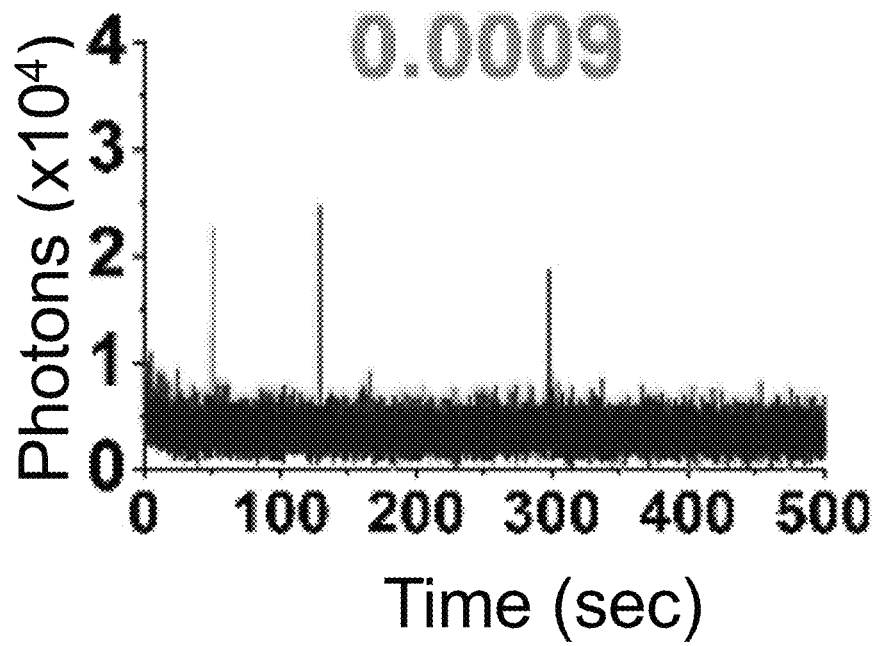
Figure 4K:
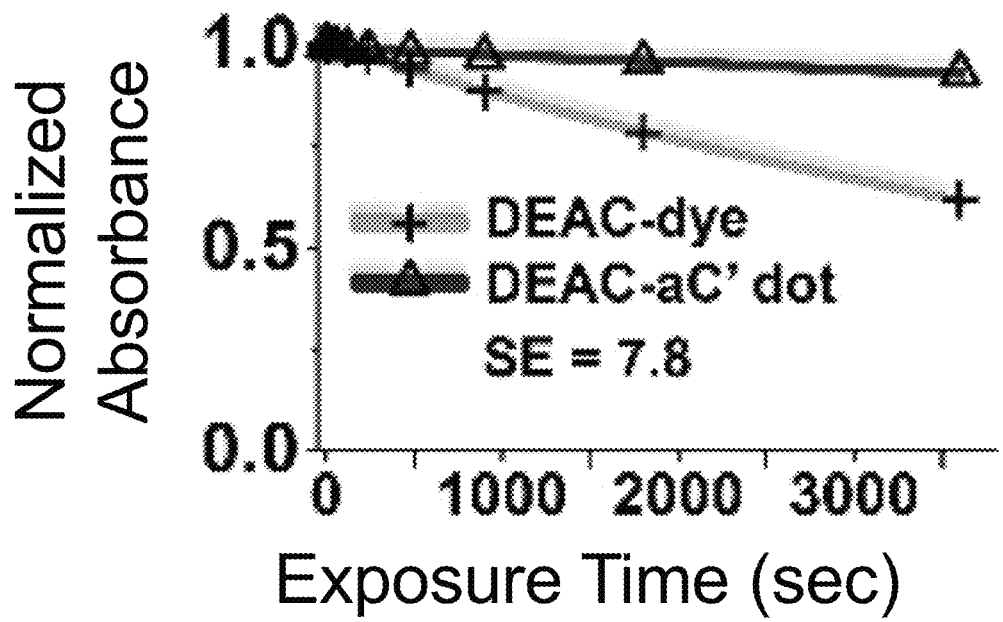
Figure 4L:
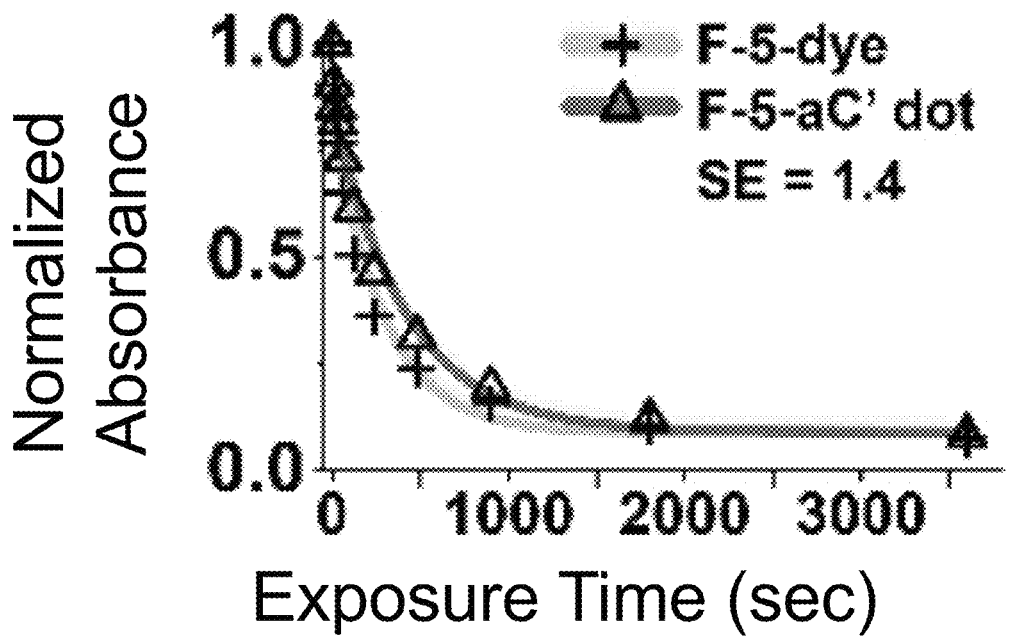
Figure 4M:
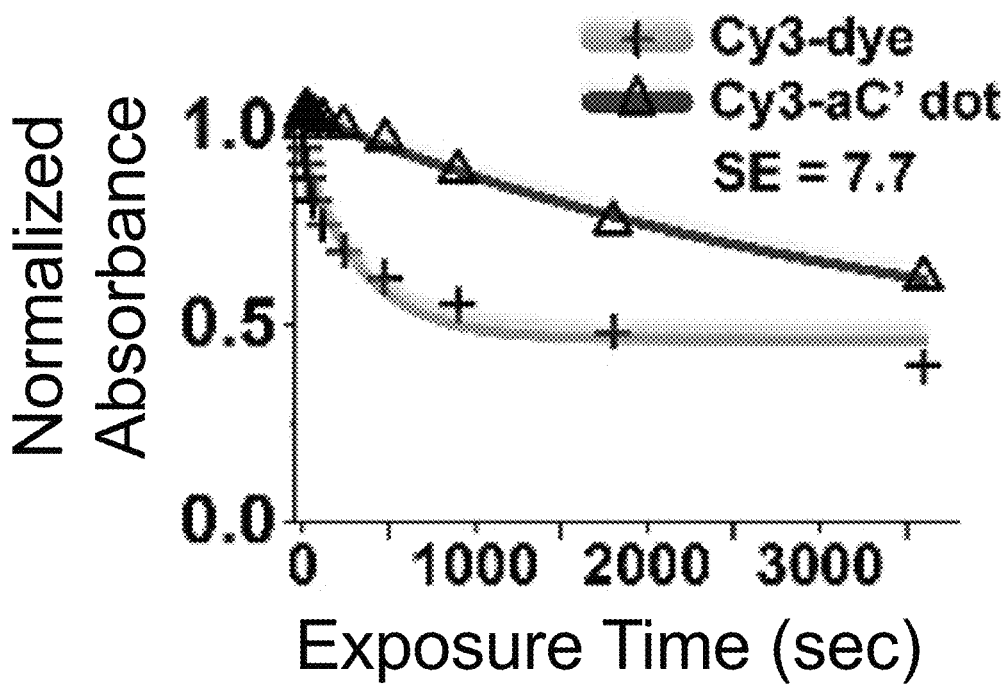
Figure 4N:
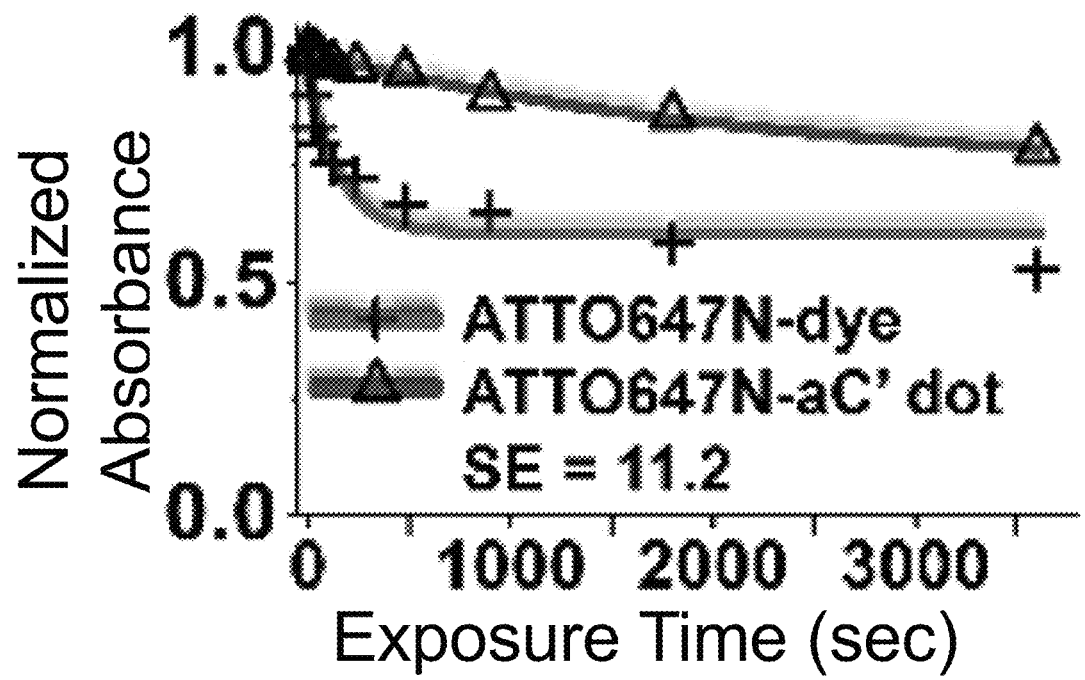
Figure 4O:
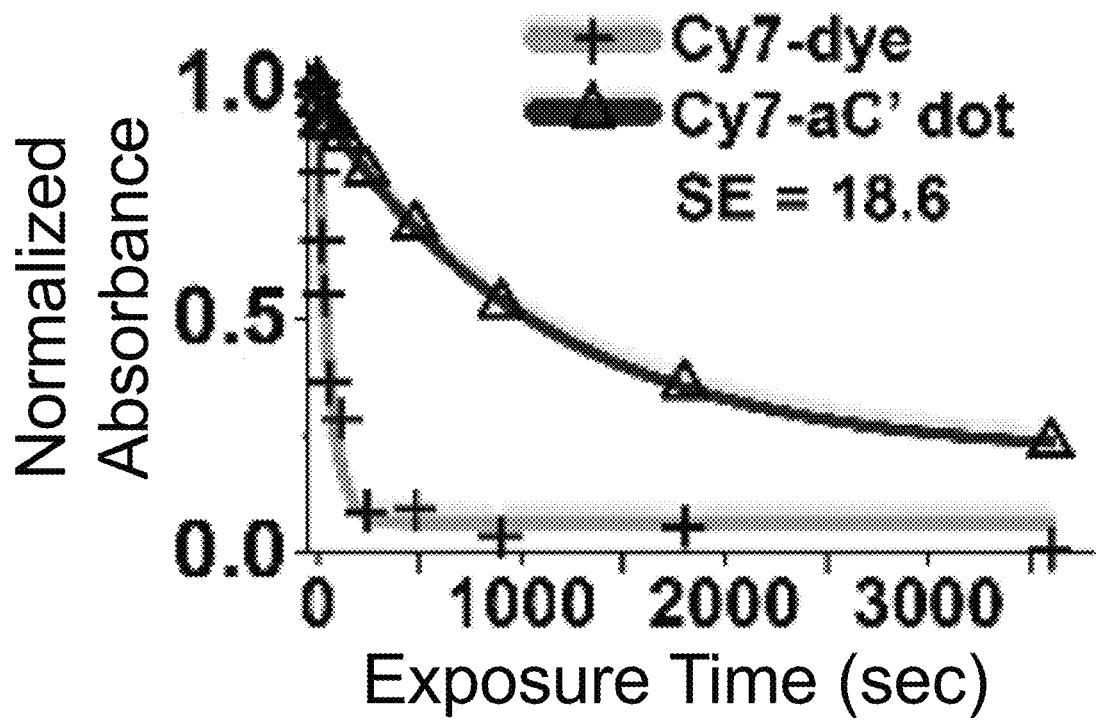

(FIGS. 4A-4E) normalized and absorbance-matched absorbance (left) and emission (right) spectra for PEG-DEAC-aC' dots (FIG. 4A), PEG-F-5-aC' dots (FIG. 4B), PEG-Cy3-aC' dots (FIG. 4C), PEG-ATTO647NaC' dots (FIG. 4D), and PEG-Cy7-aC' dots (FIG. 4F) and their unconjugated free parent dyes DEAC, F-5, Cy3, ATTO647N and Cy7, respectively, in water; (FIGS. 4K-4O) photobleaching experiments of free dyes and PEG-dye-aC' dots in water with single exponential fits. Particles were all in HBSS imaging buffer for single-particle experiments and exposed to their respective excitation light sources: 405 nm (PEG-DEAC-aC' dots (FIG. 4K)), 488 nm (PEG-F-5-aC' dots) (FIG. 4L), 561 nm (PEG-Cy3-aC' dots (FIG. 4M)), and 640 nm (PEGATTO647N-aC' dots (FIG. 4N) and PEG-Cy7-aC' dots (FIG. 4O)). BE: Brightness Enhancement; SE: Stability Enhancement.

Figure 5A:
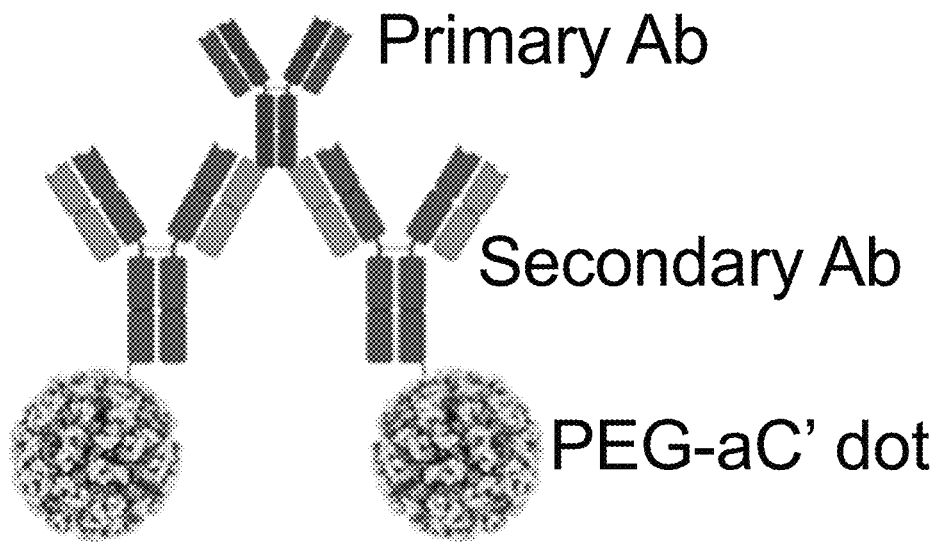

FIGS. 5A-5D show: (FIG. 5A) illustration of two goat anti-mouse IgG secondary antibody ($Ab_2$)-PEG-aC' dot conjugates binding to one mouse anti-α-tubulin primary antibody; (FIG. 5B) diffraction-limited TIRF image of a fixed and permeabilized HeLa cell labeled with mouse anti-α-tubulin primary antibodies followed by Abe-PEG-ATTO647N-aC' dots (red) staining; (FIG. 5C) STORM reconstruction of FIG. 5B; and (FIG. 5D) intensity profiles of a line across a tubulin structure, highlighted by the yellow boxes in FIGS. 5B-5C. Profiles were normalized and fit to a Gaussian function to obtain the data shown in FIG. 5D, demonstrating the improvement in resolution to below the diffraction limit. Please note that the achievable resolution is limited by the fact that typically two aC' dots are conjugated to a single primary antibody as shown in FIG. 5A. Cells were stained with Hoechst 33342 (blue) to visualize the nucleus. Images were taken with only a 640 nm excitation light source in PBS.

FIGS. 6A-6J show: (FIG. 6A) live cell composite TIRF image of MDA-MB-231 TNBC cell stained with Hoechst 33342 (blue) and CellMask Orange (green) containing endocytosed PEG-Cy5-aC' dots (red) in intracellular vesicles; (FIG. 6B) composite image with red channel STORM reconstruction and TIRF overlay; (FIG. 6C) corresponding red channel STORM reconstruction only; (FIGS. 6D-6F) regions in FIGS. 6D-6F corresponding to location boxes indicated in FIG. 6C. Upper panels show three examples of quantified regions containing 131 (FIG. 6D), 7 (FIG. 6E), and 74 (FIG. 6F) nanoparticles. Lower panels show scatter plots of the same data with localization densities of 197 (FIG. 6D), 11 (FIG. 6E), and 111 (FIG. 6F) localizations per square micron; (FIGS. 6G-6I) kernel density plots of number of localizations/particles in three individual cells 1 (FIG. 6G), 2 (FIG. 6H), and 3 (FIG. 6I) versus maximum emitter distance estimates of PEG-Cy5-aC' dot derived localizations. (FIG. 6J) Combination of kernel density plots of 13 individual cells indicating that the number of particles increases as object size increases. Line is a fit to cubic behavior (see main text).

Figure 7A:
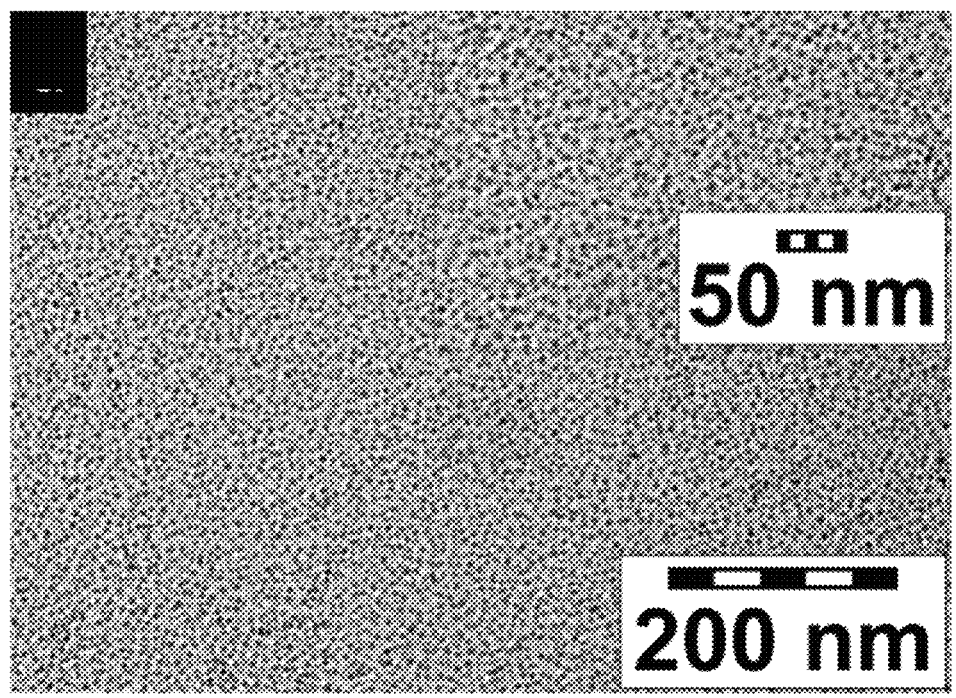
Figure 7B:
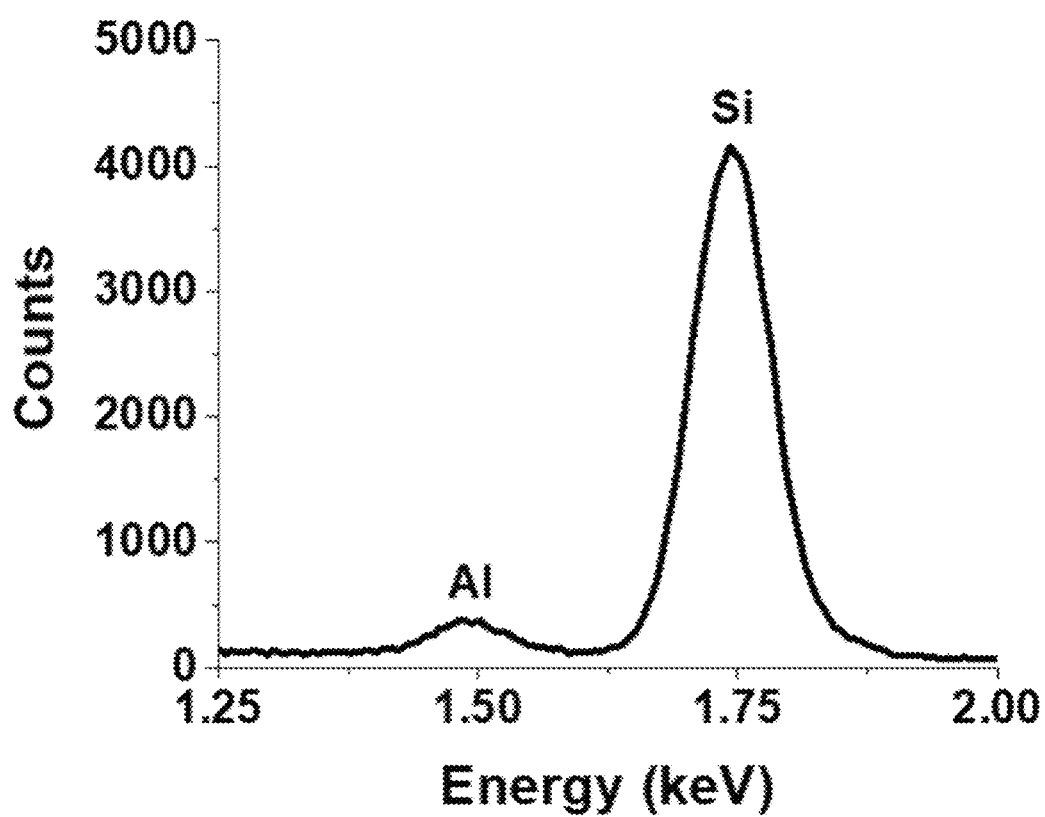

FIGS. 7A-7B show: (FIG. 7A) transmission electron microscopy (TEM) images of PEG-Cy5-aC' dots at two different magnifications; (FIG. 7B) energy-dispersive X-ray spectroscopy (EDS) results for PEG-Cy5-aC' dots.

Figures 8, 9A:
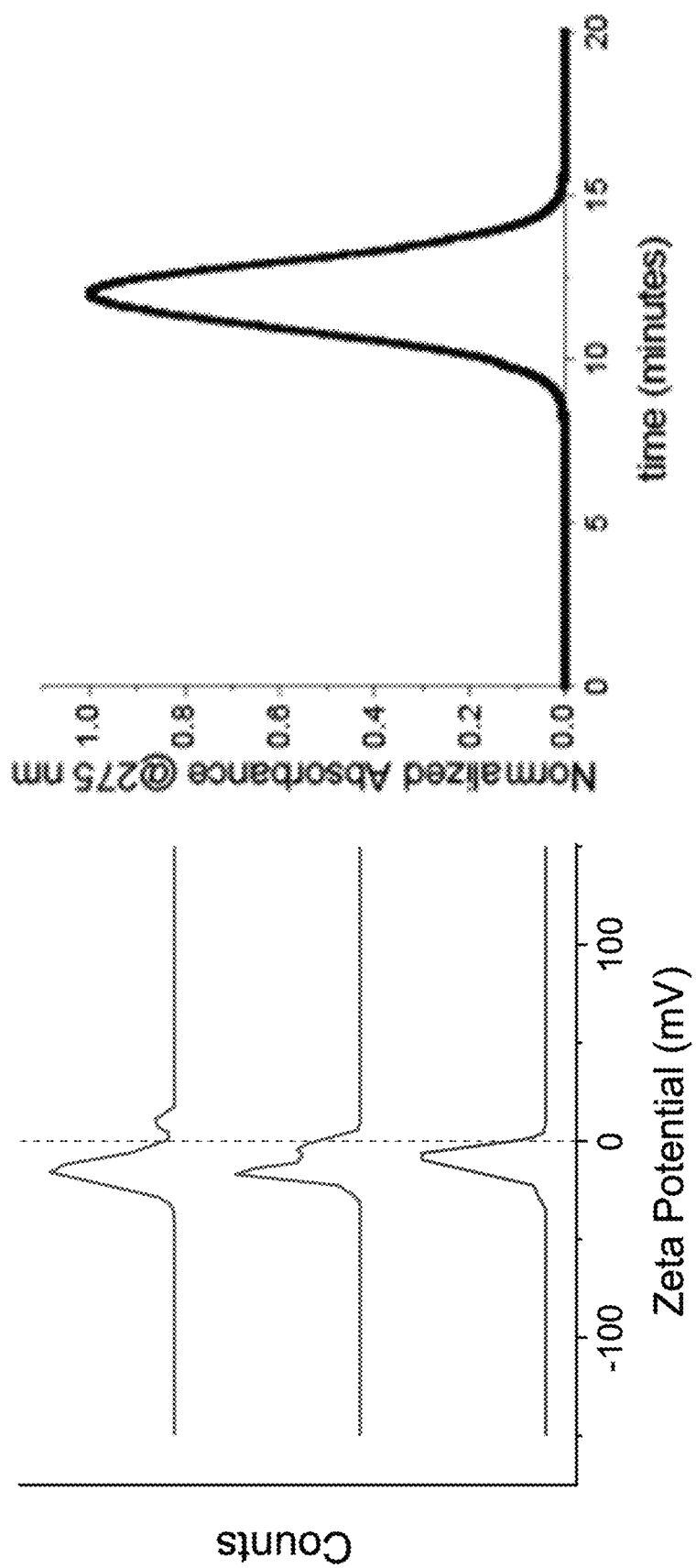

FIG. 8. Zeta potential measurements of PEG-aC' dots from three separate collections. Averaging these three measurements, a zeta potential of −11.9±1.5 mV was obtained.

Figure 9B:
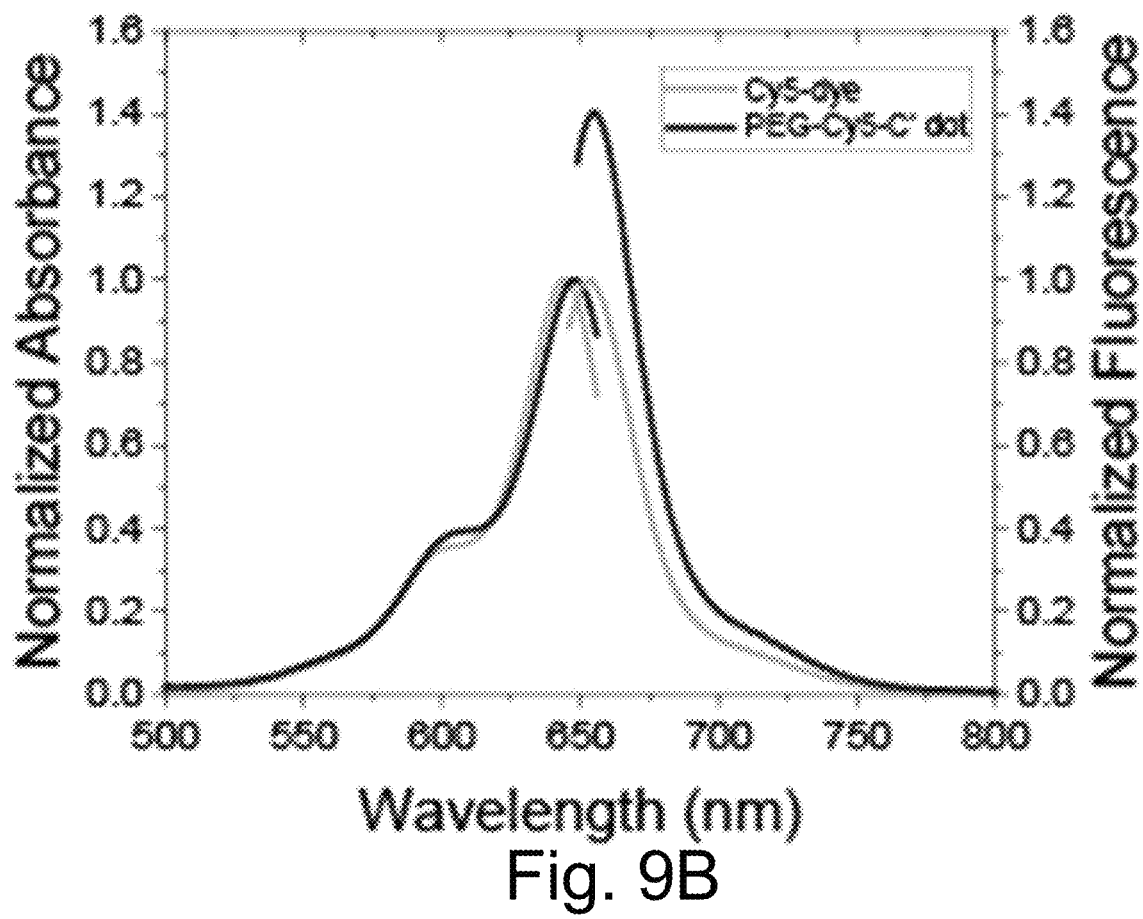
Figure 9C:
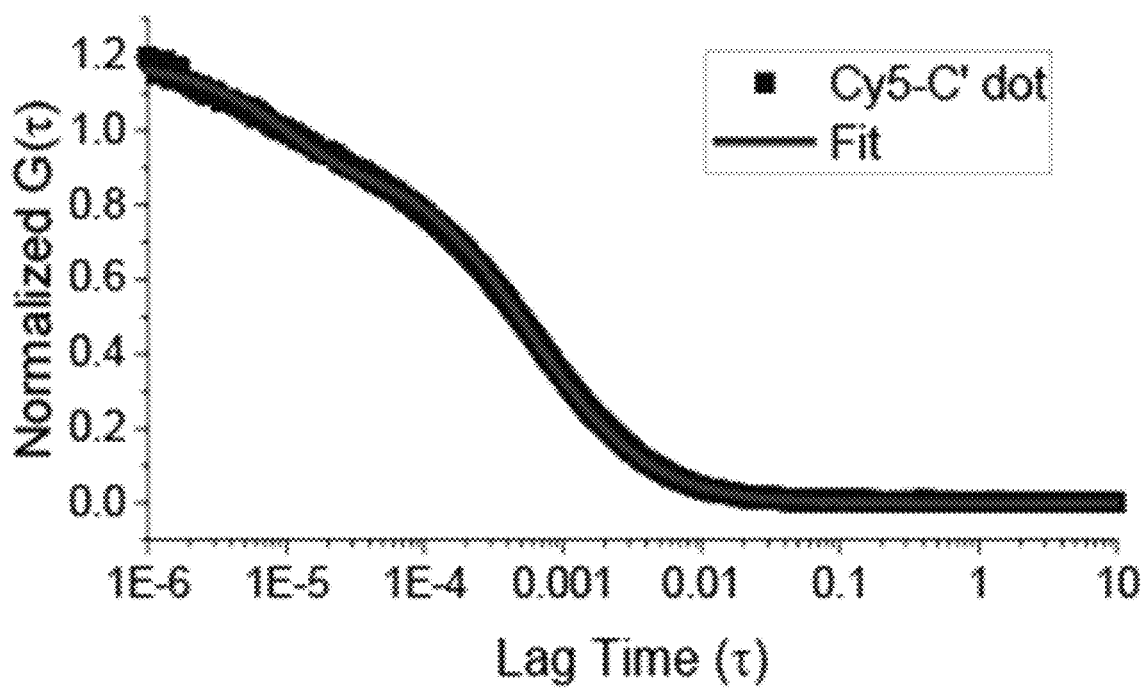

FIGS. 9A-9C show: (FIG. 9A) a PEG-Cy5-C' dot GPC chromatogram; (FIG. 9B) absorbance matched absorption and emission spectra of PEG-Cy5-C' dots compared to parent free dye; and (FIG. 9C) confocal FCS autocorrelation curve with fit of PEG-Cy5-C' dots.

Figure 10:
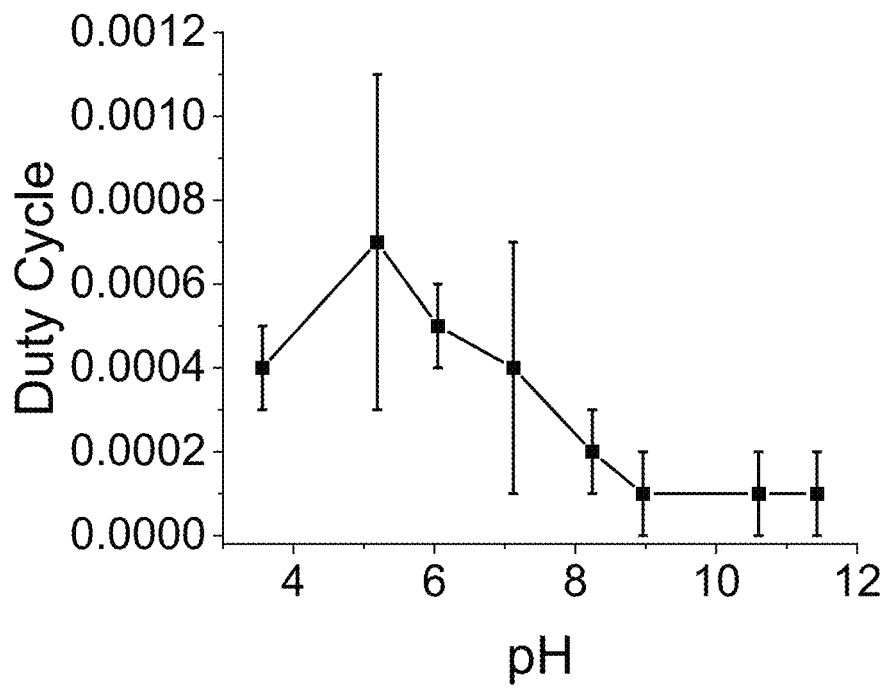

FIG. 10 shows that PEG-Cy5-aC' dots exhibit only a weak dependence of equilibrium duty cycle on buffer pH.

Figure 11A:
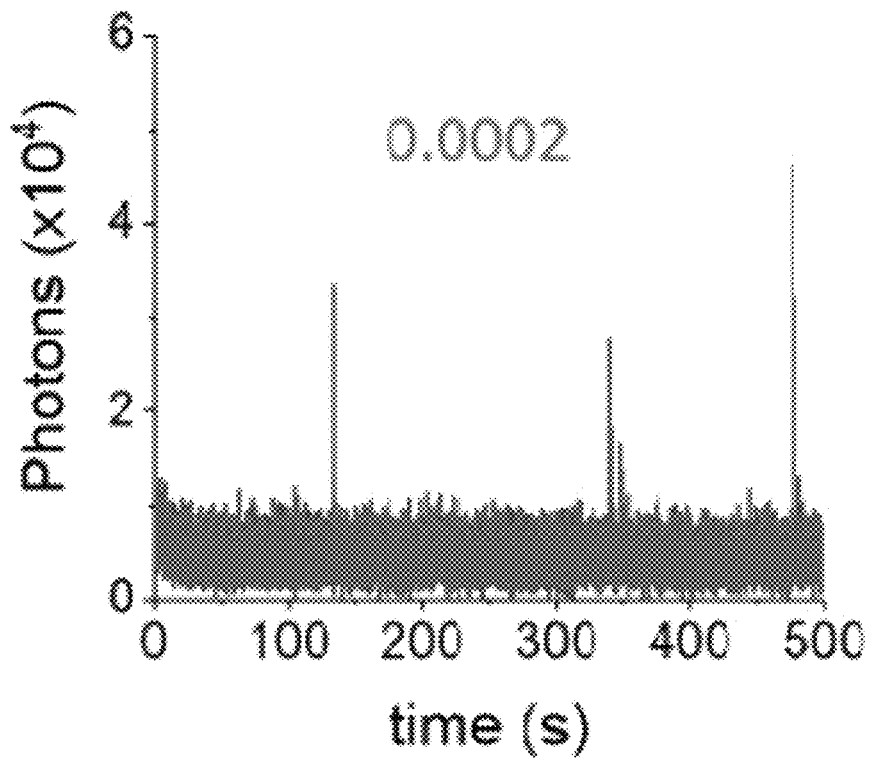
Figure 11B:
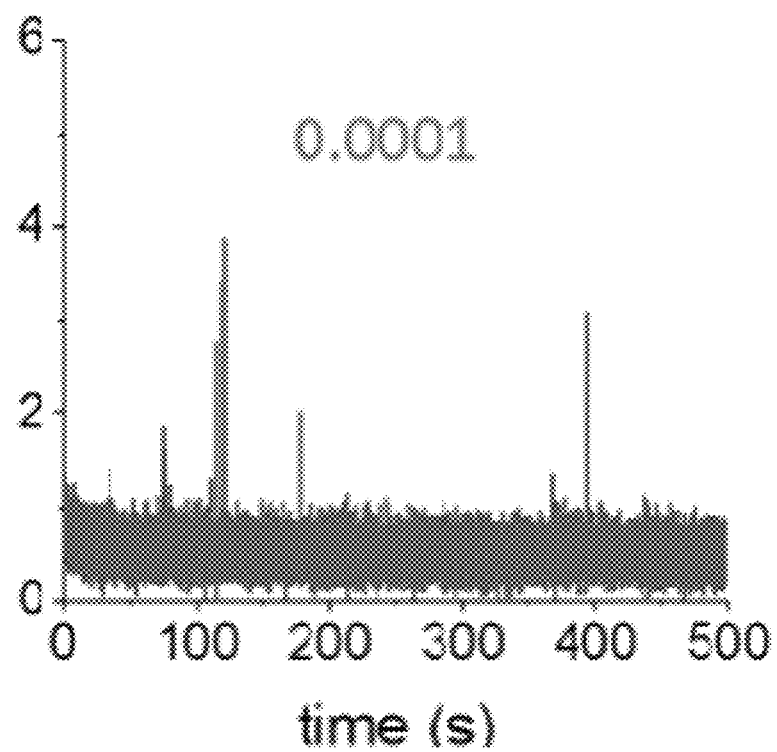
Figure 11C:
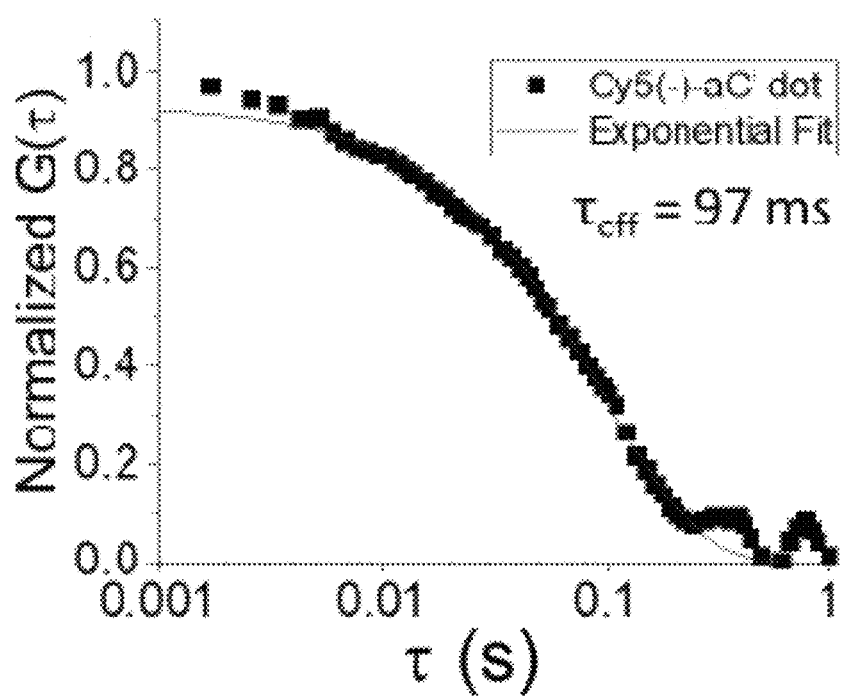
Figure 11D:
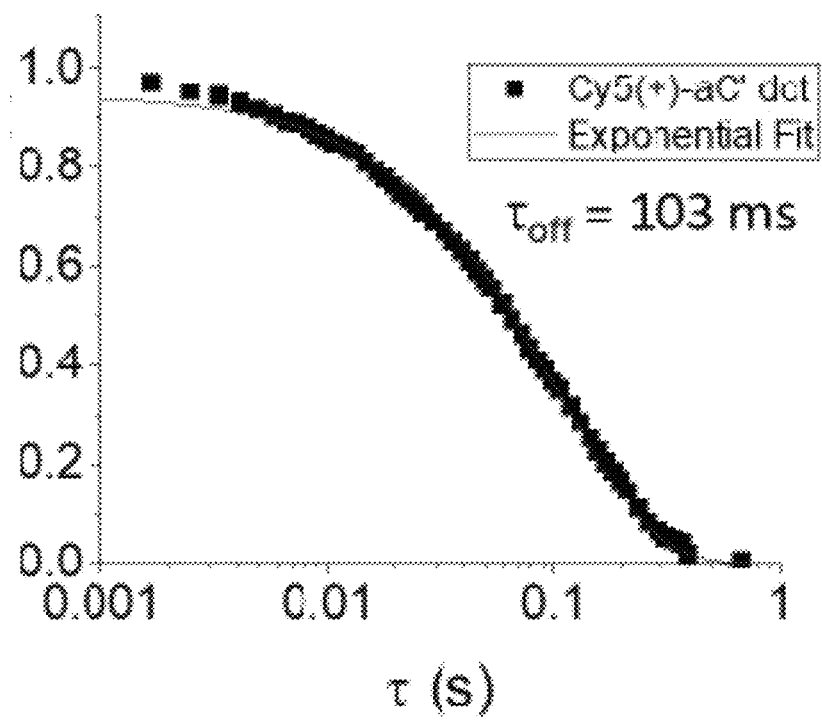

FIGS. 11A-11D show: PEG-Cy5-aC' dots exhibiting similar duty cycles (FIGS. 11A-11B; 50 ms integration times) and $\tau_{off}$ times (FIGS. 11C-11D; 1 ms integration time), irrespective of whether the encapsulated Cy5 is negatively charged (sulfo-Cy5) (FIGS. 11A, 11C) or positively charged (FIGS. 11B, 11D).

Figure 12:
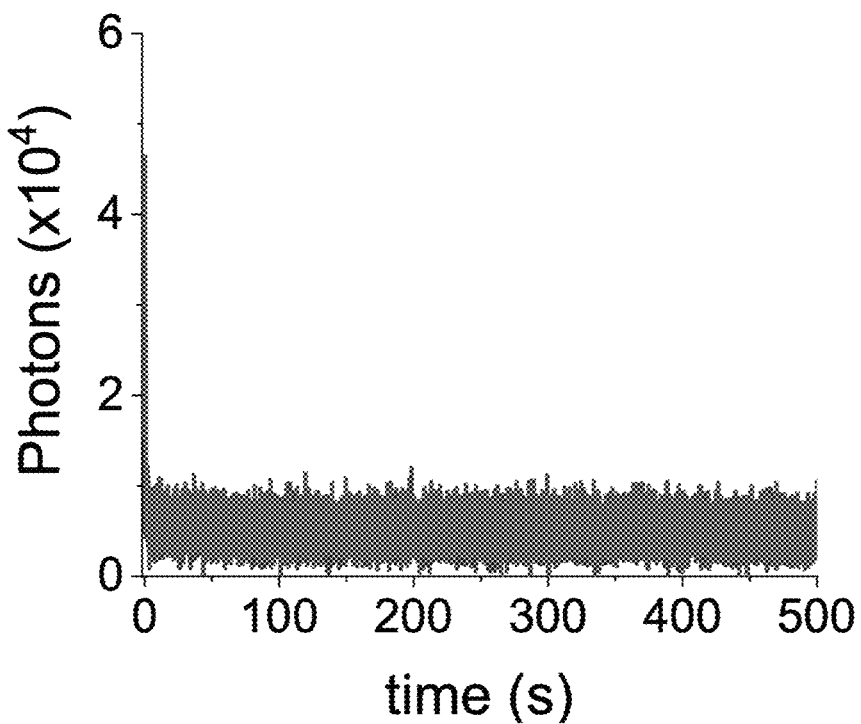

FIG. 12 shows a single-localization fluorescence time trace (50 ms integration time) of Cy5-dye in the presence of aluminum chloride in HBSS with only red laser exposure.

Figure 13:
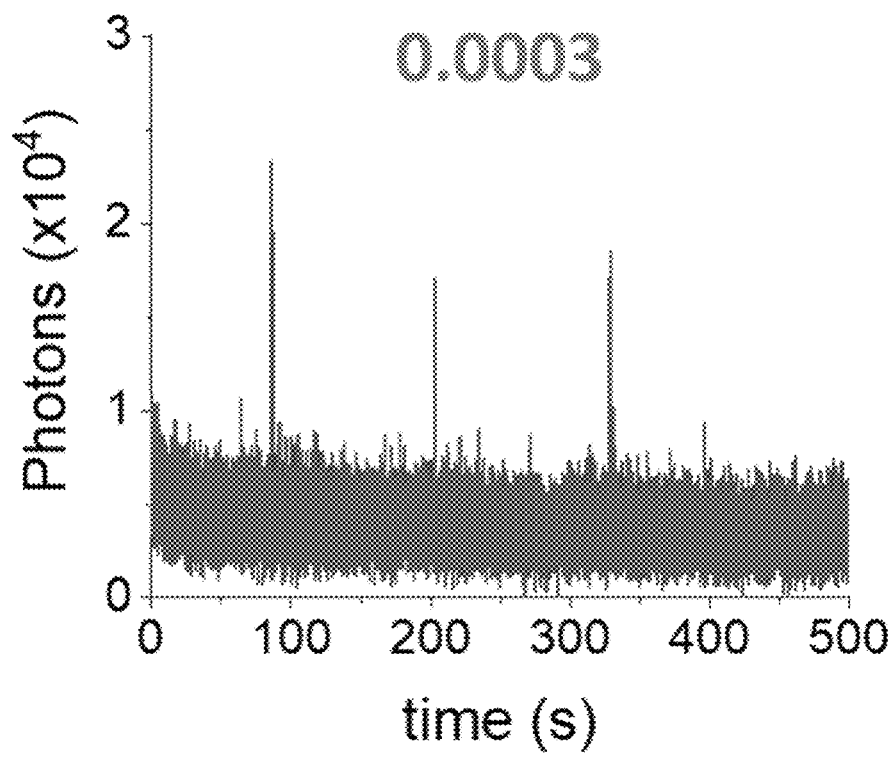

FIG. 13 shows a single-localization fluorescence time trace (50 ms integration time) of PEG-Cy5-aC' dots in ethanol with only red laser exposure.

Figure 14A:
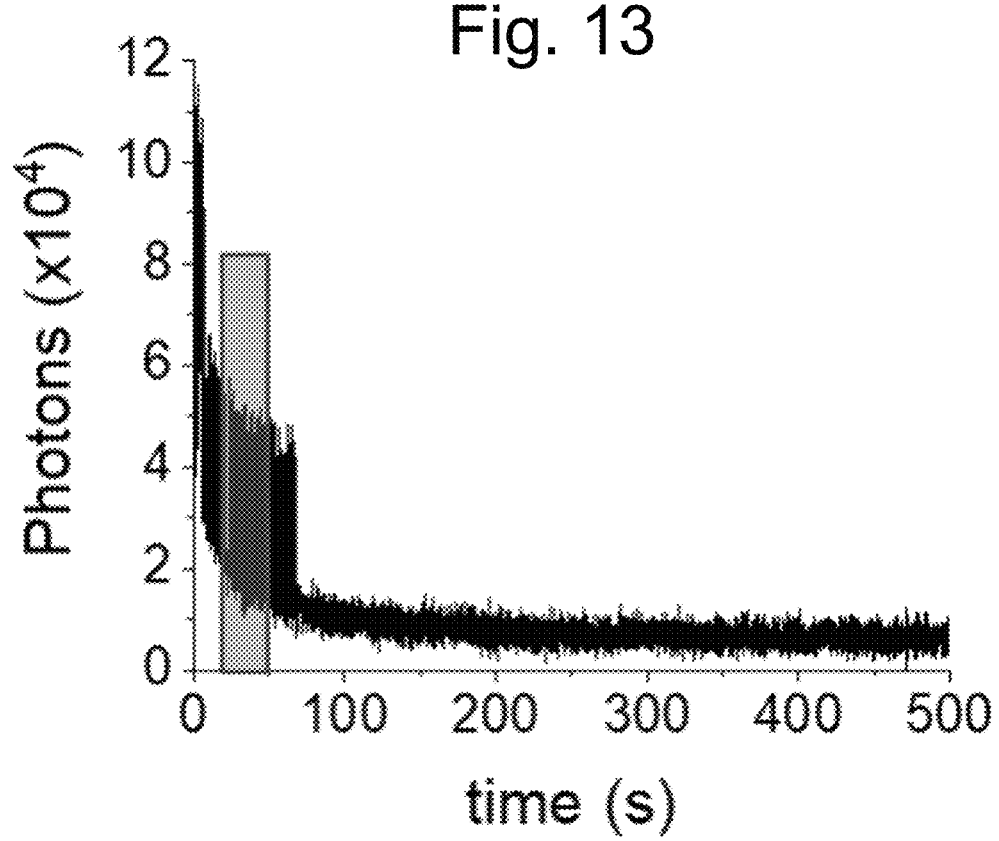
Figure 14B:
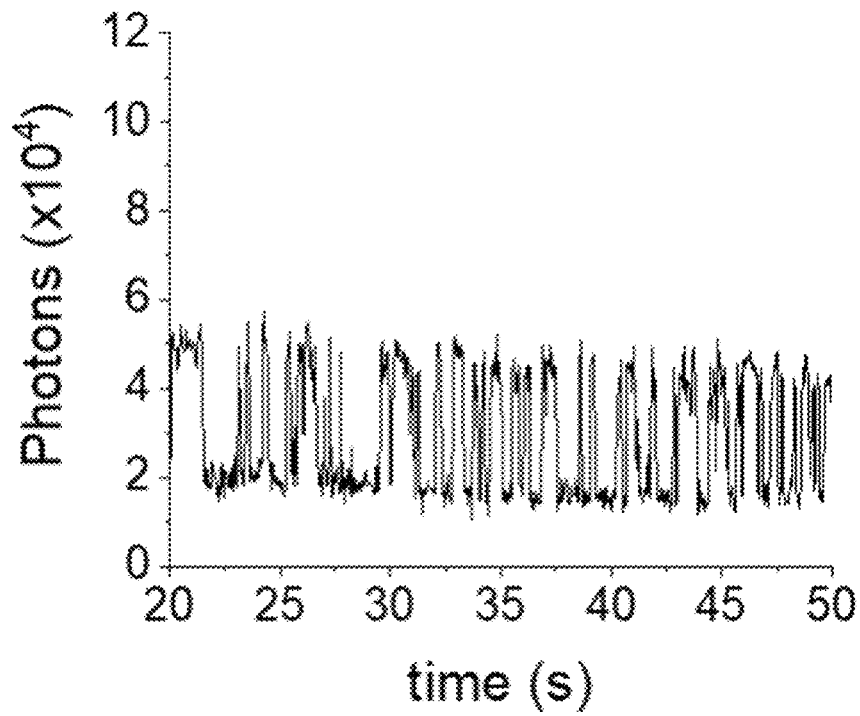
Figure 14C:
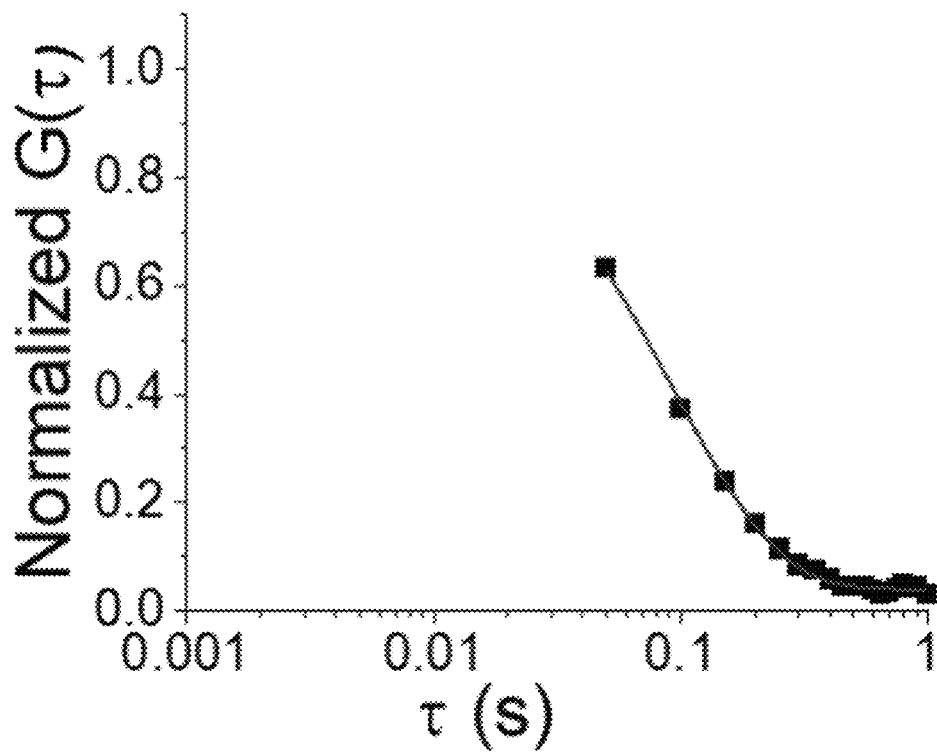
Figure 15A:
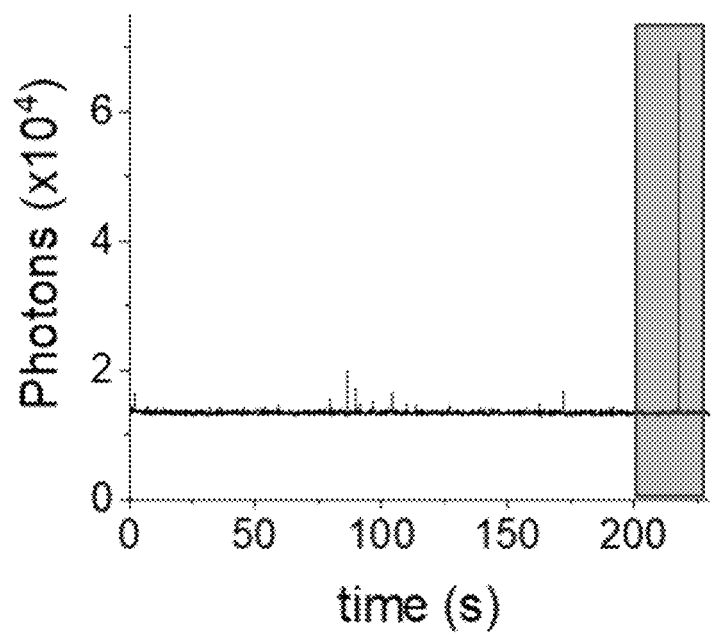
Figure 15B:
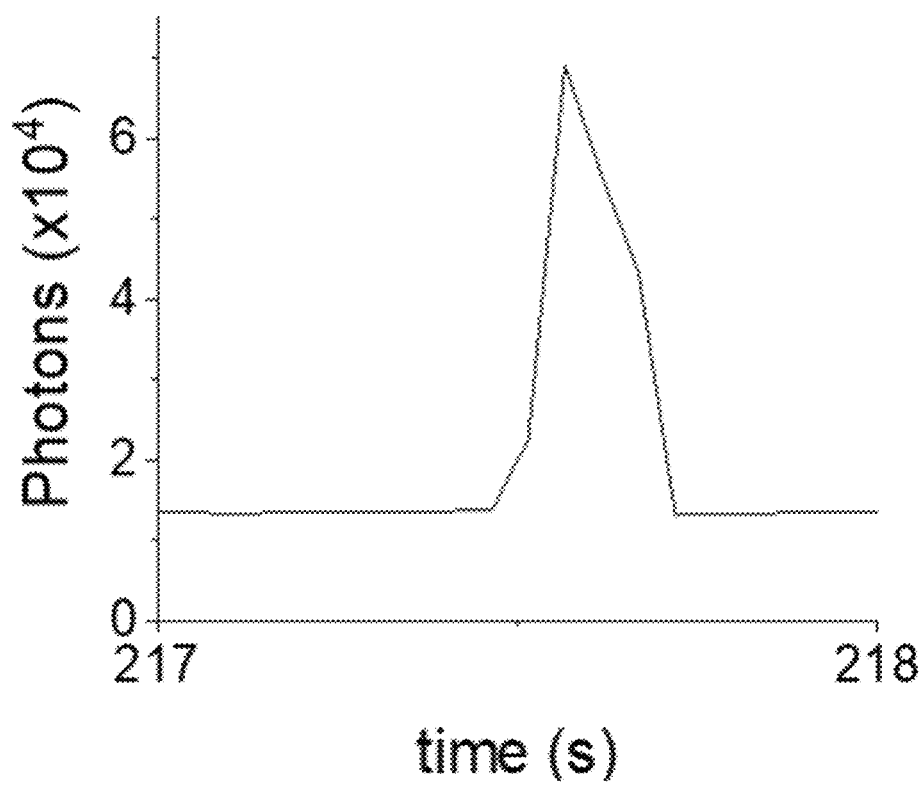
Figure 15C:
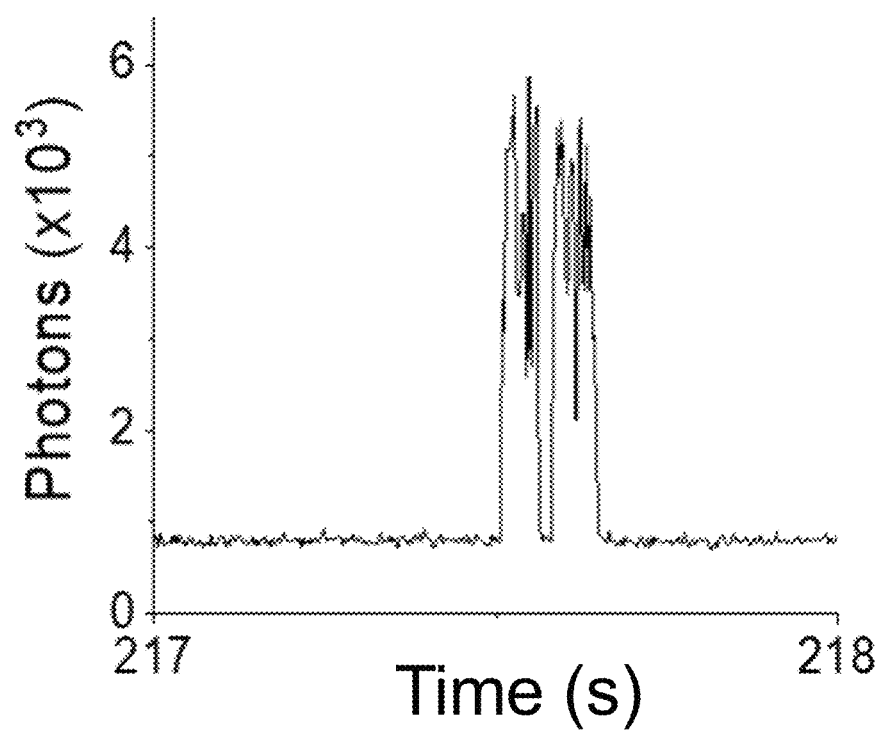
Figure 15D:
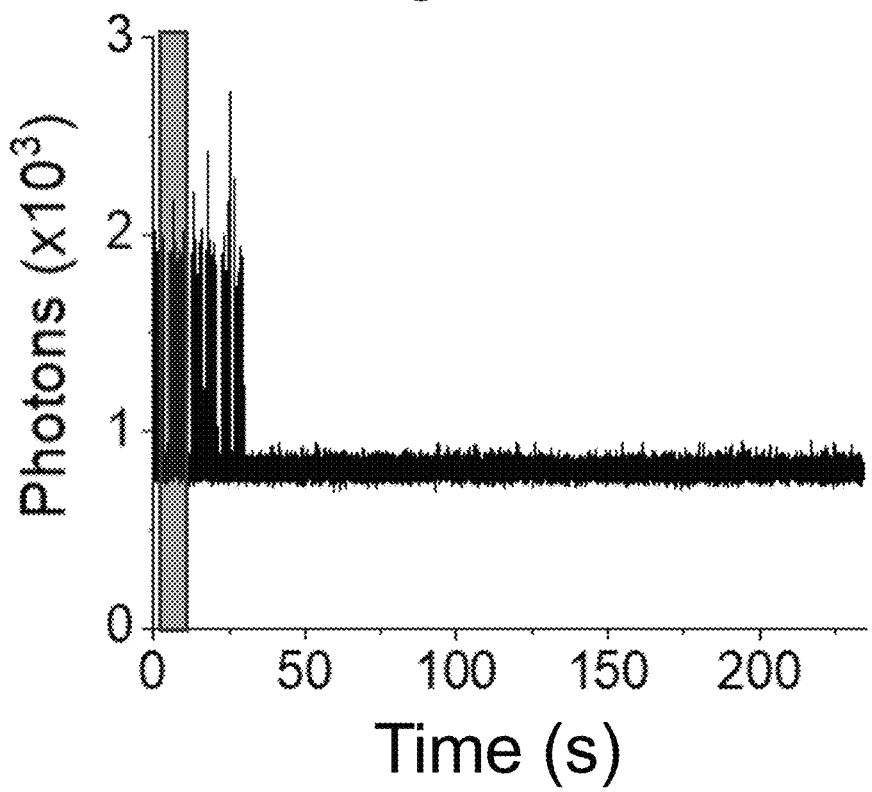
Figure 15E:
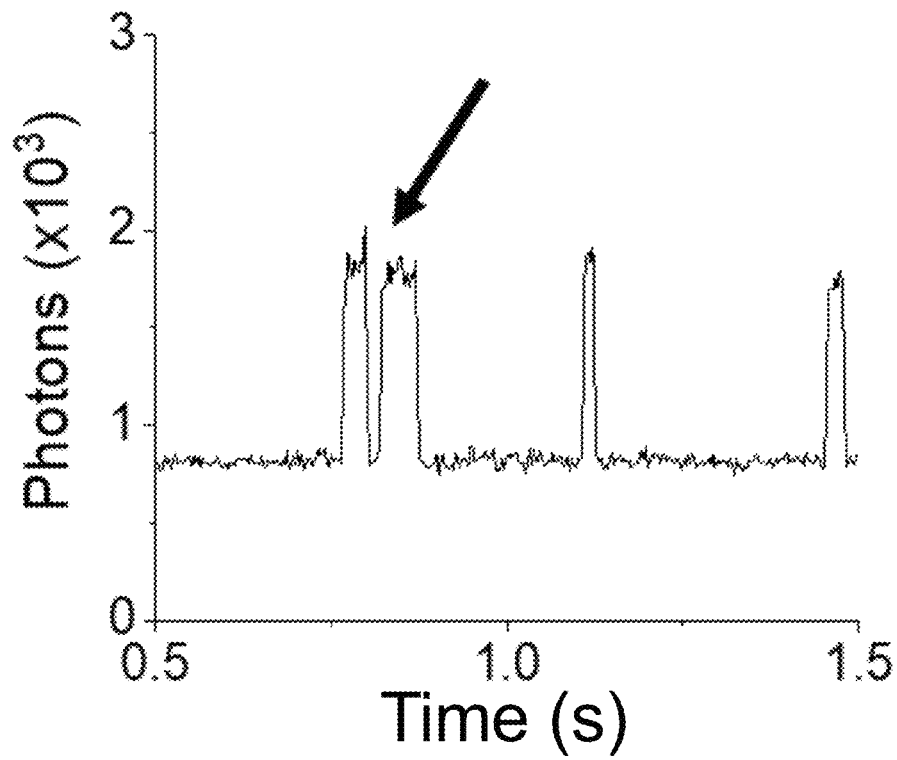

FIGS. 14A-14C show: (FIGS. 14A-14B) fluorescence time traces of early blinking PEG-Cy5-aC' dots with 50 ms integration times; and (FIG. 14C) autocorrelation of fluorescence time trace and single exponential decay fit yielding a $\tau_{off}$ of ~94 ms.

FIGS. 15A-15E show: (FIG. 15A) a fluorescence time trace of PEG-Cy5-aC' dots with low equilibrium duty cycle (50 ms integration times); (FIGS. 15B-15C) individual blinking event in FIG. 15A, box, resolved with different time resolution: (FIG. 15B)) 50 ms integration times; (FIG. 15C) 3 ms integration times (but using 51 ms binning). Working with shorter integration times reveals rapid on-off blinking events in FIG. 15C; and (FIG. 15D-15E) fluorescence time trace of PEG-Cy5-aC' dots (3 ms integration time) exhibiting rapid on-off blinking at the beginning of the collection time. Comparison of results in FIG. 15C and FIG. 15E, arrow, plotted on the same time scale of 1 second, suggests similar photophysics for low equilibrium duty cycle and short-time blinking probes.

Figure 16:
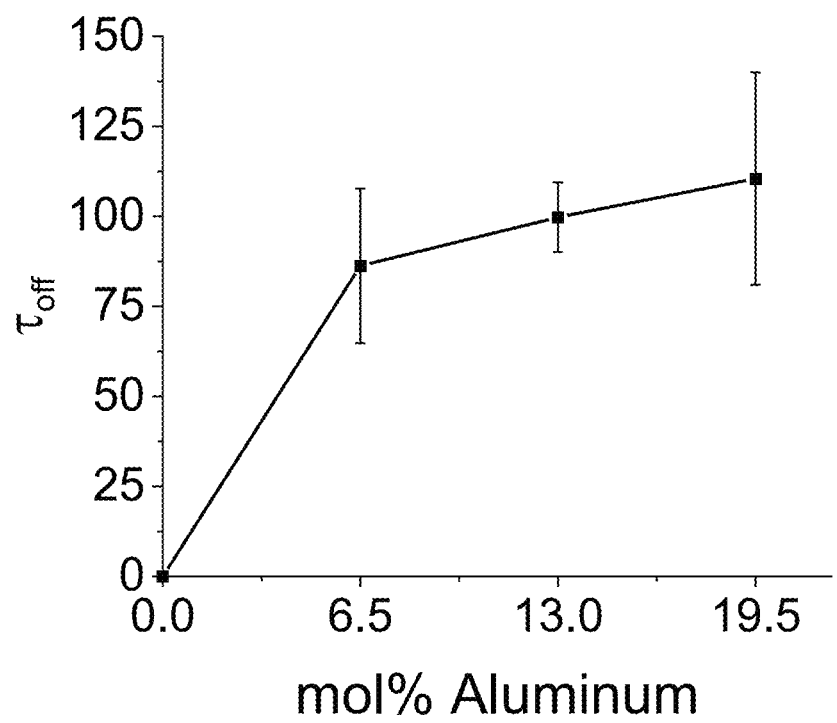
Figure 17A:
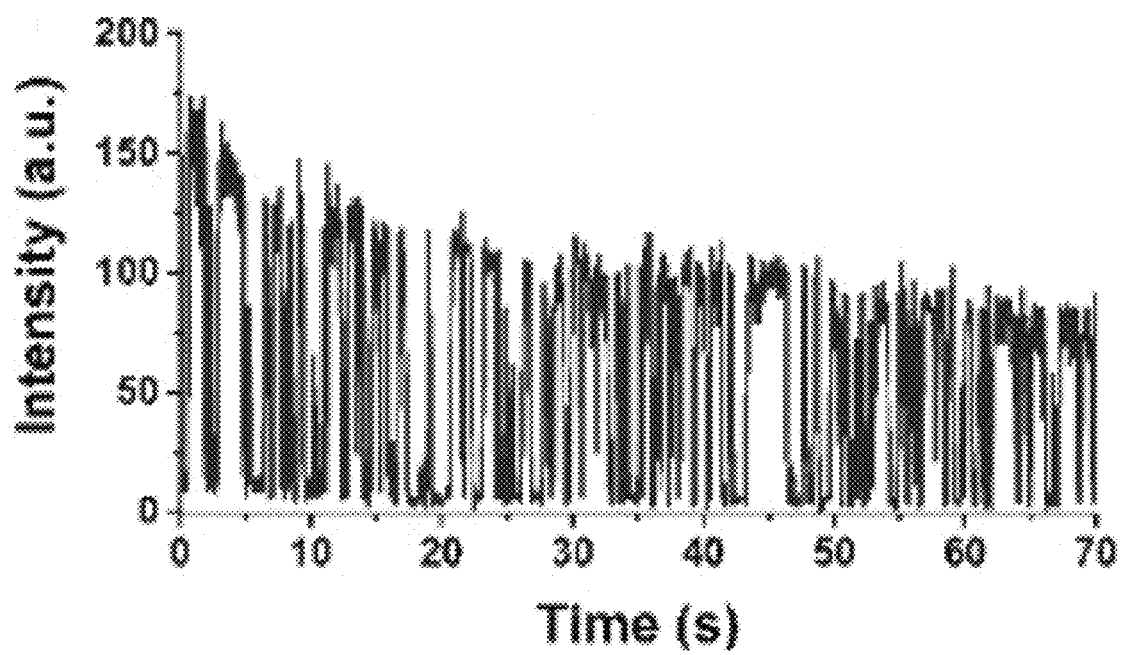
Figure 17B:
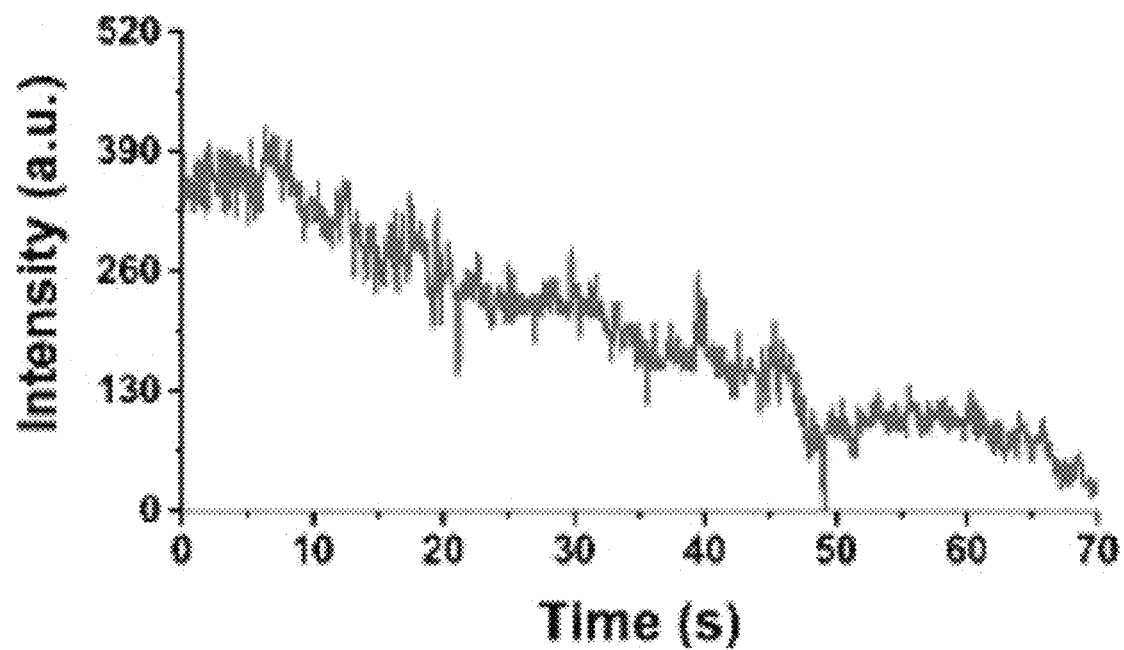
Figure 17C:
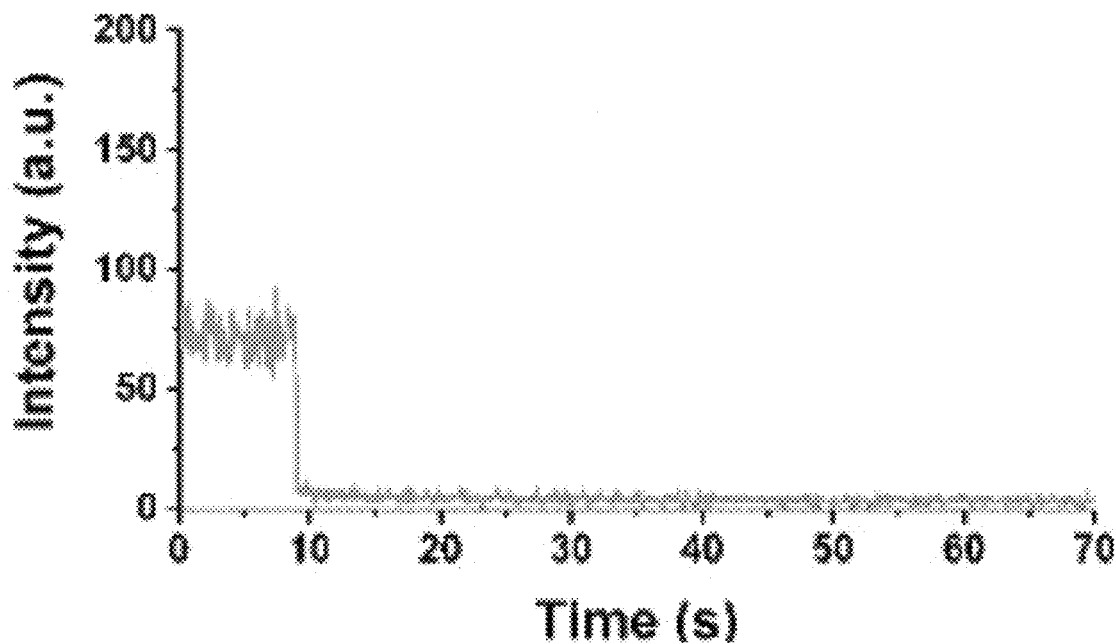
Figure 17D:
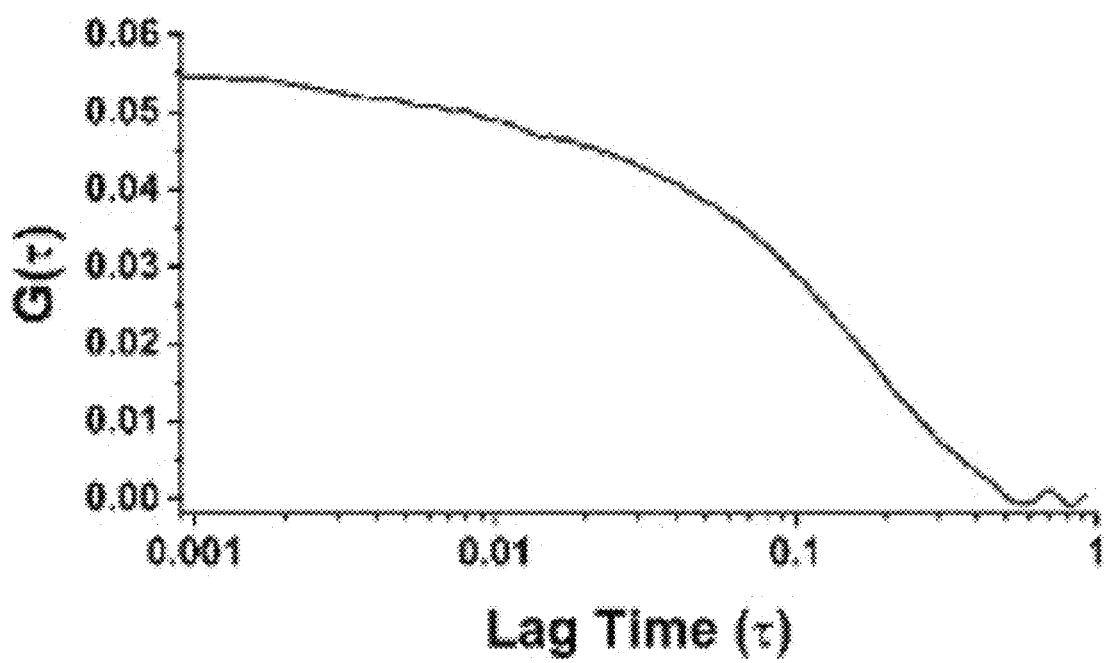
Figure 17E:
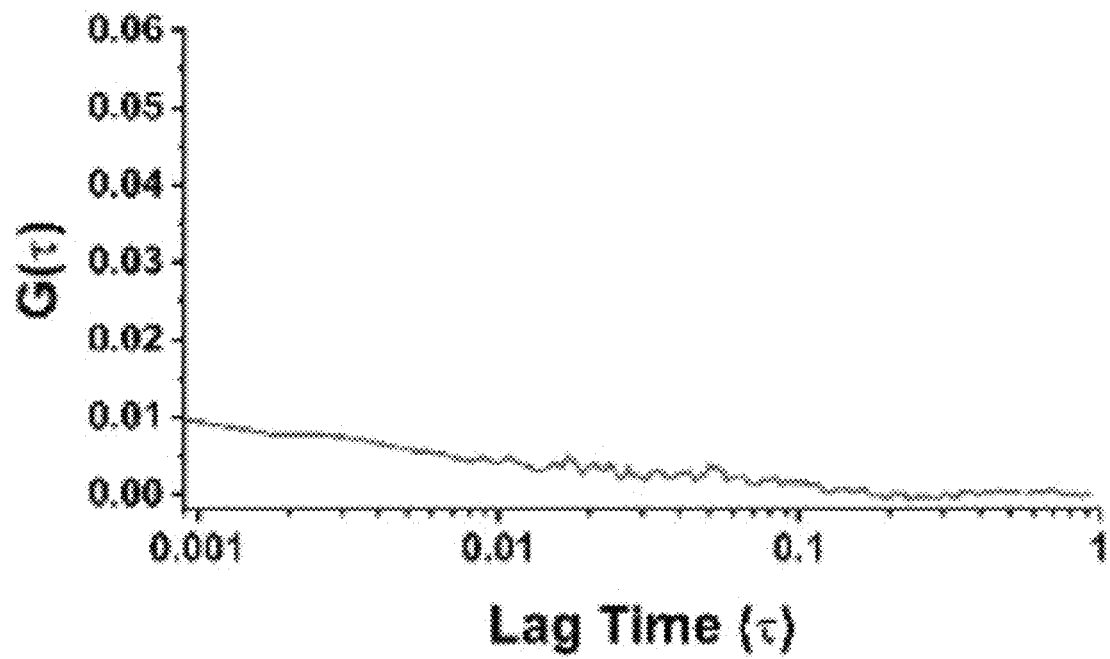
Figure 17F:
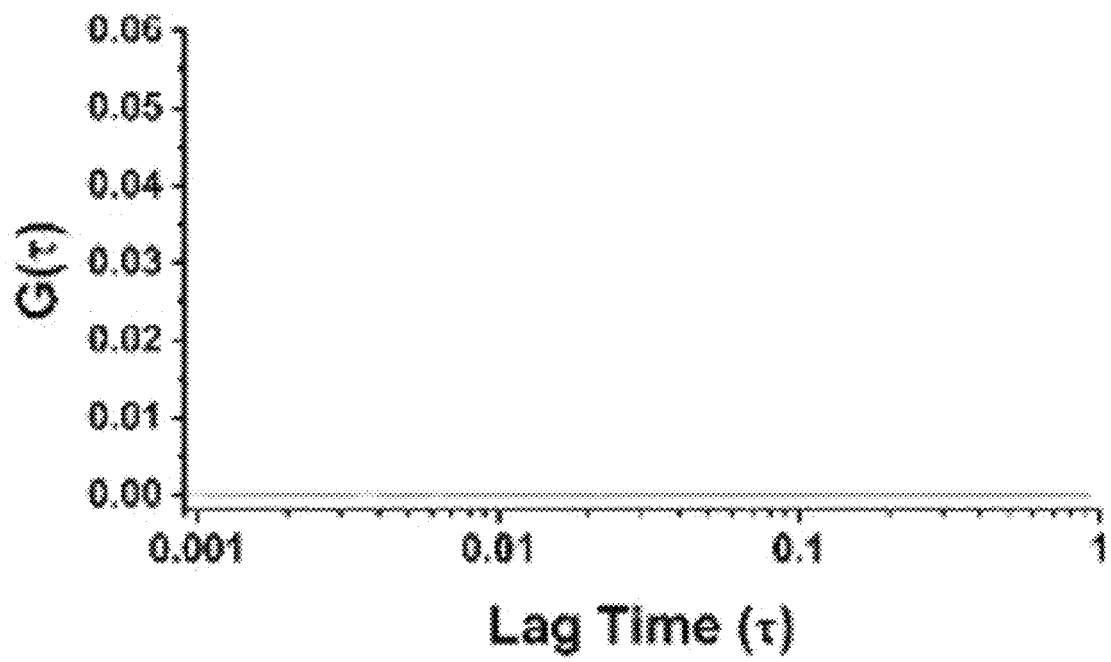
Figure 18A:
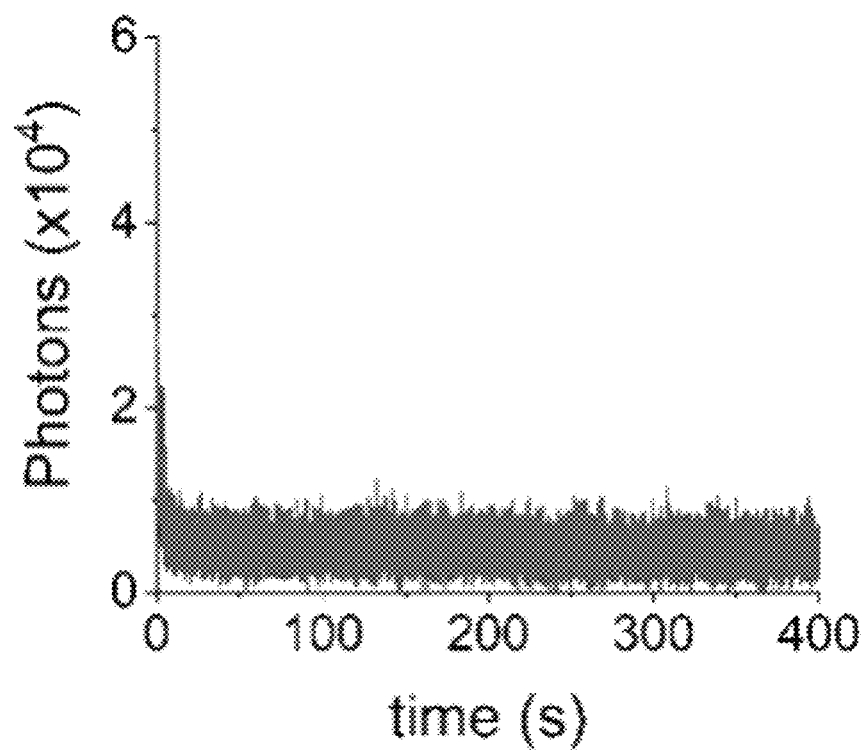
Figure 18B:
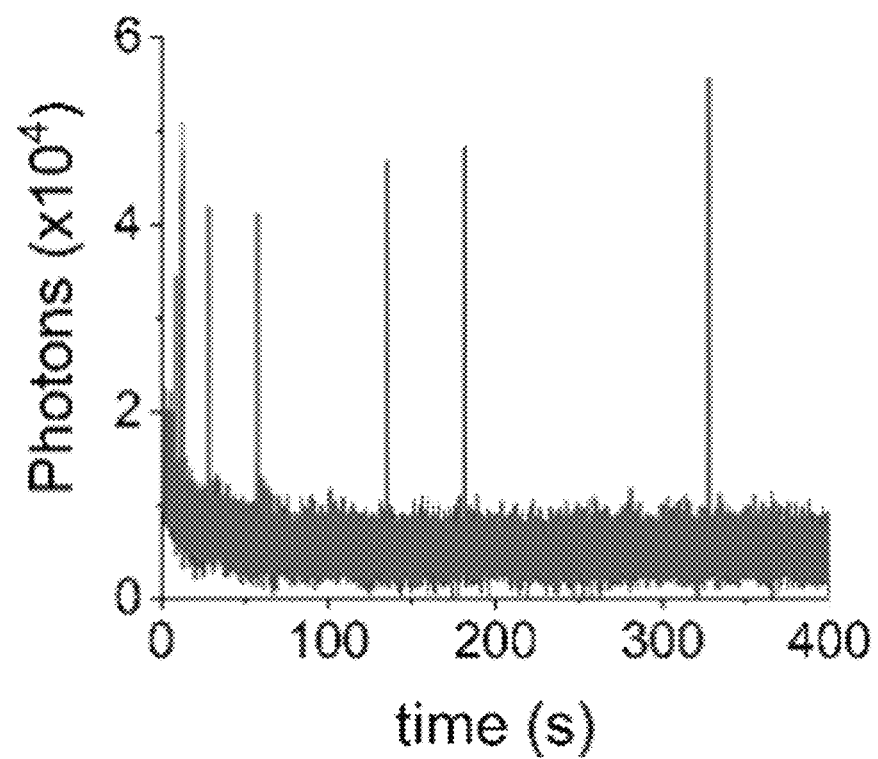
Figure 18C:
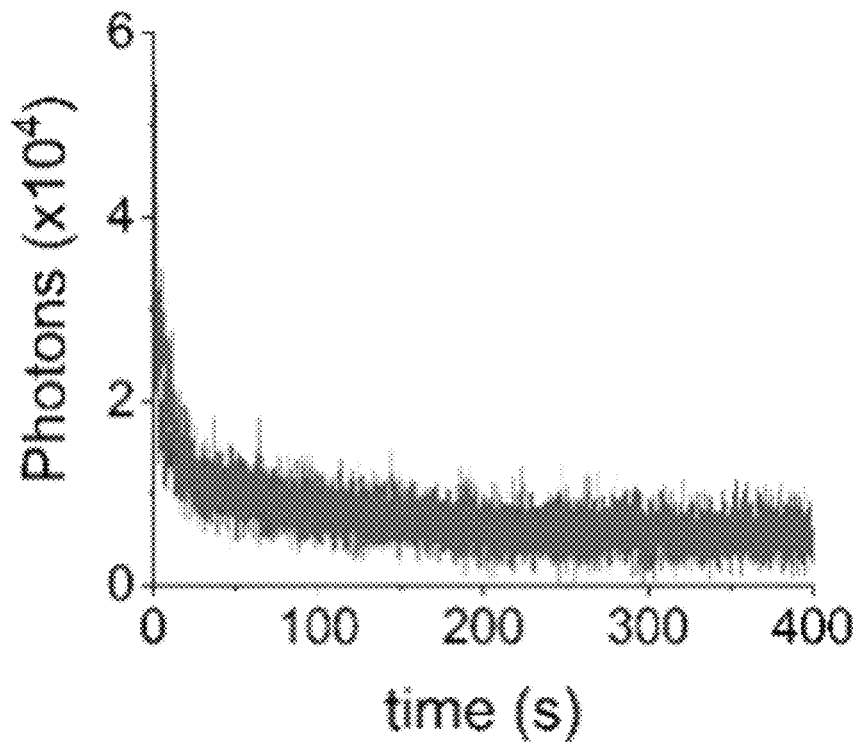
Figure 18D:
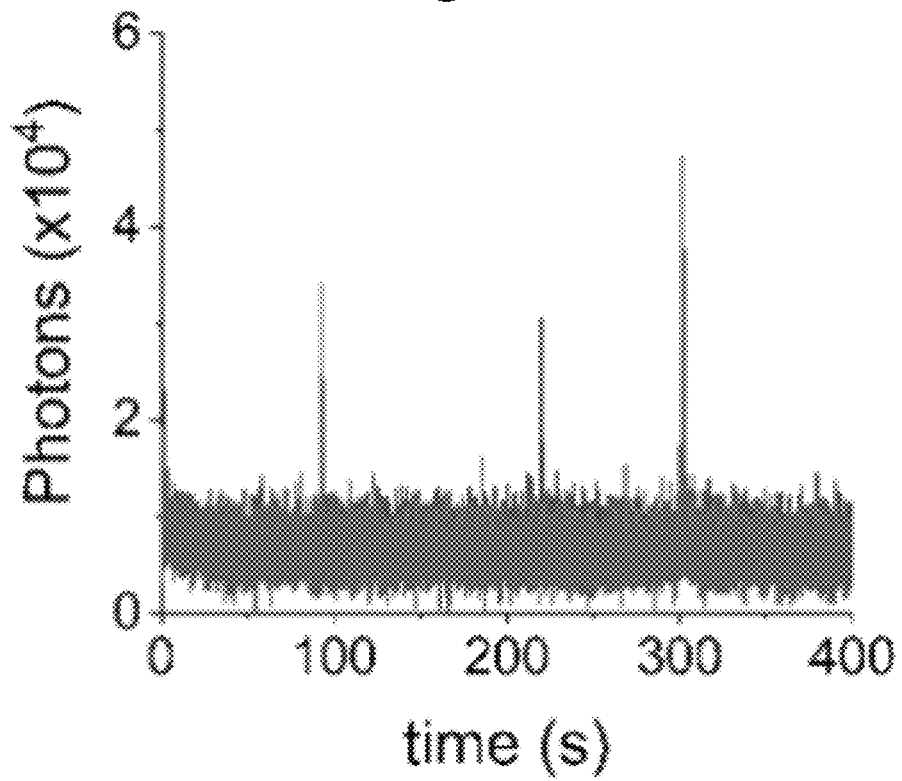
Figure 19A:
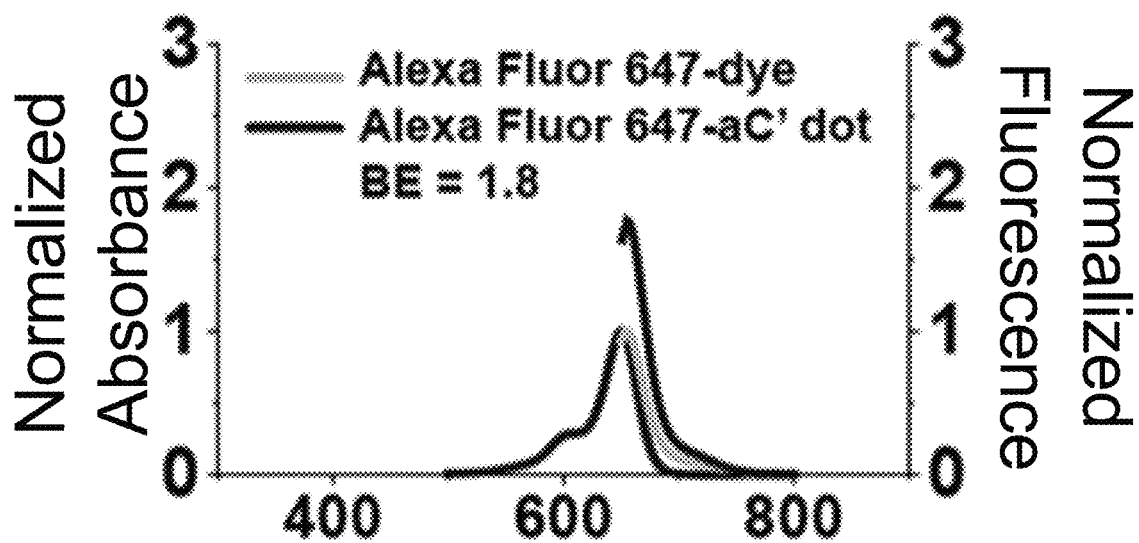
Figure 19B:
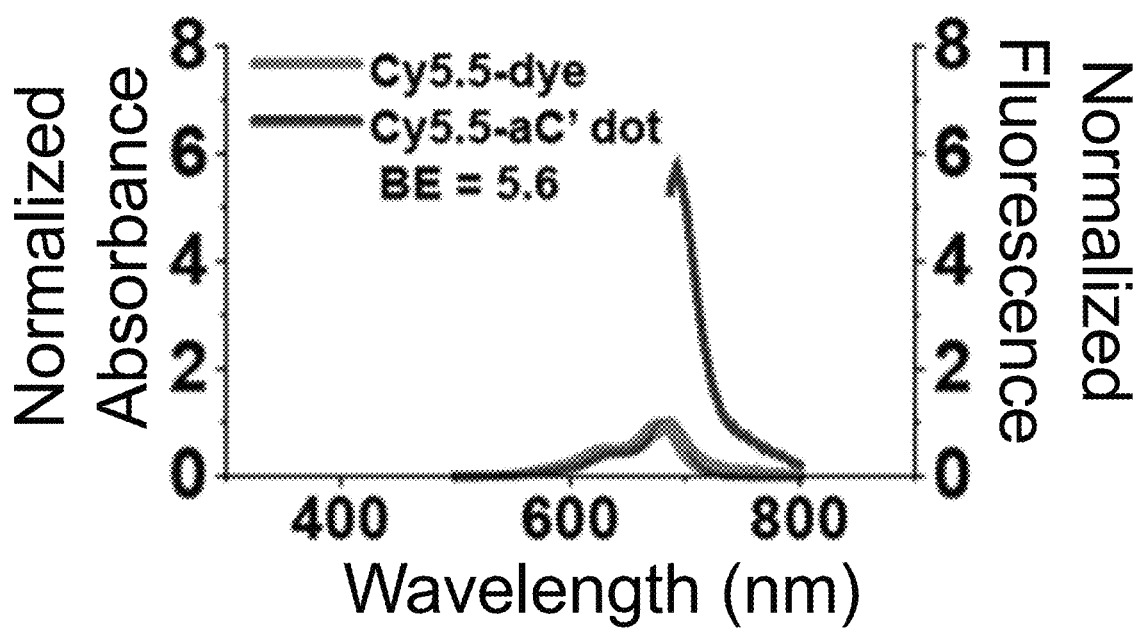
Figure 19C:
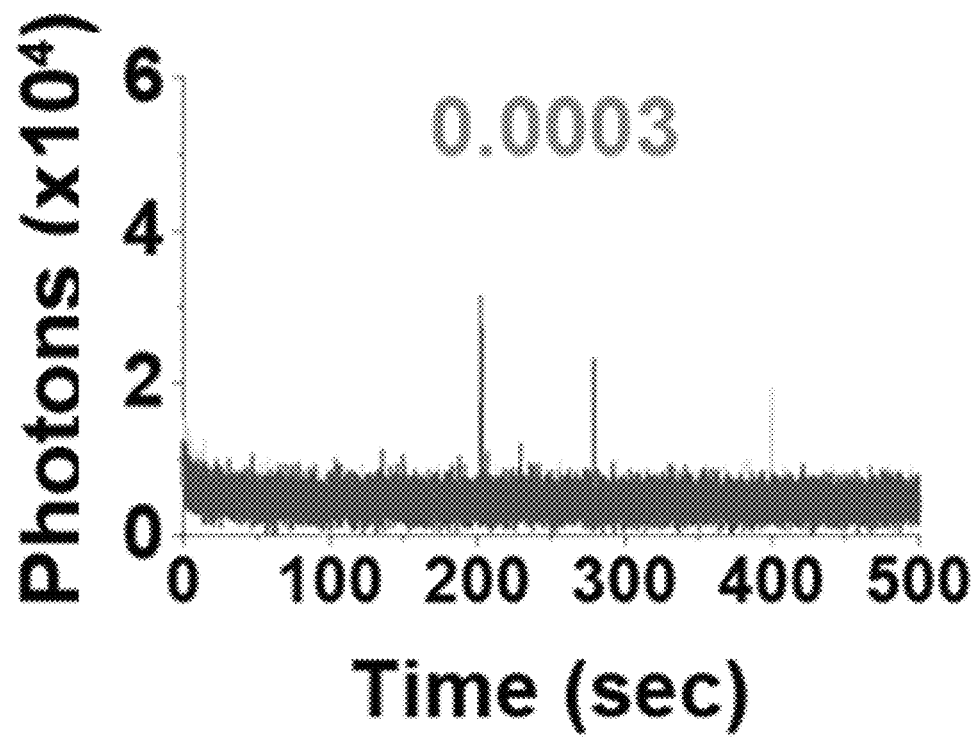
Figure 19D:
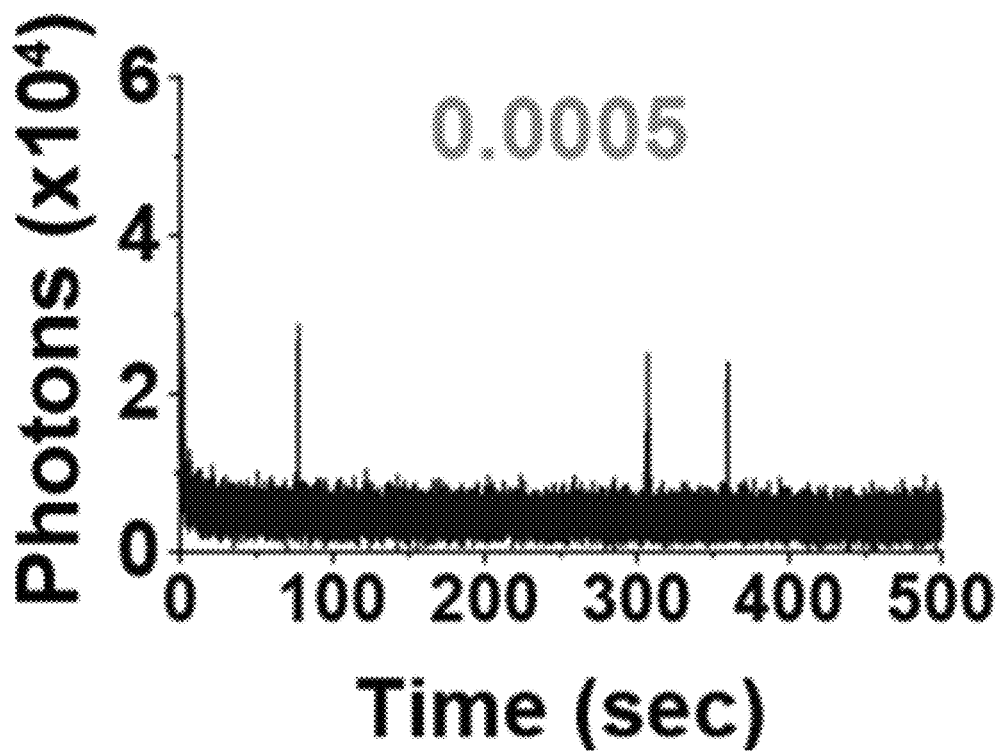
Figure 19E:
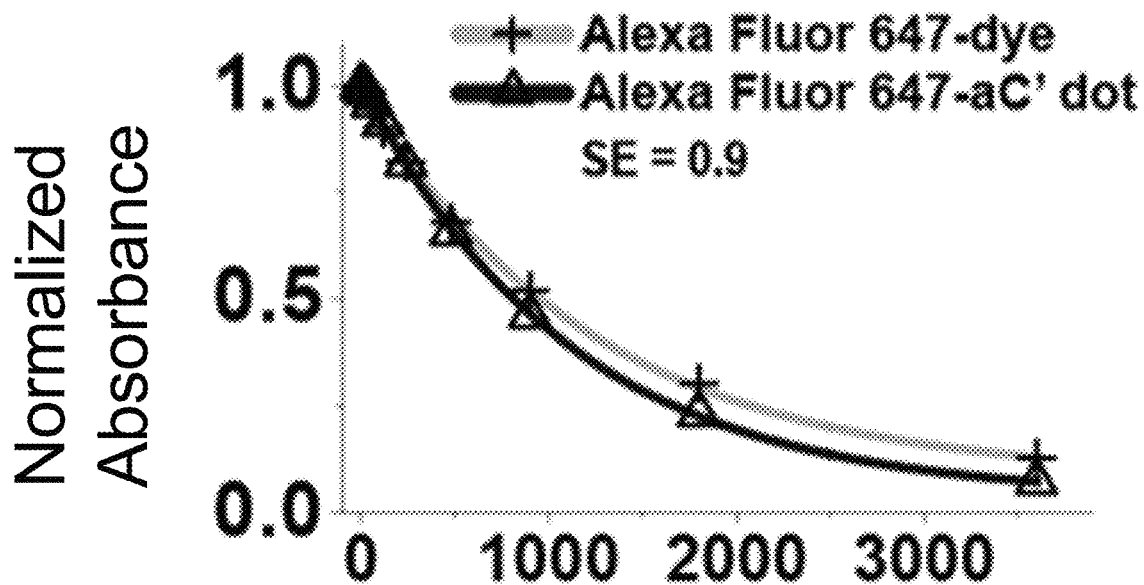
Figure 19F:
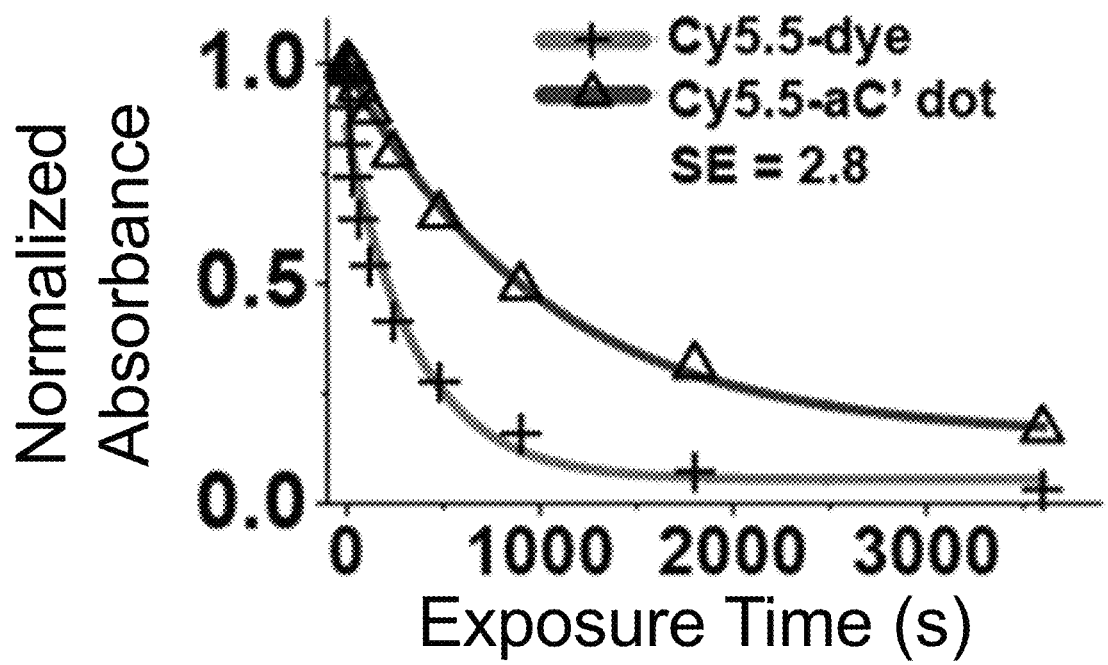

FIG. 16 shows as the mol % of aluminum tri-sec butoxide (ASB) used during the synthesis of PEG-Cy5-aC' dots increased, the average $\tau_{off}$ increased, suggesting that aluminum plays a role in the redox blinking of Cy5. Error bars represent standard error of the mean with n=4.

FIGS. 17A-17F show: fluorescent time traces (1 ms integration time) for (FIG. 17A) Cy5-aC' dot; (FIG. 17B) Cy5-aC' dot with Trolox; and (FIG. 17C) Cy5-C' dot; and (17D-17F) corresponding correlation curves derived from intensity fluctuations in 17A-17C.

FIGS. 18A-18D show single molecule fluorescence traces with 50 ms integration time of Cy5-dye in plain HBSS (FIG. 18A), with sodium aluminate (FIG. 18A), with sodium aluminate+OS system (FIG. 18C), and with sodium aluminate+OS system+methyl viologen (MV) (FIG. 18D), corroborating that dissolved oxygen plays a role in the oxidation of Cy5.

FIGS. 19A-19F show: (FIGS. 19A-19B) normalized and absorbance-matched absorbance (left) and emission (right) spectra in water for PEG-Alexa-Fluor-647-aC' dots and PEG-Cy5.5-aC' dots and their unconjugated free dyes Alexa-Fluor-647 and Cy5.5, respectively; (FIGS. 19C-19D) single-molecule fluorescence traces (50 ms integration time) of immobilized PEG-Alexa-Fluor-647-aC' dots and PEG-Cy5.5-aC' dots. Corresponding equilibrium duty cycles are shown; (FIGS. 19E-19F) photobleaching experiments of parent free dyes and resulting PEG-dye-aC' dots in water with single exponential fits. Poor photostability results for PEG-Alexa-Fluor-647-aC' dots are consistent with incomplete dye encapsulation as a result of high dye charge (net dye charge: negative 3, see Table 1). Particles were all in HBSS imaging buffer for single-particle experiments and exposed to a 640 nm light source. BE: Brightness Enhancement, SE: Stability Enhancement.

Figure 20:
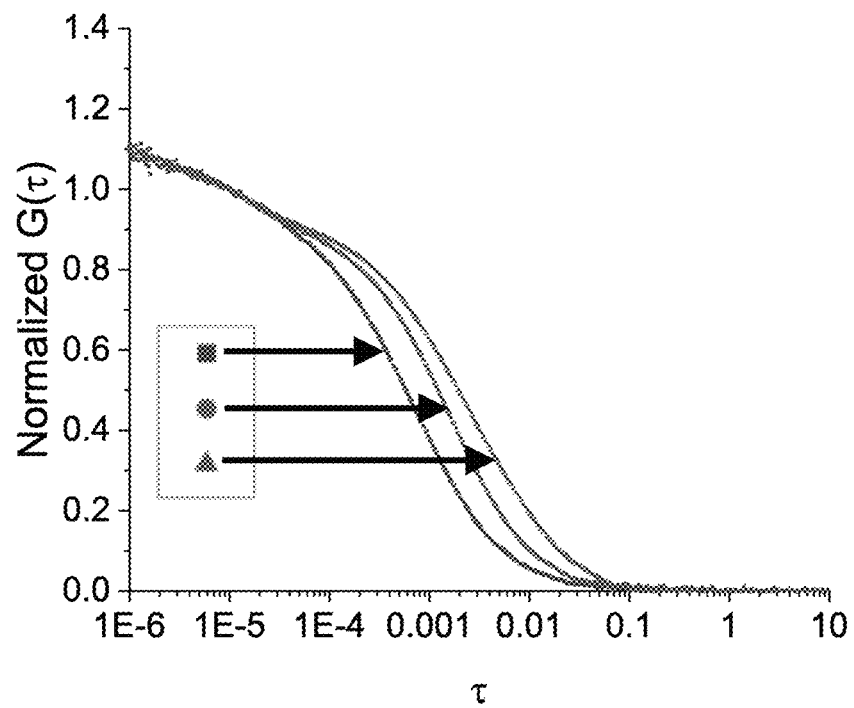

FIG. 20 shows confocal FCS autocorrelation curves for PEG-ATTO647N-aC' dots, $Ab_2$-PEG-ATTO647N-aC' dots, and $Ab_1$-$Ab_2$-PEG-ATTO647N-aC' dots.

Figure 21:
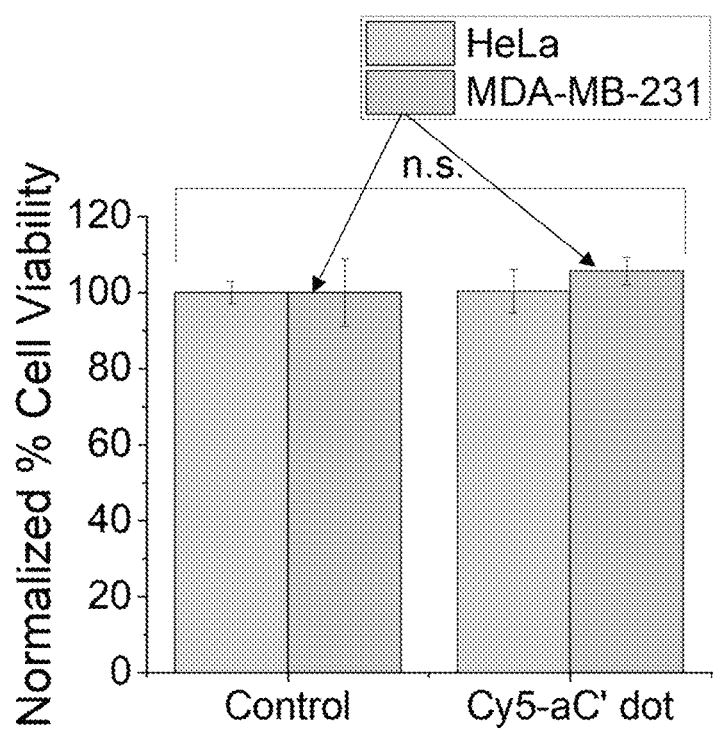

FIG. 21 shows results obtained from a PrestoBlue viability assay showed no statistically significant differences in HeLa or MDA-MB-231 cell viability without and with exposure to 2 μM PEG-Cy5-aC' dots for 24 hours. Results were normalized to samples with no aC' dot exposure. p>0.1 obtained from student's t-test with n=3. Error bars are standard deviation.

Figure 22A:
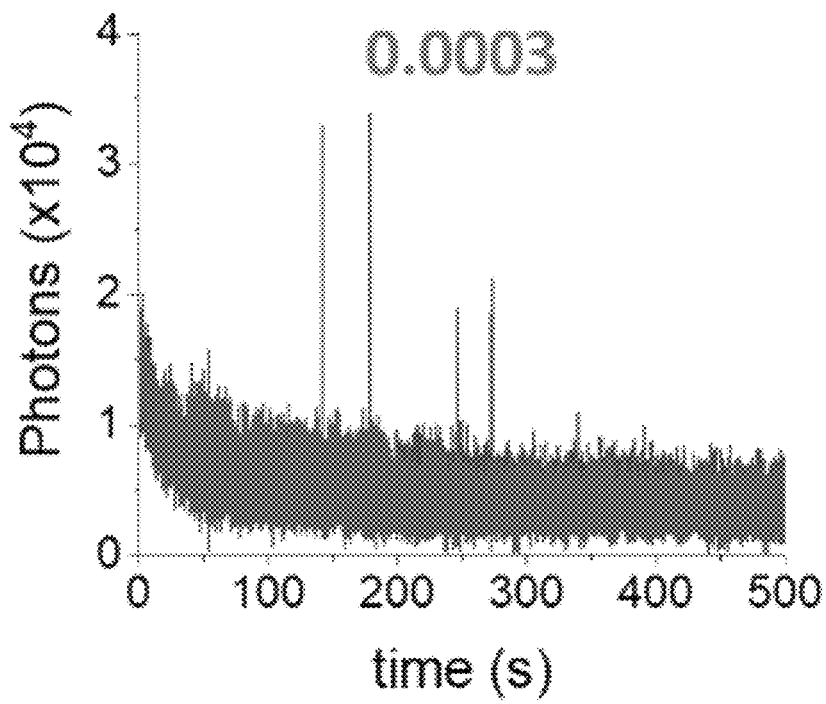
Figure 22B:
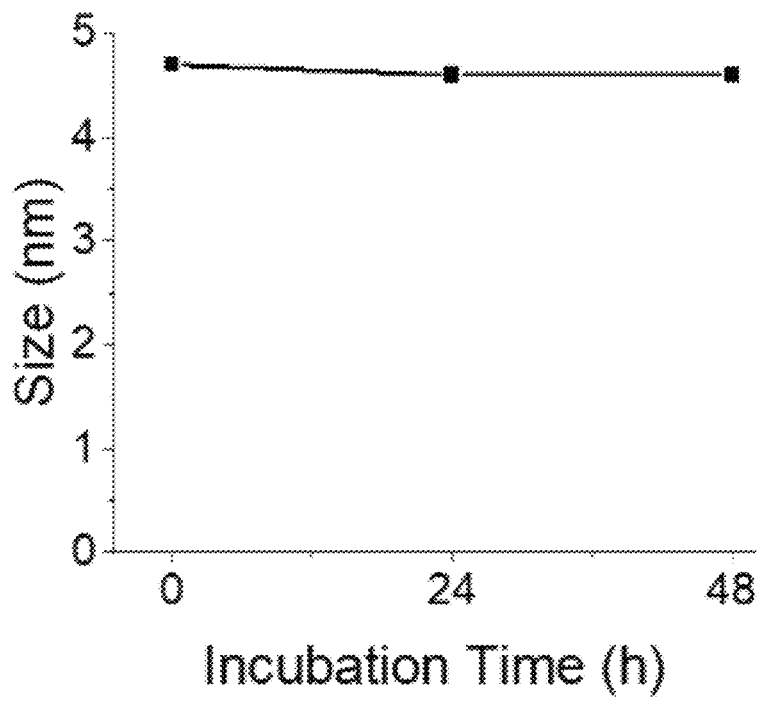

FIGS. 22A-22B show: (FIG. 22A) single-localization fluorescence time traces (50 ms integration time) of PEG-Cy5-aC' dots in the presence of 11 mM glutathione in HBSS with only red laser exposure; and (FIG. 22B) PEG-Cy5-aC' dot size, as determined by FCS, with respect to time incubated in complete RPMI 1640 media at 37° C. suggesting the absence of particle aggregation.

DETAILED DESCRIPTION OF THE DISCLOSURE

Although claimed subject matter will be described in terms of certain examples, other examples, including examples that do not provide all of the benefits and features set forth herein, are also within the scope of this disclosure. Various structural, logical, and process step changes may be made without departing from the scope of the disclosure.

As used herein, unless otherwise stated, "about," "approximately," "substantially," or the like, when used in connection with a measurable variable such as, for example, a parameter, an amount, a temporal duration, or the like, are meant to encompass variations of, for example, a specified value including, for example, those within experimental error (which can be determined by for example, a given data set, an art accepted standard, and/or with a given confidence interval (e.g., 90%, 95%, or more confidence interval from the mean), such as, for example, variations of +/−10% or less, +/−5% or less, +/−1% or less, and +/−0.1% or less of and/or from the specified value), insofar such variations are appropriate to perform in the context of the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error, and the like, and other factors known to those of skill in the art such that, for example, equivalent results, effects, or the like are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Ranges of values are disclosed herein. The ranges set out a lower limit value and an upper limit value. Unless otherwise stated, the ranges include the lower limit value, the upper limit value, and all values between the lower limit value and the upper limit value, including, but not limited to, all values to the magnitude of the smallest value (either the lower limit value or the upper limit value) of a range. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also, unless otherwise stated, include individual values (e.g., about 1%, about 2%, about 3%, and about 4%) and the sub-ranges (e.g., about 0.5% to about 1.1%; about 0.5% to about 2.4%; about 0.5% to about 3.2%, and about 0.5% to about 4.4%, and other possible sub-ranges) within the indicated range. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about, it will be understood that the particular value forms a further disclosure. For example, if the value "about 10" is disclosed, then "10" is also disclosed.

As used herein, unless otherwise stated, the term "group" refers to a chemical entity that is monovalent (i.e., has one terminus that can be covalently bonded to other chemical species), divalent, or polyvalent (i.e., has two or more termini that can be covalently bonded to other chemical species). The term "group" also includes radicals (e.g., monovalent and multivalent, such as, for example, divalent radicals, trivalent radicals, and the like). Illustrative examples of groups include:

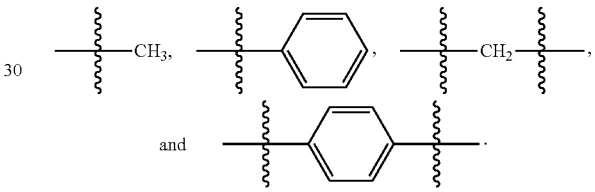

The present disclosure provides imaging methods. The present disclosure also provides compositions and kits comprising aluminosilicate particles.

In an aspect, the present disclosure provides imaging methods. The imaging methods may be optical super-resolution imaging methods. The methods are based on use of aluminosilicate nanoparticles. Non-limiting examples of imaging methods are provided herein.

This disclosure provides, inter alia, methods for imaging biological materials, such as, for example, cells (e.g., living cells, fixed cells, and the like), extracellular components, or tissues comprising contacting a biological material with aluminosilicate nanoparticles of the present disclosure (e.g., aluminosilicate nanoparticles comprising one or more fluorophore(s) (e.g., one or more dye(s) or the like), or compositions comprising the nanoparticles; directing excitation electromagnetic (e/m) radiation, such as light, on to the tissues or cells thereby exciting the fluorophore(s) (e.g., dye molecule(s) or the like); detecting e/m radiation emitted by the excited fluorophore(s) (e.g., dye molecule(s) or the like); and capturing and processing the detected e/m radiation to provide one or more image(s) (which may be optical super-resolution images) of the biological material. One or more step(s) of the method can be carried out in vitro or in vivo. For example, the cells or tissues can be present in (or obtained from) an individual, can be present in culture, or the like. Exposure of cells or tissues to electromagnetic radiation may be affected in vitro (e.g., under culture conditions or the like), may be affected in vivo, or the like. For directing electromagnetic radiation at cells, extracellular materials, tissues, organs, or the like within an individual or any portion of an individual's body that are not easily accessible, fiber optical instruments can be used.

Since the fluorescent aluminosilicate nanoparticles are brighter than free dye, fluorescent particles can be used, for example, for tissue imaging and tumor (e.g., metastatic tumor) imaging. Additionally or alternatively, radioisotopes can be further attached to the ligand groups (e.g., tyrosine residue, chelator, and the like) of the ligand-functionalized nanoparticles or to the aluminosilicate matrix of the PEGylated aluminosilicate nanoparticles without specific ligand functionalization for photoinduced electron transfer imaging. If the radioisotopes are chosen to be therapeutic, such as, for example, $^{225}$Ac or $^{177}$Lu, this in turn would result in nanoparticles with additional radiotherapeutic properties.

An imaging method may be carried out on an individual or a sample from an individual that is diagnosed with or suspected of having cancer. A method may be a screening method (e.g., the individual is or the sample is from an individual that is not currently diagnosed with or suspected of having cancer).

In an example, a method of obtaining an image of a sample comprising a biological material comprises: contacting the sample (e.g., the individual) with one or more aluminosilicate nanoparticle(s) and/or one or more composition(s) of the present disclosure; irradiating the sample (e.g., individual or a portion thereof); and obtaining one or more (e.g., a plurality of) fluorescence image(s) of the sample (e.g., the individual or a portion thereof). The fluorescent image(s) may be used to generate an optical super-resolution image.

In another example, a method for imaging of a region within an individual comprises administering to the individual one or more aluminosilicate nanoparticle(s) and/or one or more composition(s) of the present disclosure; irradiating the individual or a portion thereof with electromagnetic radiation (e.g., directing electromagnetic radiation, which may be referred to as, excitation light into the individual), thereby exciting at least one of the one or more fluorophore(s) (e.g., dye molecule(s) or the like) of the aluminosilicate nanoparticle(s); and obtaining one or more fluorescent image(s) of the region within the individual (e.g., detecting emitted light, the detected light having been emitted by the one or more fluorophore(s) (e.g., dye molecule(s) or the like) in the individual as a result of excitation by the excitation light; and processing signals corresponding to the detected light to provide one or more images (e.g., a real-time video stream), which may be one or more optical super-resolution image(s), of the region within the individual).

Various samples can be used. In various examples, a sample (which may be a biological sample) comprises living or fixed tissues and/or cells or the like. A sample may be a biopsy obtained from an individual (e.g., where the individual is suspected of having cancer or has been diagnosed with cancer).

Contacting a sample or an individual, or a portion thereof, with one or more aluminosilicate nanoparticles(s) and/or one or more composition(s) of the present disclosure can be carried out in various ways. In various examples, the contacting is staining a sample, or a portion thereof, with one or more aluminosilicate nanoparticle(s) and/or one or more composition(s). In various other examples, the contacting comprises administering one or more aluminosilicate nanoparticle(s) and/or one or more composition(s) to an individual.

The irradiation can be carried out in various ways. In various examples, electromagnetic radiation is directed into the individual (e.g., a region of an individual). In various examples, electromagnetic radiation is directed into the individual (e.g., a region of an individual) using a fiber optic source or the like.

Various wavelengths and sources of electromagnetic radiation can be used. In various examples, the electromagnetic radiation comprises one or more wavelength(s) from 400 to 1200 nm, including all nm values and ranges therebetween. In various examples, the electromagnetic radiation is a single wavelength. In various examples, the electromagnetic radiation is monochromatic, a single color, or the like). The source of the electromagnetic radiation may be a laser (e.g., a single laser). Irradiation may be carried out using a single source. In various examples, irradiation is carried out using a laser (e.g., a single laser).

A fluorescent image can be obtained in various ways. For example, obtaining a fluorescence image comprises: detecting electromagnetic radiation (which may be referred to in the alternative as emitted electromagnetic radiation), the detected electromagnetic radiation having been emitted by the fluorophore(s) (e.g., dye molecule(s) or the like) in the individual as a result of excitation by the excitation electromagnetic radiation; and processing signals corresponding to the detected electromagnetic radiation to provide one or more fluorescent image(s) of the region within the individual, which may be used to generate one or more optical super-resolution image(s).

In an example, a method comprises obtaining a plurality of fluorescence images (e.g., about 1000 images, which may be referred to individually as frames or in the aggregate as a set), analyzing each individual frame (e.g., by localizing individual blinking events applying the point-spread function (PSF), or the like, and/or summing up over all frames and localization events to generate a super-resolution image.

Imaging methods of the present disclosure can provide sub-diffraction limit resolution. The imaging methods can be referred to as super-resolution (SR) imaging methods. In various examples, an imaging method provides (e.g., exhibits) sub-diffraction limit resolution, where the diffraction limit is $\lambda/2$ and $\lambda$ is the wavelength of the excitation light. In various examples, an imaging method provides (e.g., exhibits) a resolution 10% or less, 20% or less, or 50% or less than the diffraction limit.

Use of the one or more aluminosilicate nanoparticle(s) and/or composition(s) of the present disclosure do/does not require reducing agents and/or oxidizing agents as additives to an imaging buffer to provide sub-diffraction limit resolution. Accordingly, in an example, a composition used in an imaging method does not comprise an imaging buffer (e.g., an imaging buffer comprising a reducing agent or an oxidizing agent). Examples of imaging buffers are known in the art. Non-limiting examples of imaging buffers include a mixture of 2-mercaptoethanol and enzymatic oxygen scavenger system (e.g., glucose oxidase/catalase system) in phosphate-buffered saline (PBS). In an example, a composition used in an imaging method of the present disclosure does not comprise 2-mercaptoethanol or the like.

Various optical super-resolution imaging methods can be carried out using methods of the present disclosure. Examples of optical super-resolution imaging methods are known in the art. Non-limiting examples of optical super-resolution imaging methods include ground state depletion (GSD) microscopy, stochastic optical reconstruction microscopy (STORM), direct stochastic optical reconstruction microscopy (dSTORM), stimulated emission and depletion (STED), photoactivated localization microscopy (PALM), and the like.

Aluminosilicate nanoparticle(s) and/or composition(s) comprising aluminosilicate nanoparticles can be administered to an individual by any suitable route—either alone or as in combination with other agents. Administration can be accomplished by any means, such as, for example, by parenteral, mucosal, pulmonary, topical, catheter-based, oral means of delivery, or the like. Parenteral delivery can include, for example, subcutaneous, intravenous, intramuscular, intra-arterial, injection into the tissue of an organ, or the like. Mucosal delivery can include, for example, intranasal delivery or the like. Pulmonary delivery can include inhalation of the agent or the like. Catheter-based delivery can include delivery by iontophoretic catheter-based delivery or the like. Oral delivery can include delivery of an enteric coated pill, administration of a liquid by mouth, or the like. Transdermal delivery can include delivery via the use of dermal patches or the like.

Following administration of aluminosilicate nanoparticles or a composition comprising the aluminosilicate nanoparticles, the path, location, clearance of the aluminosilicate nanoparticles, or the like, or a combination thereof may be monitored using one or more imaging technique(s) of the present disclosure. In various examples, the spatial and/or temporal distribution of the nanoparticles in a sample or one or more portion(s) thereof is determined.

In as aspect, the present disclosure provides methods of treatment. A method of the present disclosure can be used to treat an individual with (e.g., diagnosed with or suspected of having) cancer. Non-limiting examples of methods of treatment are provided herein.

In various examples, a method of treating an individual for cancer comprises: obtaining an image of a sample (e.g., a biological material) or a portion thereof or an individual or a portion thereof. A method may further comprise any treatments (e.g., one or more additional step) typically used in treatment of cancer. The individual treatment(s) (e.g., the one or more additional step(s)) may be carried out before and/or after and/or during obtaining the image. In various examples, a method further comprises one or more chemotherapy treatment(s), one or more radiation treatment(s), one or more photodynamic therapy treatment(s), one or more surgical intervention(s) (e.g., surgical procedure(s), or the like), or the like, or any combination thereof. In various examples, the sample is a biopsy obtained from an individual (which may have been diagnosed with cancer or may be suspected of having cancer).

At least a portion of or all of the aluminosilicate nanoparticles may be therapeutic (e.g., comprise a therapeutic agent (e.g., a drug, such as, for example, a chemotherapeutic drug, an immunotherapeutic drug, and the like, and combinations thereof, a radioisotope, and the like, and combinations thereof). Accordingly, in various examples, administration of the aluminosilicate nanoparticles in a method of imaging provides a therapeutic effect (e.g., cancer treatment).

The treatment can have various results. In various examples, a method of the present disclosure results in at least one or more of the following: complete cure of the individual, remission, increased long-term survival of the individual, reduced tumor volume, or the like.

In various examples, a method further comprises subjecting (e.g., administering or the like) to the individual one or more additional cancer treatment(s). In various examples, the additional cancer treatment is chosen from surgery, radiotherapy, chemotherapy, toxin therapy, immunotherapy, cryotherapy, gene therapy, and any combination thereof.

Various chemotherapy agents (e.g., chemotherapy drugs) can be used. Any FDA approved chemotherapy agent (e.g., chemotherapy drugs) can be used. Combinations of chemotherapy agents can be used.

The administrations and irradiation can be carried out in various ways and in various orders. Typically, administration(s) of the aluminosilicate nanoparticle(s) or composition(s) is/are carried out first, and, subsequently, the chemotherapy agent(s) is/are is administered. The irradiation may be carried out after administration of the nanoparticle(s) or composition(s) and before administration of the chemotherapy agent(s) or after administration of both the nanoparticle(s) or composition(s) and chemotherapy agent(s). In an example, the administration comprises i) administration of the nanoparticle(s) and/or composition(s), and ii) after completion of the administration of the nanoparticle(s) and/or composition(s) and irradiation of the individual, administration of the chemotherapy agent.

In an example, the chemotherapy agent is administered (e.g., administration initiated) after administration (e.g., first administration) of the aluminosilicate nanoparticle(s) or composition(s) or after administration (e.g., a first administration) of the nanoparticle(s) or composition(s) and irradiation.

A method may also comprise visualization of the abnormal cells (e.g., cancer cells) (e.g., visualization of one or more tumor(s)) after administration of the aluminosilicate nanoparticle(s) or composition(s) of the present disclosure. The visualization (e.g., optical super-resolution imaging) can be used to determine personalized treatment for an individual. For example, visualization is carried using optical super-resolution imaging (e.g., optical super-resolution imaging of the present disclosure). A method may further comprise further comprise surgical intervention (e.g., surgical removal of at least a portion of or all of a cancerous tissue from the individual). The surgical removal can be guided by the visualization (e.g., optical super-resolution imaging).

Methods of the present disclosure can be used to treat various cancers (e.g., a tumor or tumors related to a cancer). Non-limiting examples of cancers include lung cancer, colon cancer, melanoma, head and/or neck cancer, esophageal cancer, laryngeal cancer, breast cancer, pancreatic cancer, renal cancer, bladder cancer, ovarian cancer, prostate cancer, testicular cancer, and the like, and any combination thereof.

Methods of the present disclosure can be used on various individuals. An individual may or may not have been diagnosed with cancer or may or may not be suspected of having cancer. In various examples, an individual is a human or non-human mammal. Examples of non-human mammals include, but are not limited to, farm animals, such as, for example, cows, hogs, sheep, and the like, as well as pet or sport animals such as horses, dogs, cats, and the like. Additional non-limiting examples of individuals include rabbits, rats, mice, and the like. The aluminosilicate nanoparticles or compositions comprising nanoparticles can be administered to individuals for example, in pharmaceutically acceptable carriers, which facilitate transporting the nanoparticles from one organ or portion of the body to another organ or portion of the body.

Various aluminosilicate nanoparticles can be used. The aluminosilicate nanoparticles (or the aluminosilicate nanoparticles in a composition) may be a combination of different nanoparticles. All of the aluminosilicate nanoparticles (or the aluminosilicate nanoparticles in a composition) may be the same. In various examples, all of the aluminosilicate nanoparticles (or the aluminosilicate nanoparticles in a composition) comprise the same fluorophore(s). Two or more or all of the nanoparticles (or two or more of the aluminosilicate nanoparticles in a composition) may be different in terms of one or more or all of size, fluorophore composition (e.g., dye composition or the like), number of fluorophores (e.g., dyes or the like), or the like.

An aluminosilicate nanoparticle can comprise various amounts of aluminum. In various examples, a portion of or all of the aluminosilicate nanoparticles comprises 0.01-20 mol % (e.g., 5-20 mol %) aluminum (relative to silicon (e.g., based on the total moles of aluminum and silicon)), including all 0.01 mol % values and ranges therebetween. In various examples, the amounts of aluminum and/or silicon in an aluminum silicate nanoparticle or aluminum silicate nanoparticles correlates to the amount of aluminum precursor(s) and/or silicon precursor(s) used to form the nanoparticle(s). In various examples, the amounts of aluminum and/or silicon in an aluminum silicate nanoparticle or aluminum silicate nanoparticles is determined by or using energy-dispersive X-ray spectroscopy (EDS).

Non-limiting examples of aluminosilicate nanoparticles are known in the art. Non-limiting examples of suitable aluminosilicate nanoparticles and methods of making same as well as functionalizing their surfaces are described in International Patent Application No. PCT/US16/30752 (titled "Ultrasmall Nanoparticles and Methods of Making and Using Same"; and published as International Patent Application Publication No. WO 2016/179260 on Nov. 10, 2016), the disclosure of which with regard to aluminosilicate nanoparticles and methods of making same are incorporated herein by reference.

Without intending to be bound by any particular theory, it is considered that the aluminosilicate nanoparticles exhibit blinking such that optical super-resolution microscopy images can be obtained from a sample or individual. In various examples, the aluminosilicate nanoparticle or at least a portion of or all of the aluminosilicate nanoparticles exhibit blinking behavior (e.g., as determined by the duty cycle or the like).

It may be desirable that at least a portion of or all of the aluminosilicate nanoparticles exhibit a low duty cycle (time emitter is on/data acquisition time). In various examples, at least a portion of or all of the aluminosilicate nanoparticles exhibit a duty cycle of less than 0.001 or less 0.0005.

An aluminosilicate nanoparticle can comprise various fluorophores. A fluorophore may be a molecule or a group. In various examples, a fluorophore is a dye (which may be referred to in the alternative as a fluorescent dye) or the like. In various examples, a dye is an organic dye. In an example, a fluorophore (which may be a dye) does not comprise a metal atom. A nanoparticle may comprise a mixture of fluorophores (e.g., dyes or the like). Non-limiting examples of fluorophores (which may be dyes) include fluorescent dyes, fluorescent proteins (e.g., EBFP2 (variant of blue fluorescent protein), mCFP (Cyan fluorescent protein), GFP (green fluorescent protein), mCherry (variant of red fluorescent protein), iRFP720 (Near Infra-Red fluorescent protein)), groups derived therefrom, and the like, and combinations thereof. In various examples, a fluorophore (e.g., a dye or the like) absorbs in the UV-visible portion of the electromagnetic spectrum. In various examples, a fluorophore (e.g., a dye or the like) has an excitation and/or emission in the near-infrared portion of the electromagnetic spectrum (e.g., 650-900 nm).

Non-limiting examples of organic dyes include cyanine dyes (e.g., Cy5®, Cy3®, Cy5.5®, Cy7®, and the like), carborhodamine dyes (e.g., ATTO 647N (available from ATTO-TEC and Sigma Aldrich®), BODIPY dyes (e.g., BODIPY 650/665 and the like), xanthene dyes (e.g., fluorescein dyes such as, for example, FITC, Rose Bengal, and the like), eosins (e.g., Eosin Y and the like), and rhodamines (e.g., TAMRA, TMR, TRITC, DyLight® 633, Alexa 633, HiLyte 594), methylene blue, Acridine Orange, groups derived therefrom, and the like, and combinations thereof.

An aluminosilicate nanoparticle may comprise a group derived from a fluorophore (e.g., a fluorescent molecule (such as, for example, a dye molecule or the like)). For example, fluorescent molecule (e.g., a dye molecule or the like) or a derivative of a fluorescent molecule (e.g., a dye molecule or the like) is covalently bonded to the network of a nanoparticle (e.g., via a linker group, which may be a group of a dye precursor). The resulting covalently bonded fluorophore group (e.g., dye group or the like) is derived from the original fluorescent molecule (e.g., dye molecule or the like). Illustrative, non-limiting examples of groups derived from a fluorescent molecule (e.g., a dye molecule or the like) are described herein. In an example, a fluorophore (e.g., a dye or the like) is incorporated into the aluminosilicate network using a fluorophore precursor (e.g., dye precursor or the like) that comprises a fluorophore (e.g., dye or the like) conjugated to a sol-gel silica precursor (e.g., a —Si(OR)$_3$ group, where R is an alkyl group).

A fluorophore molecule/group can be encapsulated in or by the aluminosilicate matrix (or aluminosilicate network). In various examples, at least a portion of or all of the fluorophore(s) of an aluminosilicate nanoparticle is/are independently partially or completely encapsulated by the aluminosilicate matrix (or aluminosilicate network) of the aluminosilicate nanoparticle.

A fluorophore molecule/group (e.g., a dye molecule/group, such as, for example, an organic dye molecule/group or the like) may be a net positively-charged fluorophore molecule/group (e.g., a net positively-charged dye molecule/group, such as, for example, a net positively-charged organic dye molecule/group or the like), a net negatively-charged fluorophore molecule/group (e.g., a net negatively-charged dye molecule/group, such as, for example, a net negatively-charged organic dye molecule/group or the like), or a net neutral (non-charged) fluorophore molecule/group (e.g., a net neutral dye molecule/group, such as, for example, a net neutral organic dye molecule/group or the like). It may be desirable that at least a portion or all of the fluorophore molecule(s)/group(s) (e.g., dye molecule(s)/group(s), such as, for example, organic dye molecule(s)/group(s) or the like) be net positively-charged fluorophore molecule(s)/group(s) (e.g., net positively-charged dye molecule(s)/group(s), such as, for example, net positively-charged organic dye molecule(s)/group(s) or the like).

The fluorophores (e.g., dyes or the like) can be conjugated to an aluminosilicate nanoparticle via various groups. The groups conjugating a fluorophore (e.g., a dye or the like) to a nanoparticle may be part of (e.g., a group of) a fluorophore precursor (e.g., dye precursor or the like) used in the synthesis of the nanoparticle. In various examples, the fluorophores (e.g., dyes or the like) are conjugates via amino-silanes and active ester groups on the dye. In various examples, the fluorophores (e.g., dyes or the like) are not conjugated via mercapto-silanes and maleimido groups on the dye.

An aluminosilicate nanoparticle can have various amounts of fluorophore (e.g., dye or the like). Without intending to be bound by any particular theory, it is considered that the number of fluorophores (e.g., dyes or the like) present in a nanoparticle correlates to the amount of fluorophore precursor (e.g., dye precursor or the like) used in the synthesis of the nanoparticle. As an illustrative example, for particles having a size below 10 nm, such particles typically have, on average, 1-5 fluorophore(s) (e.g., dye(s) or the like) per nanoparticle. In various examples, a nanoparticle comprises 1 or 2 fluorophore(s) (e.g., dye(s) or the like).

The number of fluorophores (e.g., dyes or the like) per aluminosilicate nanoparticle can be determined by methods known in the art. For example, the number of fluorophores (e.g., dyes or the like) per nanoparticle is determined using a combination of fluorescence correlation spectroscopy (FCS), which provides the number of particles in solution (i.e., the particle concentration), and absorption spectroscopy on the particles, which provides the number of fluorophores (e.g., dyes or the like) in the solution. Dividing the second number by the first gives you the number of fluorophores (e.g., dyes or the like) per particle.

An aluminosilicate nanoparticle can have various sizes. The size of a nanoparticle may be a longest dimension of the nanoparticle. A size may be a hydrodynamic radius/radii and/or hydrodynamic diameter/diameters. The nanoparticles may have a size (e.g., a longest dimension such as, for example, a diameter) of 30 nm or less (e.g., 10 nm or less). For example, a nanoparticle has a size of 1-30 nm, including all 0.1 nm values and range therebetween. In various examples, a nanoparticle has a size of 1-10 nm, including all 0.01 nm values and ranges therebetween. In various examples, the nanoparticles have a size of 1, 1.5, 2, 2.5, 3, 3.5, 4, 4.5, 5, 5.5, 6, 6.5, 7, 7.5, 8, 8.5, 9, 9.5, or 10 nm. In various examples, at least 90%, 95%, 96%, 97%, 98%, 99%, 99.5% 99.9%, or 100% of the nanoparticles have a size of 30 nm or less (e.g., 1-30 nm), 10 nm or less (e.g., 0.1 to 10 nm, including all 0.01 nm values and ranges therebetween). For the exemplary size distributions, the composition may not be subjected to any particle-size discriminating (particle size selection/removal) processes (e.g., filtration, dialysis, chromatography (e.g., GPC), centrifugation, etc.).

It may be desirable to use nanoparticles (or a composition comprising nanoparticles) that are cleared by the kidneys of an individual (e.g., less than about 6 nm). The size of a nanoparticle can be determined by methods known in the art. In various examples, nanoparticle size (or the size (e.g., size distribution) of nanoparticles in a composition) is determined by FCS and/or dynamic light scattering (DLS).

An aluminosilicate nanoparticle may have polyethylene glycol (PEG) group(s), which may form (or be a part of) a portion of a larger (e.g., more complex) group (e.g., a group comprising a ligand or the like), disposed on (e.g., covalently bonded to) a surface (which may be an exterior surface) of the nanoparticle. The chain length of the PEG group(s) (i.e., the molecular weight of the PEG group(s)) can be tuned from 3 to 24 ethylene glycol monomers (e.g., 3 to 6, 3 to 9, 6 to 9, 8 to 12, or 8 to 24 ethylene glycol monomers (3, 4, 5, 6, 7, 8, 9, 10, 11, 12, 13, 14, 15, 16, 17, 18, 19, 20, 21, 22, 23, or 24))). The PEG group(s) chain length(s) can be selected to tune the thickness of the PEG layer surrounding the particle and the pharmaceutical kinetics profiles of the PEGylated particles. The PEG group chain length of ligand-functionalized PEG group be used to tune the accessibility of the ligand groups on the surface of the PEG layer of the particles resulting in varying binding and targeting performance.

In an example, at least a portion of the exterior surface (e.g., at least 20%, 30%, 40%, or 50% of the exterior surface) of an aluminosilicate nanoparticle is functionalized with polyethylene glycol groups. In various examples, the number of PEG group(s) disposed on the surface of a nanoparticle is 3 to 600, including all integer number of PEG group(s) and ranges therebetween.

An aluminosilicate nanoparticle may comprise a ligand or ligands disposed on (e.g., covalently bonded to) a surface of the nanoparticle. A nanoparticle may have two or more different ligands disposed on a surface. A ligand can be conjugated to (e.g., covalently bonded to) a surface of a nanoparticle. Suitable ligand conjugation methods are known in the art.

At least a portion of an exterior surface of an aluminosilicate nanoparticle may be functionalized with at least one ligand. A nanoparticle can have various amounts of ligands. For example, a nanoparticle has 1-50 ligands disposed on (e.g., covalently bonded to) an exterior surface of the nanoparticle. In various examples, a nanoparticle has 1-3 ligands, 1-10 ligands, 1-20 ligands, or 1-40 ligands disposed on (e.g., covalently bonded to) an exterior surface of the nanoparticle.

A method may be a targeting method. In various examples, the targeted portion of the sample or the individual may comprise one or more targeting moiet(ies). In general, targeting moieties are molecules or groups that can bind to or otherwise interact (e.g., specifically binding to or otherwise specifically interacting) with a targeting ligand or ligands of an aluminosilicate nanoparticle or nanoparticles. Non-limiting examples of targeting moieties include peptides, polypeptides, polynucleotides, sugars, polymers, lipids, glycans, peptidoglycans, and the like, and any combination or complex thereof. Other non-limiting examples of targeting moieties include receptors, receptor ligands, antibodies and fragments thereof, aptamers, affibodies, antibody and/or aptamer epitopes, binding agents and their binding partners (e.g., biotin and streptavidin), enzymes and their substrates, a targeting nucleic acid, target nucleic acid and guided nuclease (e.g., miRNA, gRNA, RISC, Cas, and the like), and the like, and any combination thereof. As used herein, the term "specific binding" refers to non-covalent physical association of a ligand and targeting moiet(ies), where the association between the ligand and the targeting moiet(ies) is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of the ligand and the targeting moiet(ies) may be considered specific if the equilibrium dissociation constant, $K_d$, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as, for example, those inside a cell or consistent with cell survival or the like. In some examples, specific binding can be accomplished by a plurality of weaker interactions (e.g., a plurality of individual interactions, where each individual interaction is characterized by a $K_d$ of greater than $10^{-3}$ M). In some examples, specific binding, which can be referred to as "molecular recognition," is a saturable binding interaction between the targeting ligand(s) and the targeting moiet(ies) that is dependent on complementary orientation of functional groups on each. Examples of specific binding interactions include, but are not limited to, primer-polynucleotide interaction, aptamer-aptamer target interactions, antibody-antigen interactions, avidin-biotin interactions, ligand-receptor interactions, metal-chelate interactions, hybridization between complementary nucleic acids, and the like. A targeting moiety may be endogenous or exogenous to the sample or the individual. In various examples, the aluminosilicate nanoparticle or at least a portion of the aluminosilicate nanoparticles may comprise one or more targeting ligand(s). A targeting ligand may be formed by reaction of a first ligand (e.g., first ligand group) that is conjugated to an aluminosilicate nanoparticle with a second ligand (e.g., a free ligand or ligand precursor) to form a second targeting ligand (e.g., second targeting group). In various examples, at least one targeting moiety of a sample or individual is complementary to at least one targeting ligand, such that the at least one targeting moiety is capable of binding (or binds) with the at least one targeting ligand.

In various examples, at least a portion of a surface of at least a portion of the aluminosilicate nanoparticles is functionalized with a targeting ligand (such as, for example, an antibody, which may be a secondary antibody). In the case of nanoparticle-secondary antibody conjugates, use of such nanoparticles allows the nanoparticles to target specific moieties (e.g., on a surface of a biological body, such as, for example, a cell, or within a cell) by using a primary antibody that specifically binds to this desired moiety. In turn, this primary antibody is then specifically targeted with the particle-secondary antibody conjugate, which then enables imaging using optical super-resolution microscopy. Imaging inside a cell may be done in fixed, permeabilized cells for better accessibility of the inside structure, in the case of relatively large targeting group(s). Imaging outside features of cells may be carried out using live-cell imaging.

The ligands carried by the aluminosilicate nanoparticles include, but are not limited to, diagnostic and/or therapeutic agents (e.g., drugs). Examples of therapeutic agents include, but are not limited to, chemotherapeutic agents, antibiotics, antifungal agents, antiparasitic agents, antiviral agents, and any combination thereof. An affinity ligand may be also be conjugated to the nanoparticle to allow targeted delivery of the nanoparticles. For example, the nanoparticle may be conjugated to a ligand which is capable of binding to a cellular component (e.g., on the cell membrane or in the intracellular compartment) associated with a specific cell type. The targeted molecule can be a tumor marker or a molecule in a signaling pathway. The ligand can have specific binding affinity to certain cell types, such as, for example, tumor cells. In certain examples, the ligand may be used for guiding the nanoparticles to specific areas, such as, for example, liver, spleen, brain, or the like. Imaging can be used to determine the location of the nanoparticles in an individual.

For example, drug-linker conjugate, where the linker group can be specifically cleaved by enzyme or acid condition in tumor for drug release, can be covalently attached to the functional ligands on the particles for drug delivery. For example, drug-linker-thiol conjugates can be attached to maleimido-PEG-particles through thiol-maleimido conjugation reaction post the synthesis of maleimido-PEG-particles. Additionally, both drug-linker conjugate and cancer targeting peptides can be attached to the particle surface for drug delivery specifically to tumor.

A ligand may be a biomolecule. Non-limiting examples of biomolecules include biotin, targeting ligands (e.g., targeting peptides such as, for example, cyclic-RGD and derivatives thereof, alpha-MSH and derivatives thereof, targeting antibody fragments, targeting glycans (e.g., sugar molecules targeting cell surface receptors), chelator molecules for metal radioisotopes, such as, for example, deferoxamine (DFO), which is an efficient chelators for radio-labeling with, for example, $Zr^{89}$, NODA, DOTA, drug molecules, and the like. A chelator molecule can form a chelating group that binds a radio metal to an aluminosilicate nanoparticle. Nanoparticles with radio metals may be used to perform PET or radiotherapy. Nanoparticles with a drug molecule/molecules may be used in therapeutic methods.

At least a portion of or all of the aluminosilicate nanoparticle(s) may have one or more or all of the following properties (which may result from functionalization of the nanoparticle(s): diagnostic properties (which may allow a surgeon to extract cancerous tissue using the optical signal of the nanoparticle(s) during surgery and/or subsequently allowing the pathologist to use optical super-resolution microscopy to look at the extracted cancer tissue/cells during histological analysis using optical super-resolution microscopy), therapeutic properties (e.g., functionalizing the surface of the nanoparticles with, for example, one or more targeting group(s) specific for a particular cancer, one or more, cytotoxic drug, etc. (Use of such nanoparticles may be used to treat a cancer, while extracted cancer tissue/cells could then be looked at using optical super-resolution microscopy).

In various examples, an aluminosilicate nanoparticle comprises an aluminosilicate core and a periphery that carries one or more targeting group(s) and one or more small molecule therapeutic payload(s). As an illustrative example, using such aluminosilicate nanoparticles live-cell optical super-resolution microscopy can be carried out on cancer cells that are incubated with those particles to determine the mode of action of the therapeutic particle "drug" within the cells. Comparing that with different compositions of their particles, e.g., as a function of the number of targeting groups or therapeutic molecules on their particle surface, would allow them generation of a particle structure-cancer cell behavior correlations.

In an aspect, the present disclosure provides compositions. The compositions comprise a plurality of aluminosilicate nanoparticles of the present disclosure. A composition may comprise a mixture of two or more different nanoparticles. In various examples, a composition comprises one or more type(s) (e.g., having different average size and/or one or more different compositional feature(s)). Nonlimiting examples of compositions are provided herein.

In various examples, none of the aluminosilicate nanoparticles (or none of the nanoparticles) in a composition comprises a metal other than aluminum. In various examples, a composition does not comprise a heavy atom (e.g., sulfur or the like) or a metal (e.g., a heavy metal or the like). In various examples, a composition does not comprise an oxygen scavenger. In various examples, a composition does not comprise a reducing agent or oxidizing agent.

For example, a composition comprises a plurality of aluminosilicate nanoparticles (e.g., a combination of aluminosilicate nanoparticles). Any of the nanoparticles may be surface functionalized with one or more type of polyethylene glycol group(s) (e.g., polyethylene glycol groups, functionalized (e.g., functionalized with one or more ligand and/or a reactive group) polyethylene glycol groups, or any combination thereof).

In various examples, a composition comprises a plurality of aluminosilicate nanoparticles of the present disclosure. The composition may further comprises an aqueous medium and the nanoparticles are present as a dispersion in the aqueous medium. Non-limiting examples of aqueous media include buffers and the like. For example, the composition can also comprise a buffer suitable for administration to an individual (e.g., a mammal such as, for example, a human). The buffer may include or be a pharmaceutically acceptable carrier.

In various examples, e.g., when imaging samples (such as, for example, biological materials), such as, for example, cells or the like, the one or more (e.g., a plurality of) aluminosilicate nanoparticle(s) is/are disposed in a regular buffer (which may be a non-toxic imaging buffer). The contacting (e.g., administering) of the one or more (e.g., a plurality of) aluminosilicate nanoparticle(s) may be carried out using a composition comprising the one or more (e.g., a plurality of) aluminosilicate nanoparticle(s) and an imaging buffer (which may be a non-toxic imaging buffer).

A composition may comprise one or more pharmaceutically acceptable carrier(s) and/or excipient(s). The carrier(s) or excipient(s) is/are "acceptable" in the sense of being compatible with the other ingredients of the formulation and not deleterious to the recipient thereof. Examples of pharmaceutically acceptable carriers or excipients include, but are not limited to, pharmaceutically acceptable materials, compositions, or vehicle, such as, for example, a liquid or solid filler, diluents, bulking agents, stabilizers, solvent or encapsulating material involved in carrying or transporting the aluminosilicate nanoparticles from one organ, or portion of the body, to another organ, or portion of the body, or stabilizing the aluminosilicate nanoparticles, or the like. Examples of pharmaceutically acceptable carriers, excipients, and stabilizers can be found in Remington: *The Science and Practice of Pharmacy* (2005) 21st Edition, Philadelphia, Pa. Lippincott Williams & Wilkins. For example, suitable carriers or excipients which are nontoxic to recipients at the dosages and concentrations employed, can include buffers such as, for example, acetate, Tris, phosphate, citrate, and other organic acids; antioxidants including ascorbic acid and methionine; preservatives such as, for example, octadecyldimethylbenzyl ammonium chloride; hexamethonium chloride; benzalkonium chloride, benzethonium chloride; phenol, butyl or benzyl alcohol; alkyl parabens such as, for example, methyl or propyl paraben; catechol; resorcinol; cyclohexanol; 3-pentanol; and m-cresol; amino acids, such as, for example, glycine, glutamine, asparagine, histidine, arginine, or lysine; monosaccharides, disaccharides, and other carbohydrates including, but not limited to, glucose, mannose, or dextrins; chelating agents such as, for example, EDTA; tonicifiers such as, for example, trehalose and sodium chloride; sugars such as, for example, sucrose, mannitol, trehalose or sorbitol; surfactant such as, for example, polysorbate; salt-forming counter-ions such as, for example, sodium; and/or non-ionic surfactants such as, for example, Tween or polyethylene glycol (PEG). The pharmaceutical compositions may comprise other therapeutic agents. The present compositions can be provided as single doses or in multiple doses covering the entire or partial treatment regimen. The compositions can be provided in liquid, solid, semi-solid, gel, aerosolized, vaporized, or any other form from which it can be delivered to an individual.

In an aspect, the present disclosure provides kits. A kit comprises one of more aluminosilicate nanoparticle(s) and/or one or more composition(s) of the present disclosure. The composition(s) may be pharmaceutical compositions. Non-limiting examples of kits are provided herein.

In various examples, a kit comprises one or more aluminosilicate nanoparticle(s) of the present disclosure and/or one or more composition(s) of the present disclosure, and instructions for use of the nanoparticle(s) and/or composition(s) for treatment of (e.g., administration to) an individual. In various examples, a kit comprises one or more aluminosilicate nanoparticle(s) and/or one or more composition(s) of the present disclosure, and instructions for use of the nanoparticle(s) and/or composition(s) obtaining an image of a sample or an individual, or a portion thereof, as described herein.

In various examples, a kit is or comprises a closed or sealed package that contains the aluminosilicate nanoparticle(s) and/or composition(s). In certain examples, the package comprises one or more closed or sealed vial(s), bottle(s), blister (bubble) pack(s), or any other suitable packaging for the sale, or distribution, or use of the nanoparticle(s) and/or composition(s). The printed material can include printed information. The printed information can be provided on a label, or on a paper insert, or printed on the packaging material itself. The printed information can include information that identifies the compound in the package, the amounts and types of other active and/or inactive ingredients, and instructions for taking the composition, such as, for example, the number of doses to take over a given period of time or the like, and/or information directed to a pharmacist and/or another health care provider, such as, for example, a physician or a patient. The printed material can include an indication that the pharmaceutical composition and/or any other agent provided with it is for treatment of cancer and/or any disorder associated with cancer. In examples, the kit includes a label describing the contents of the container and providing indications and/or instructions regarding use of the contents of the kit to treat any cancer.

The following Statements describe various examples of methods, aluminosilicate particles, and kits of the present disclosure and are not intended to be in any way limiting:

Statement 1. A method of obtaining an optical super-resolution image (e.g., an optical image or the like with resolution below Abbe's diffraction limit) of a sample or a portion thereof or an individual or a portion thereof comprising: contacting the sample (which may be a biological material) or individual with a one or more (e.g., a plurality of) aluminosilicate nanoparticle(s) of the present disclosure (e.g., aluminosilicate nanoparticle(s) comprising at least one fluorophore (e.g., fluorophore molecule, such as, for example, an organic dye molecule or the like) (or at least one fluorophore group, such as, for example, a group derived from a fluorophore molecule) covalently bonded to the aluminosilicate network of the individual aluminosilicate nanoparticles) (e.g., fluorophore molecule(s) or group(s) are encapsulated by the aluminosilicate matrix or network) or a composition comprising the one or more (e.g., plurality) of aluminosilicate nanoparticle(s); irradiating the sample or a portion thereof or the individual or a portion thereof, thereby exciting at least one of the fluorophore(s) (e.g., fluorophore molecule(s), such as, for example, an organic dye molecule(s) or the like) of a nanoparticle (which may be a nanoparticle of the composition); and obtaining a fluorescence image (which may be a super-resolution image) or a sequence of fluorescence images which can be processed to obtain a super-resolution image (which may be a super-resolution optical image) of the sample or portion thereof or the individual or a portion thereof.

Statement 2. A method according to Statement 1, wherein the obtaining the fluorescence image comprises: detecting electromagnetic radiation (e.g., detecting electromagnetic radiation from each individual aluminosilicate nanoparticle), the detected electromagnetic radiation having been emitted by the fluorophore(s) (e.g., fluorophore molecule(s), such as, for example, an organic dye molecule(s) or the like) of the individual particle as a result of excitation by the excitation electromagnetic radiation; and processing signals corresponding to the detected electromagnetic radiation to provide one or more fluorescence image(s) (which may be optical super-resolution images) of the sample or portion thereof or the individual or a portion thereof.

Statement 3. A method according to Statement 1 or Statement 2, wherein at least a portion of the optical super-resolution image exhibits sub-diffraction limit resolution.

Statement 4. A method according to any one of the preceding Statements, wherein the method is an optical super-resolution microcopy method including, but not limited to, ground state depletion (GSD) microscopy, stochastic optical reconstruction microscopy (STORM), direct stochastic optical reconstruction microscopy (dSTORM), stimulated emission and depletion (STED), or photoactivated localization microscopy (PALM).

Statement 5. A method according to Statement 1, wherein the contacting is administering the composition to the individual.

Statement 6. A method according to Statement 5, wherein the electromagnetic radiation is directed into the individual.

Statement 7. A method according to Statement 6, wherein the electromagnetic radiation is directed into a region, wherein the region is within the individual.

Statement 8. A method according to any one of the preceding Statements, wherein the electromagnetic radiation comprises one or more wavelength(s) from 400 to 1200 nm, including all nm values and ranges therebetween.

Statement 9. A method according to any one of the preceding Statements, wherein the irradiation is carried out using a laser (e.g., a single laser).

Statement 10. A method according to any one of the preceding Statements, wherein the electromagnetic radiation is a single wavelength.

Statement 11. A method according to any one of the preceding Statements, wherein the organic dye is a fluorescent dye or fluorescent protein.

Statement 12. A method according to Statement 11, wherein the organic dye is chosen from cyanine dyes, rhodamine dyes (e.g., carborhodamine dyes and the like), coumarin dyes, boron-dipyrromethene (BODIPY) dyes, xanthene dyes, eosin dyes, carbopyronine dyes, methylene blue, fluorescein, Acridine Orange, and a group/groups derived therefrom, and any combination thereof.

Statement 13. A method according to any one of the preceding Statement, wherein the aluminosilicate nanoparticles individually have at least one dimension (which may be a longest linear dimension, such as, for example, a diameter) of 1 to 30 nm, including all 0.1 nm values and ranges therebetween.

Statement 14. A method of treating an individual for cancer comprising: obtaining an image of a sample (e.g., a biological material) or a portion thereof or an individual or a portion thereof according to any one of Statements 1-13.

Statement 15. A method according to Statement 14, wherein the method further comprises visualization of the abnormal cells after administration of the nanoparticle or the composition.

Statement 16. A method according to Statement 15, wherein the visualization is carried out using fluorescence imaging.

Statement 17. A method according to any one of the preceding Statements, wherein the method further comprises administration of a chemotherapy agent.

Statement 18. A method according to any one of the preceding Statements, wherein the method further comprises surgical removal of at least a portion of a cancerous tissue from the individual.

Statement 19. A method according to any one of the preceding Statements, wherein the method further comprises subjecting the individual to a radiation treatment.

Statement 20. A kit comprising one or more (e.g., a plurality of) aluminosilicate nanoparticle(s) and/or a composition comprising the aluminosilicate nanoparticle(s), and instructions for use of composition(s) for obtaining an image of a sample or a portion thereof or an individual or a portion thereof (e.g., according to a method of the present disclosure) and/or treatment of an individual for cancer.

The steps of the methods described in the various embodiments and examples disclosed herein are sufficient to carry out a method of the present disclosure. Thus, in various embodiments, a method consists essentially of any combination of the steps of the methods disclosed herein. In various other embodiments, a method consists of such steps.

The following example is presented to illustrate the present disclosure. It is not intended to be limiting in any matter.

Example

Stochastic optical reconstruction microscopy (STORM) is an optical super-resolution microscopy (SRM) technique that traditionally requires toxic and non-physiological imaging buffers and setups that are not conducive to live-cell studies. It was observed that ultrasmall (<10 nm) fluorescent core-shell aluminosilicate nanoparticles (aC' dots) covalently encapsulating organic fluorophores enable STORM with a single excitation source and in a regular (non-toxic) imaging buffer. It was shown that four-fold coordinated aluminum is responsible for dye blinking, likely via photoinduced redox processes. It was demonstrated that this phenomenon is observed across different dye families leading to probes brighter and more photostable than the parent free dyes. Functionalization of aC' dots with antibodies allowed targeted fixed cell STORM imaging. Finally, aC' dots enabled live cell STORM imaging providing quantitative measures of the size of intracellular vesicles and the number of particles per vesicle. Results suggest the emergence of a powerful ultrasmall, bright, and photostable optical SRM particle platform with characteristics relevant to clinical translation for the quantitative assessment of cellular structures and processes from live-cell imaging.

A new class of amorphous quantum nanomaterials was previously introduced, in which the incorporation of different amounts of foreign atoms into the amorphous inorganic aluminosilicate glass of an ultrasmall aluminosilicate core and poly(ethylene glycol) (PEG) shell core-shell nanoparticle (aC' dot) alters the quantum behavior of fluorescent dyes covalently encapsulated in the glassy core, leading to substantially altered macroscopic optical behavior. After introducing iodine as foreign atoms (iaC' dots), illumination led to increased inter-system crossing (ISC) rates to triplet excited dye states via spin-orbit coupling, in turn resulting in improved reactive oxygen species (ROS) generation useful, e.g., in photodynamic therapy (PDT). When introducing thiol groups as foreign atoms (srC' dots), illumination led to dye blinking, which enabled STORM based optical SRM. While the latter approach removed the requirement for (WE in the imaging buffer, a buffer system with an OS system was still employed, as was a two-laser excitation system, all complicating applications in live-cell imaging.

A surprising discovery that aC' dots, without incorporation of thiol groups and in the complete absence of any particular imaging buffer and under simple illumination with a single light source, exhibit dye blinking enabling STORM based SRM is described. As disclosed herein, the blinking mechanism of aC' dots is very different from that in previous thiol-containing srC' dots. In the latter particles, under illumination thiol-dye adducts disrupt dye π-electron delocalization leading to dark states and associated blinking in the presence of an OS system, whereas such systems quench aC' dot blinking. In a range of cross experiments with free dyes and aluminum-free C' dots, it was revealed that four-fold coordinated aluminum in the aluminosilicate matrix is responsible for dye blinking, likely via photo-induced redox processes. It was also demonstrated that dye blinking can be generalized over several dye families covering the visible to near-infrared (NIR) spectral range, leading to brighter and more photostable SRM probes relative to their parent free dyes. Also disclosed herein are examples of applications of these SRM probes in fixed and live-cell imaging. The latter reveals access to a wealth of information on cellular structure and particle processing that can be extracted from quantitative assessment of live-cell SRM data sets. This includes measures of the size of intracellular vesicles confining nanoprobe motion and the number of particles per vesicle, i.e., detailed information about the way cells process such ultrasmall fluorescent core-shell silica nanoparticles highly relevant for their clinical translation, e.g., in the field of drug delivery in oncology.

Figure 1A:
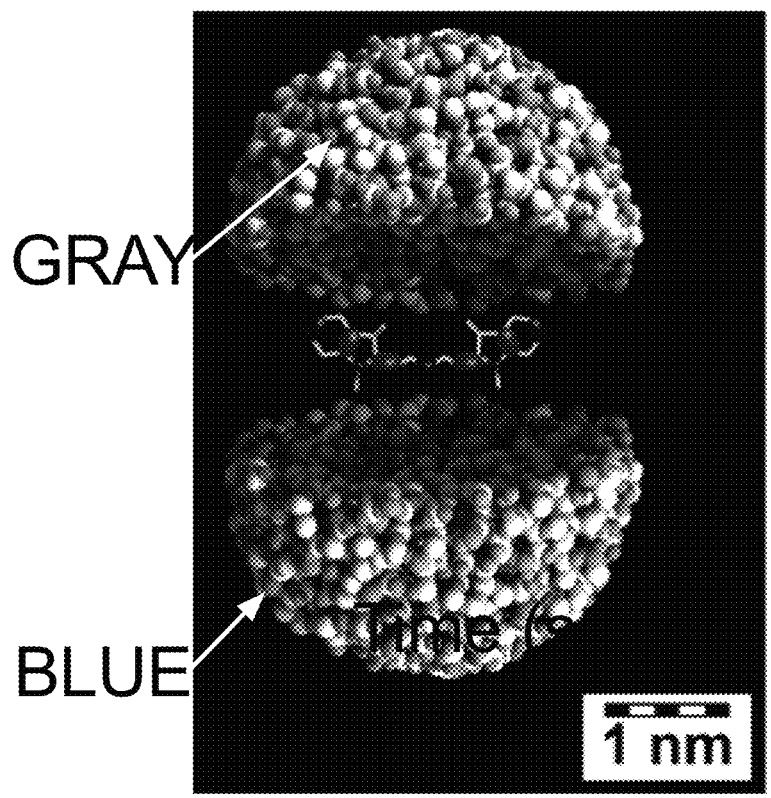
FIGS. 1A-1E show.
Figure 1B:
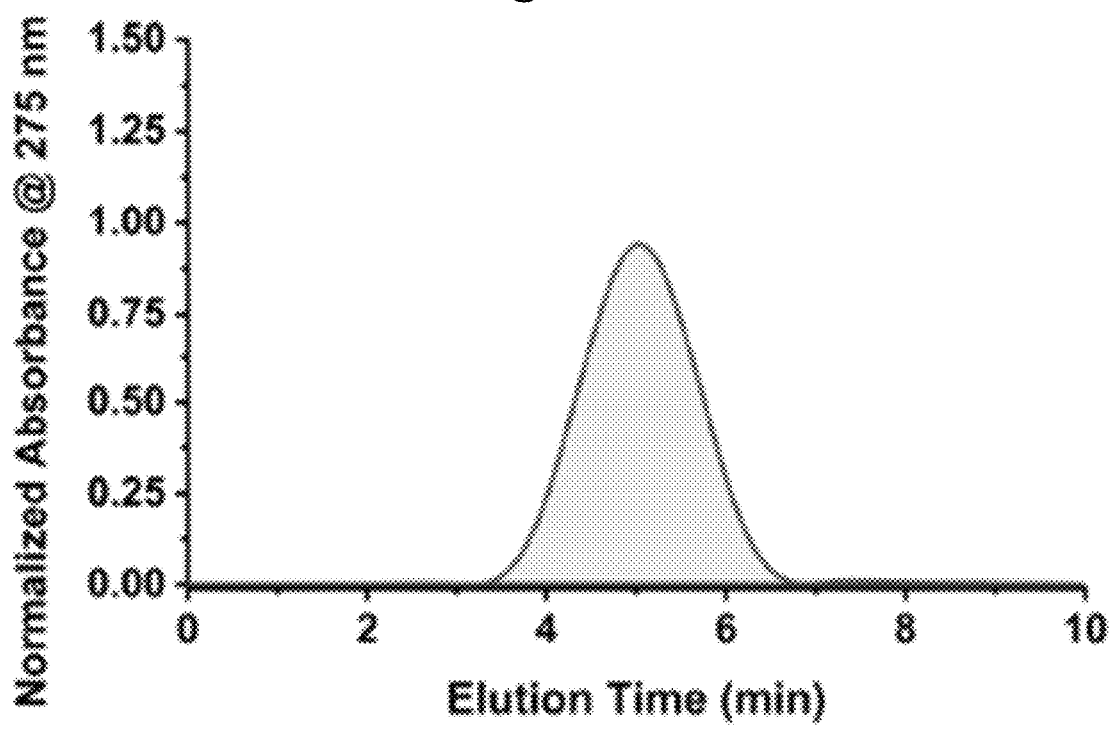
Figure 1C:
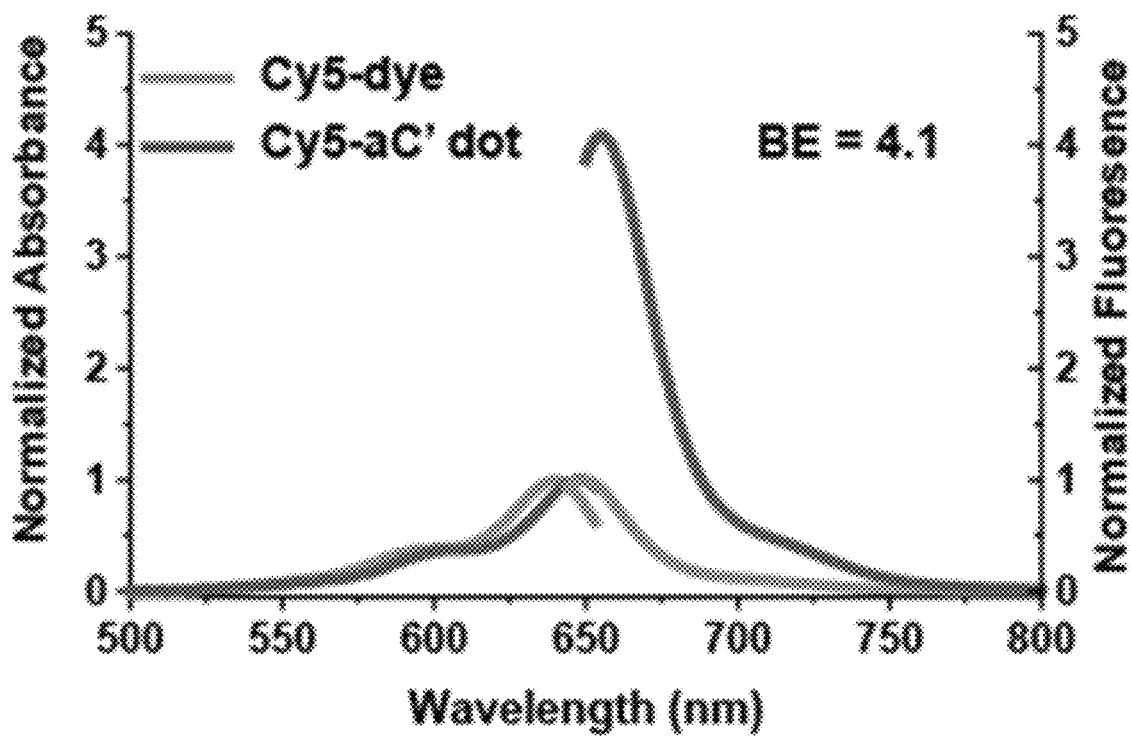
Figure 1D:
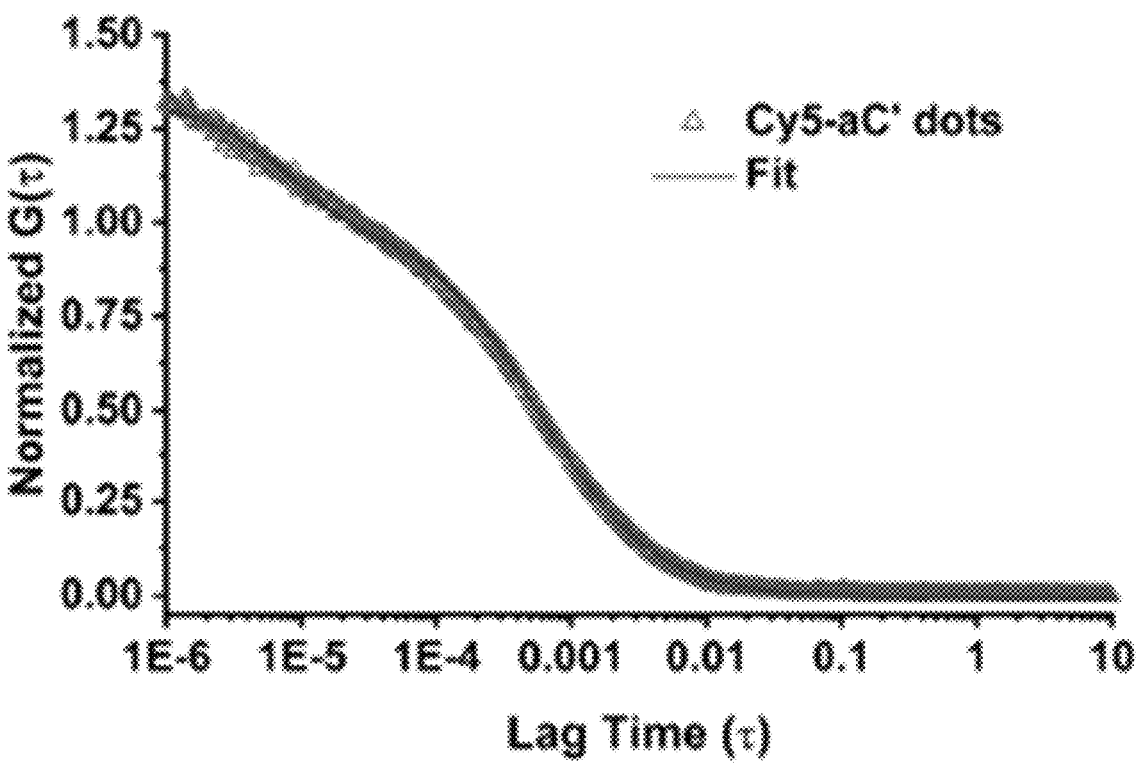
Figure 1E:
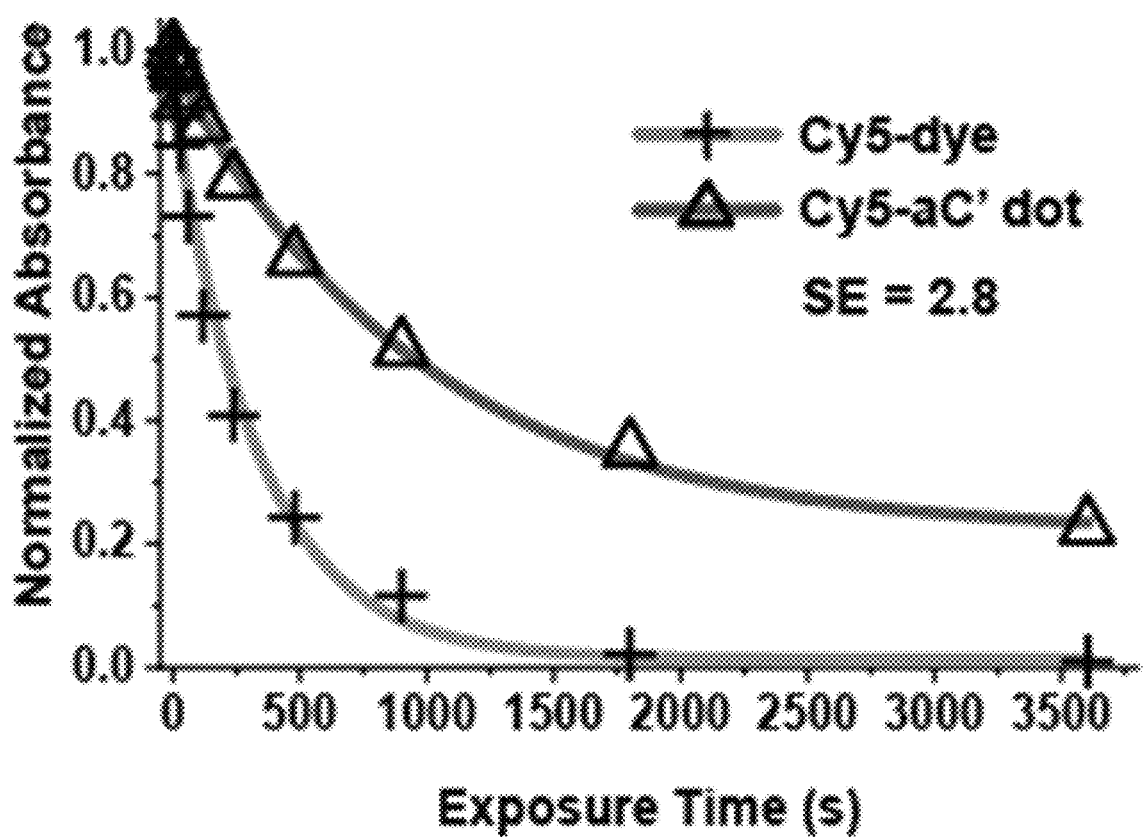

NIR dye Cy5 encapsulating and PEGylated ultrasmall fluorescent core-shell silica nanoparticles with and without aluminum (PEG-Cy5-aC' and PEG-Cy5-C' dots, respectively) were synthesized in aqueous conditions in the presence or absence of aluminum-tri-sec-butoxide (ASB), respectively, as described herein. The standard molar ratio of tetramethoxy-silane (TMOS) and ASB in the reaction feed to co-condense the aC' dot cores was 87:13. The molar ratio of Si:Al in the aC' dot core is 92:8, according to energy-dispersive X-ray spectroscopy (EDS) measurements (FIG. 7B), i.e., only slightly lower than what is expected from the molar ratio of precursors in the synthesis feed (Si:Al of 87:13). A molecular level rendering of the local environment of such an aluminosilicate core with this molar composition encapsulating Cy5 with its π electron orbitals is shown in FIG. 1A (Si white, O gray, Al blue), together with purified PEG-Cy5-aC' dot characterization results. The Gaussian shaped gel permeation chromatography (GPC) elution profile (FIG. 1B) revealed high product purity, while the transmission electron microscopy (TEM) images at different magnifications (FIG. 7A) suggested a narrow particle size distribution. The high rigidity of the aluminosilicate core with full encapsulation of the Cy5 dye translated into a larger than 4-fold brightness enhancement over free Cy5 dye (FIG. 1C) in UV-Vis absorption and emission spectroscopy analysis. This effect has been quantitatively analyzed in earlier static and dynamic spectroscopy studies and is due to an increase in radiative rate and decrease in non-radiative rate. As shown previously, this brightness enhancement relative to free dye carries over into photon emission enhancements during dye blinking, which is crucial for a potential probe for STORM for which localization precision is proportional to the square root of brightness. Confocal fluorescence correlation spectroscopy (FCS) measurements on the diffusing PEG-Cy5-aC' dots yielded one-component autocorrelation functions (ACF) suggesting an average particle diameter of 4.6 nm and corroborating the narrow size dispersity reflected in the TEM results (FIG. 1D). An average of 2.5 Cy5 dyes per particle was determined from the combination of FCS derived sample concentration and absorption spectroscopy results. Furthermore, photobleaching studies based on previously published methods as described herein showed that Cy5 encapsulated in aC' dots is 2.8 times more photostable than in free form (FIG. 1E). Since it was shown in two separate previous studies that Al is four-fold coordinated in aC' dots, replacing Si in the silica network, the same solid-state $^{27}$Al nuclear magnetic resonance (NMR) spectroscopy experiments were not repeated on C' dot samples here. Zeta potential measurements of aC' dots showed a negative surface charge with an average of −11.9 mV as seen in FIG. 8. Characterization results on PEG-Cy5-C' dots used as a reference in this study, i.e., without Al in the core, suggested a hydrodynamic diameter of 5.5 nm with 2.4 Cy5 dyes per particle (FIGS. 9A-9C).

Next the optical properties of fluorescent C' dots and aC' dots were compared to free parent Cy5 dye by single molecule imaging. Biotinylated Cy5 dye (Cy5-biotin), PEG-Cy5-C' dots, and PEG-Cy5-aC' dots were immobilized on streptavidin-coated glass dishes as described elsewhere, with Hank's balanced salt solution (HBSS) as the imaging buffer. HBSS is an aqueous buffer routinely used in live-cell imaging. The immobilized single emitters were imaged under different conditions by a total internal reflection fluorescence (TIRF) microscope. A red laser ($\lambda_{ex}$=640 nm) was used to excite Cy5. In the presence of thiolated buffers (βME+OS cocktail), the red laser leads to Cy5-thiol adduct formation (dark state), while a UV laser ($\lambda$=405 nm) was used to dissociate these adducts as described above. The temporal fluorescence traces of individual dyes or particles across different conditions (FIG. 2) were collected with an electron multiplying charge coupled device (EMCCD) camera for 500 s at 50 ms integration times. In FIG. 2, traces with different colors represent different single fluorophore or particle localizations. The numbers depicted above the spectra represent the measured average equilibrium duty cycles, i.e., the ratios of the "on" time over "total" time of the respective fluorescence traces at steady-state in the 200-400 second time window, as described by the Zhuang group. Probes with low duty cycles are easier to resolve, e.g., in STORM, as it is less likely for their emission PSFs to overlap in cases of high labeling density.

Figure 2A:
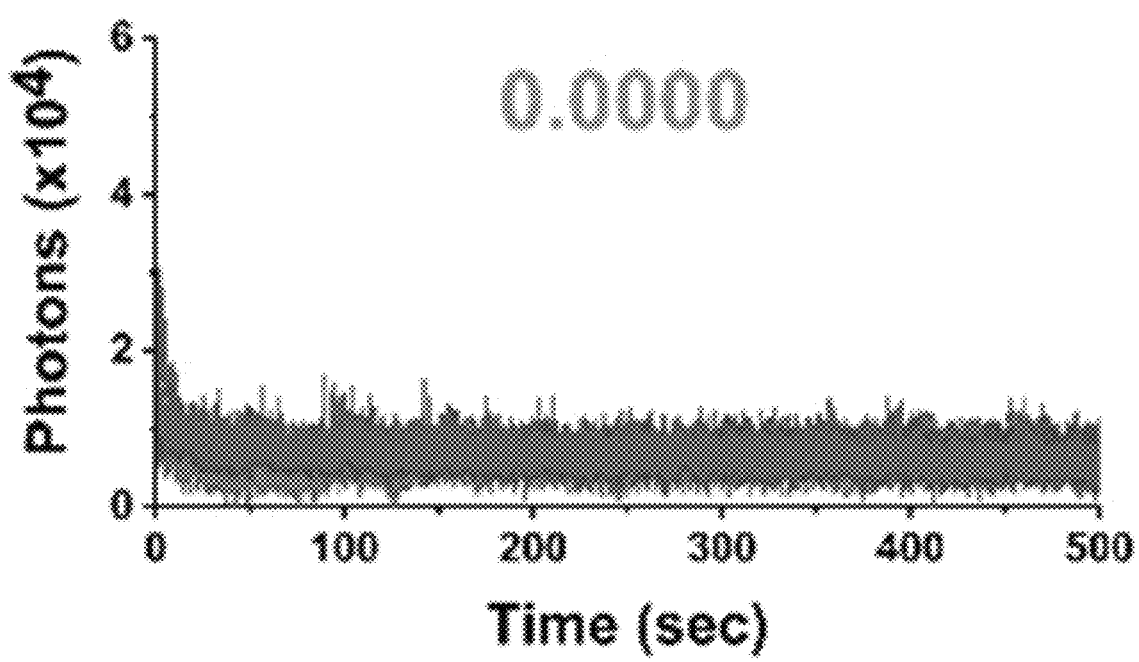
FIGS. 2A-2J show.
Figure 2B:
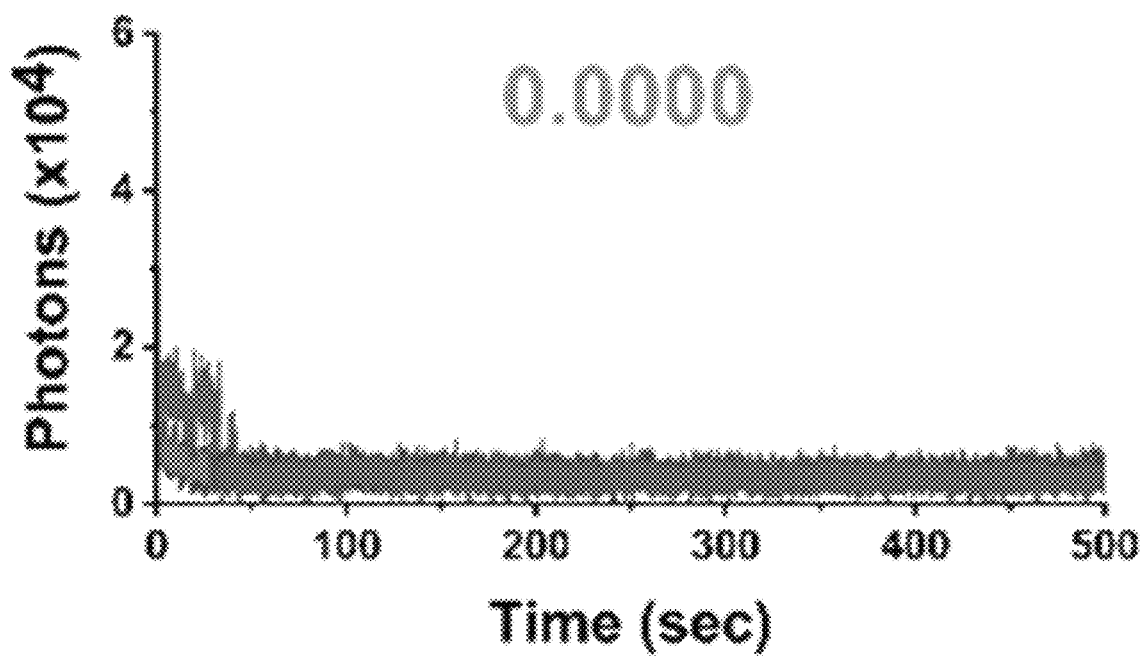
Figure 2C:
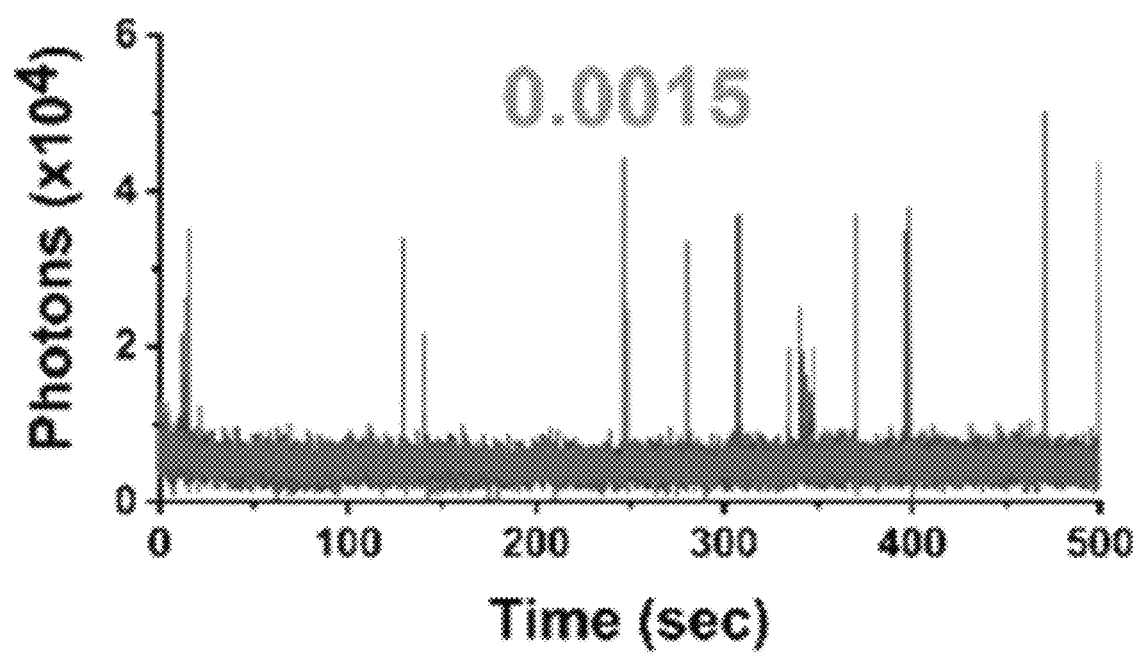
Figure 2D:
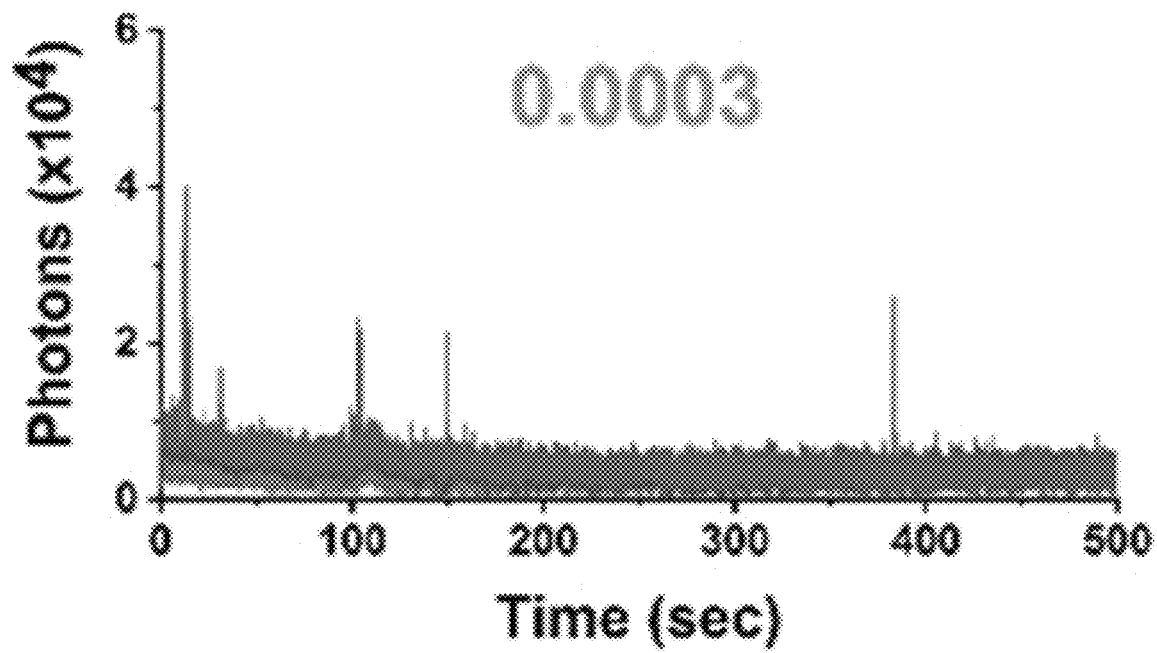
Figure 2E:
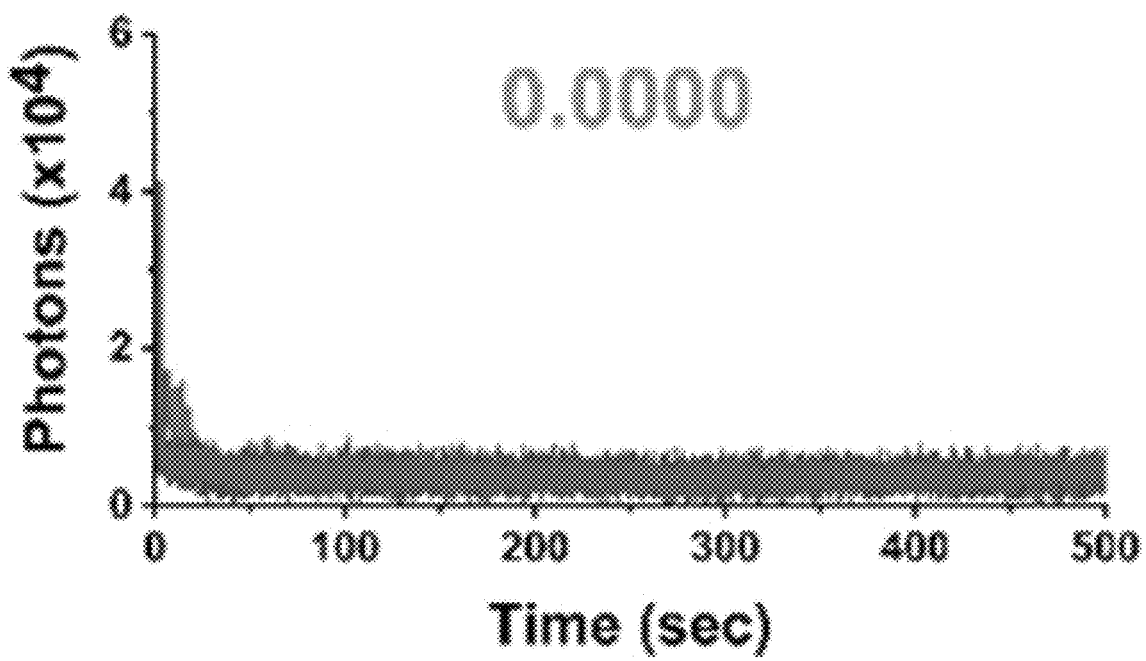
Figure 2F:
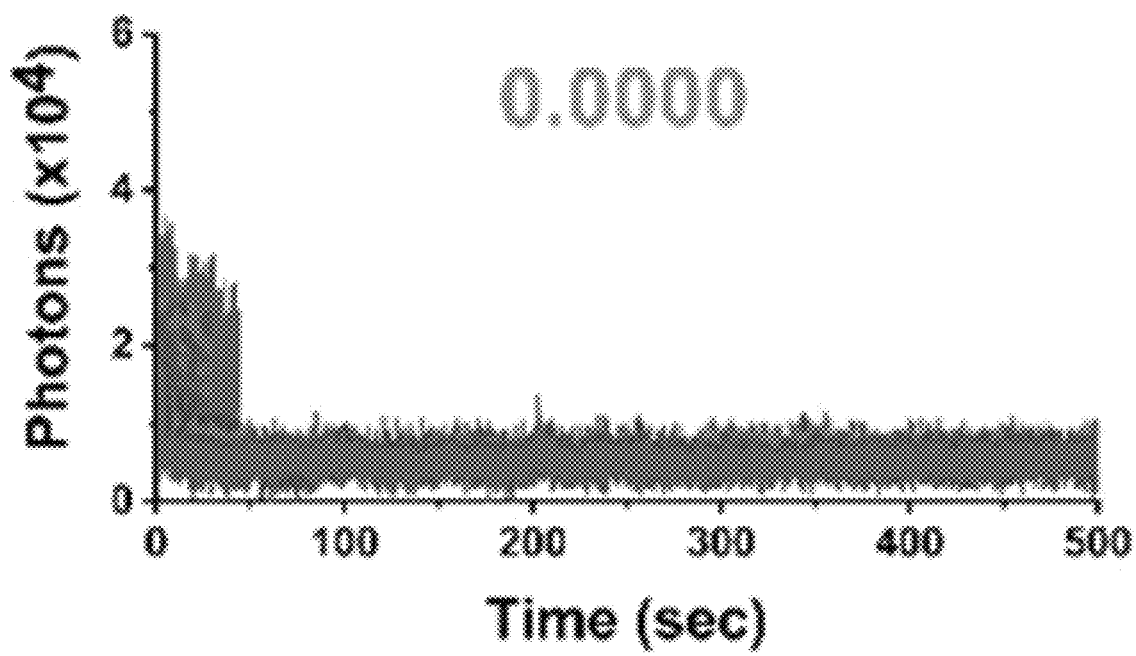
Figure 2G:
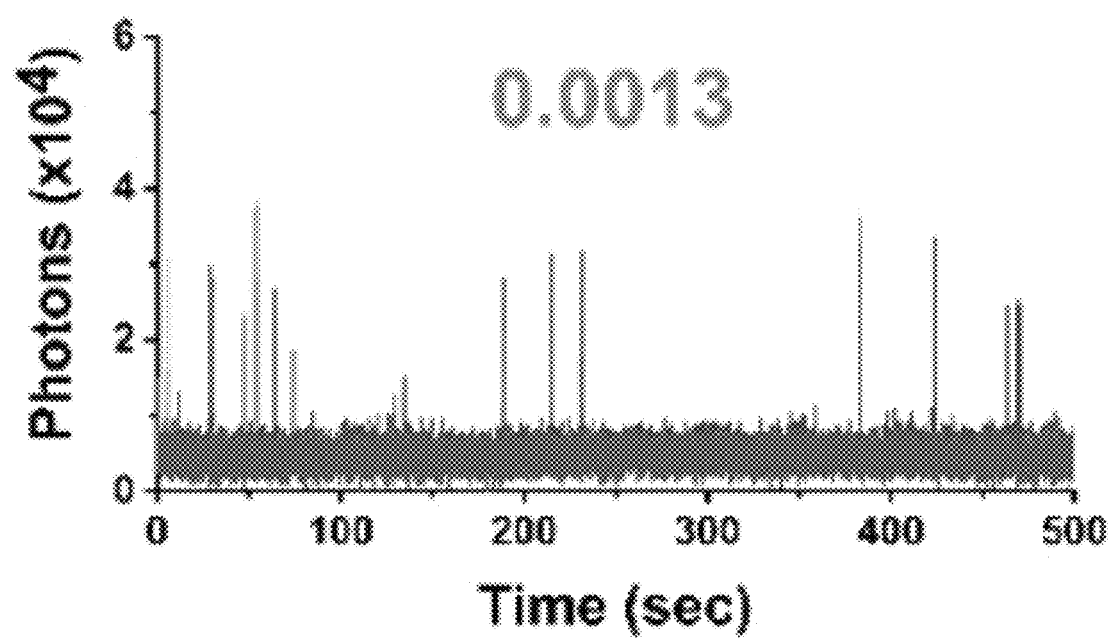
Figure 2H:
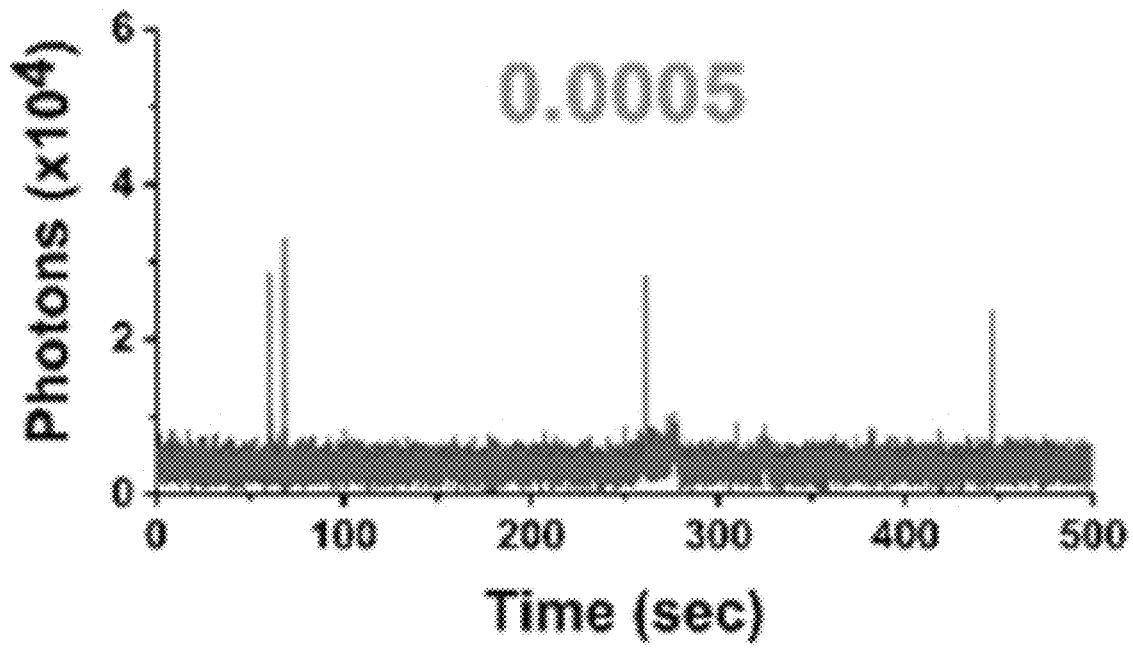
Figure 2I:
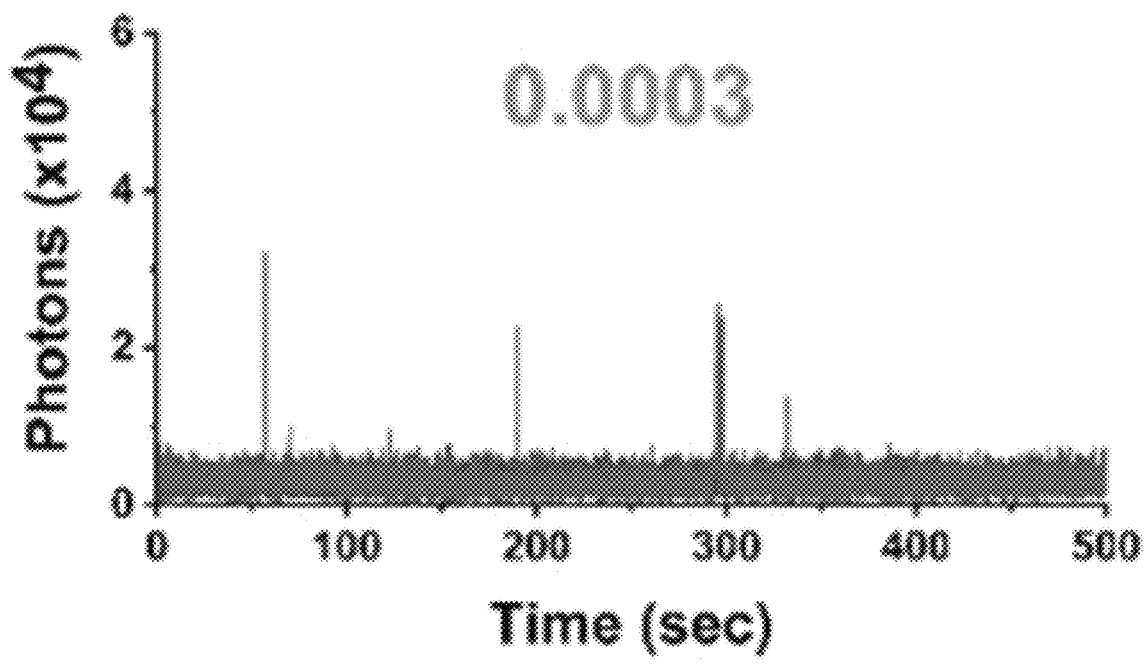
Figure 2J:
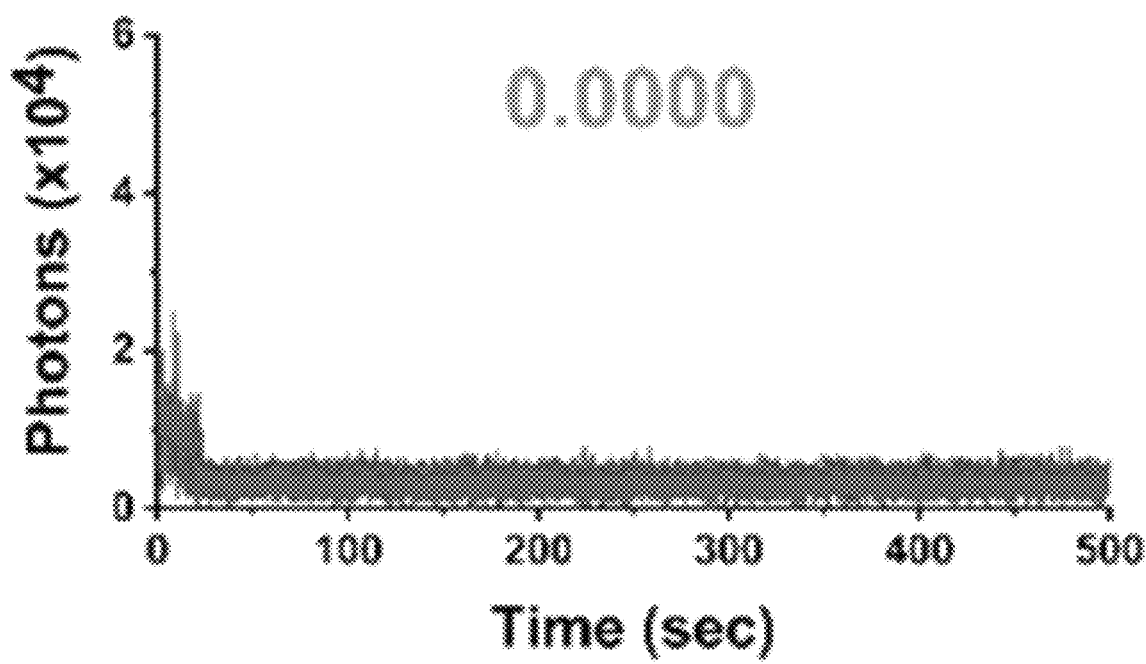

Neither Cy5 dye nor PEG-Cy5-C' dots (i.e., without Al) showed blinking in HBSS buffer when excited with only a red laser (FIGS. 2A, 2E). In stark contrast, under the same conditions PEG-Cy5-aC' dots exhibited dye blinking behavior suitable for STORM (FIG. 2I), with exceptional equilibrium duty cycles around 0.0003. Since the only difference between PEG-Cy5-C' dots and PEG-Cy5-aC' dots was the absence or presence, respectively, of aluminum, these results suggested that aluminum in the nanoparticle core plays a key role in encapsulated Cy5 dye blinking. While Cy5 dye or PEG-Cy5-C' dots still did not blink when exposed to illumination from both red and UV lasers (FIGS. 2B, 2F), they did show blinking when excited by both lasers and in the presence of thiols and oxygen scavengers of the standard STORM buffer, albeit with higher duty cycles >0.001 (FIGS. 2C, 2G). This verified that both samples are capable of blinking under the right conditions. Corroborating that aluminum is the key factor in what makes Cy5 blink in aC' dots, it was observed that Cy5 dye and PEG-Cy5-C' dots blink (FIGS. 2D, 2H) with duty cycles comparable to that of PEG-Cy5-aC' dots when excited with only a red laser and the addition of 9 mM of sodium aluminate into the HBSS buffer. Sodium aluminate was chosen because aluminum is also in a four-fold coordinated state. The pH of HBSS at this concentration of sodium aluminate is ~8.7, but it was confirmed that PEG-Cy5-aC' dot blinking is not strongly dependent on pH or dye charge (FIGS. 10, 11A-11D). Furthermore, Cy5-dye was exposed to aluminum chloride in HBSS and saw no blinking with only red laser excitation (FIG. 12), suggesting that only certain coordination levels of aluminum are capable of inducing blinking. While it is possible that coordination states other than four-fold could lead to blinking, these experiments were beyond the scope of this present disclosure. Finally, PEG-Cy5-aC' dots did not blink under red laser excitation when oxygen scavengers were added to the HBSS imaging buffer (FIG. 2J), suggesting that dissolved oxygen naturally present in aqueous solutions also plays a key part in PEG-Cy5-aC' dot blinking. Blinking was also observed when PEG-Cy5-aC' dots were imaged in ethanol, which also naturally contains dissolved oxygen (FIG. 13), demonstrating that an aqueous environment is not required for blinking to occur. These results together suggest that aC' dots are optimal STORM probe candidates for live-cell imaging as they combine high brightness, high photostability, and low equilibrium duty cycle blinking when excited with a single laser source in a regular buffer, i.e., in the absence of cytotoxic imaging cocktails including thiol compounds and oxygen scavenging systems.

Figure 3A:
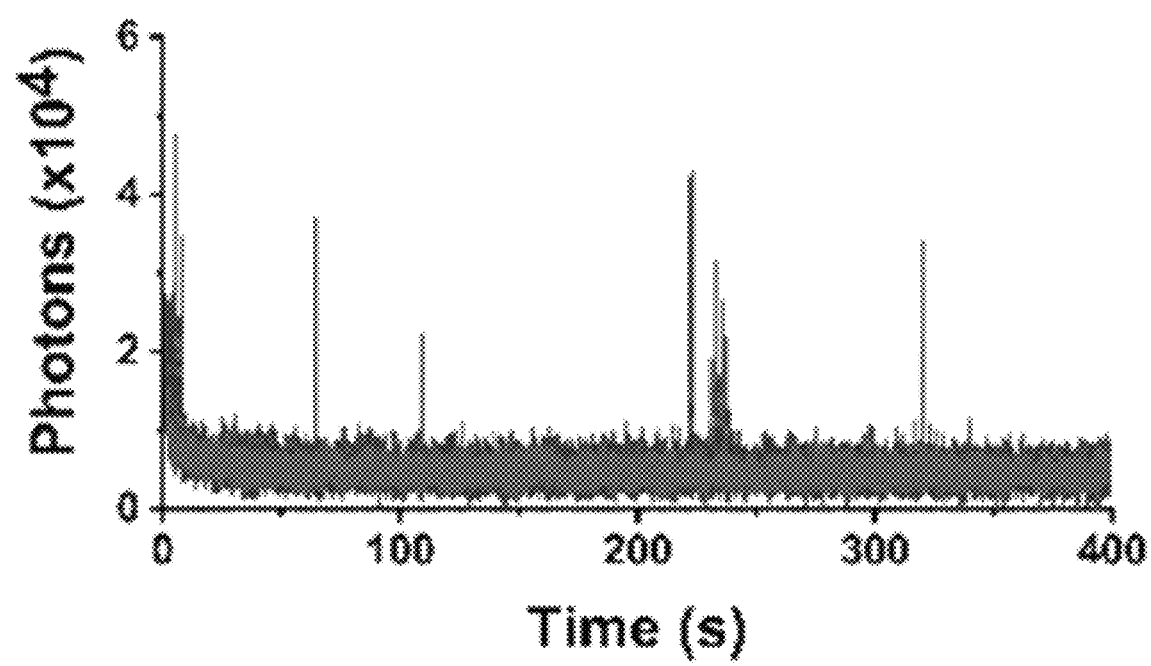
FIGS. 3A-3J show.
Figure 3B:
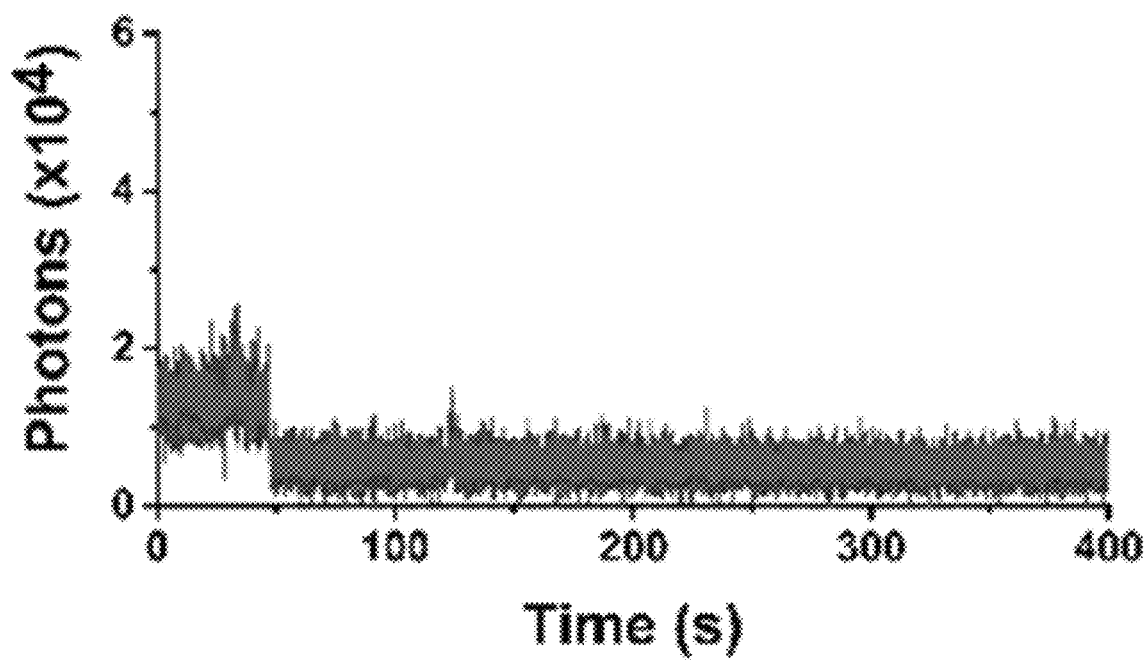
Figure 3C:
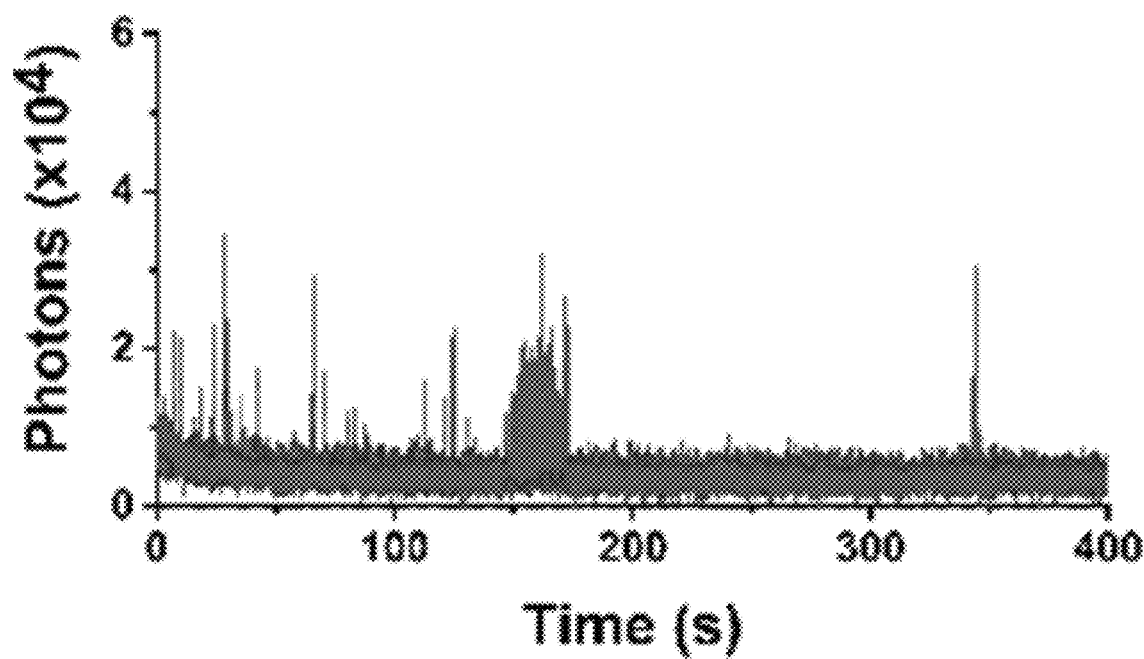
Figure 3D:
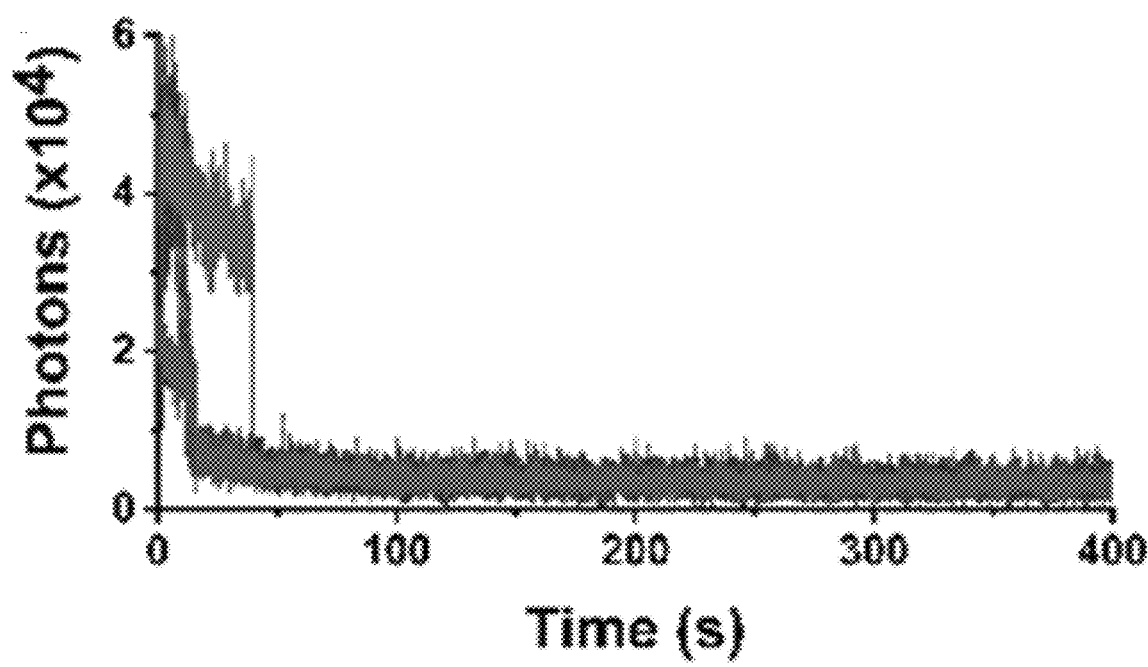
Figure 3E:
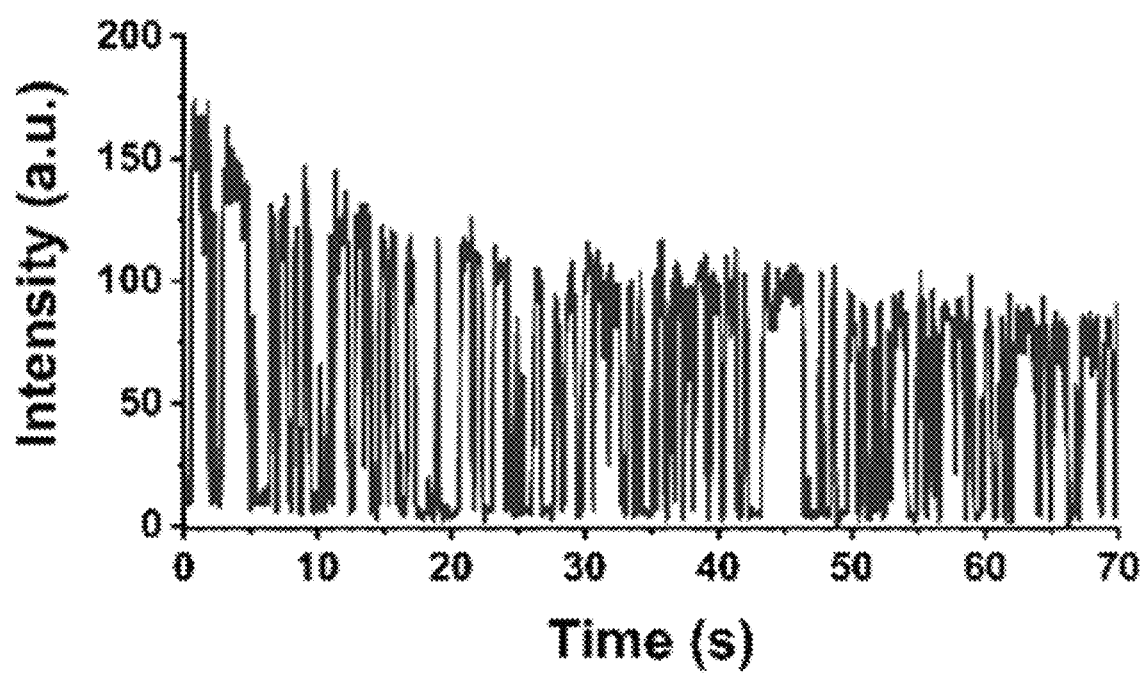
Figure 3F:
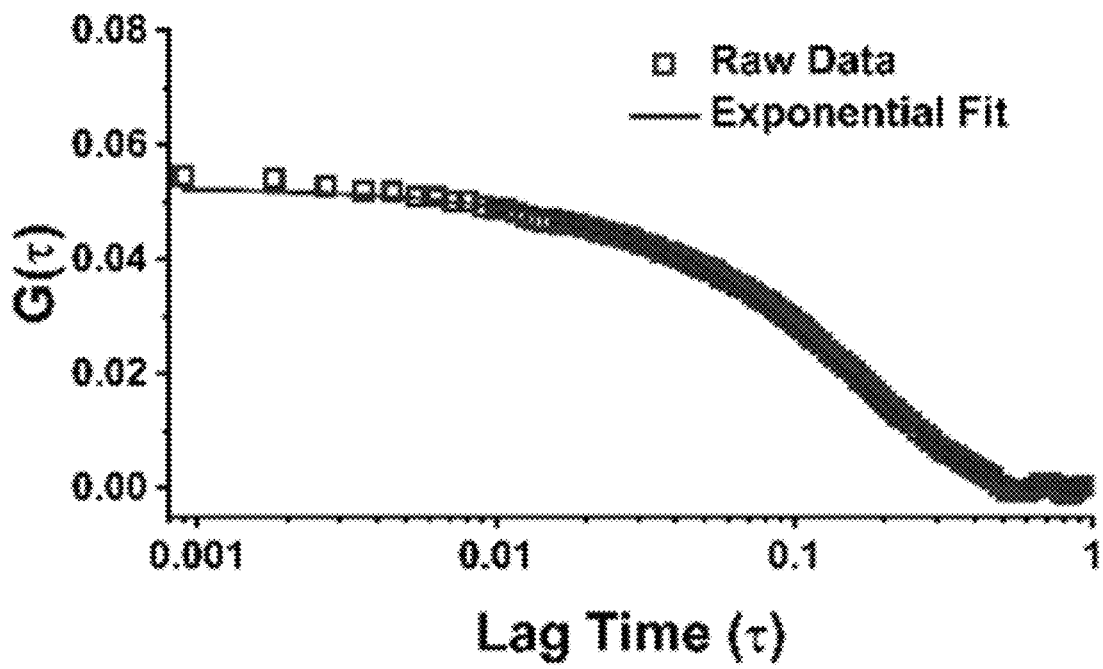

Interestingly, a small subset (~5-10%) of aC' dots exhibited early on-off blinking behavior near the beginning of data collection before fluorescence ceased, as shown in FIGS. 14A-14B, likely associated with probes sticking to the substrate. Performing imaging FCS on such fluorescence time traces and fitting to a single exponential decay revealed an average off time ($\tau_{off}$) of 94±14 ms (FIG. 14C). Note that the particles are immobilized, hence any decay in the autocorrelation function is due to photophysical processes rather than diffusion. To obtain a more accurate $\tau_{off}$, the integration times were switched from 50 ms to 1 ms integration times and imaging FCS performed on this subset of early-blinking particles. As shown in FIG. 3E, the same blinking behavior was observed at this shorter integration time. Improved autocorrelation analysis revealed a similar $\tau_{off}$ of 100±10 ms (FIG. 3F). This is significantly longer than the triplet $\tau_{off}$ of Cy5 (~15 ms), suggesting that PEG-Cy5-aC' dots may undergo a radical-mediated redox-type blinking. Using higher time resolution (i.e., shorter integration times) for PEG-Cy5-aC' dots exhibiting low equilibrium duty cycle blinking (as observed with 50 ms integration times) revealed rapid on-off blinking during each effective blink (FIGS. 15A-15E), similar to that described for the particle subset with early on-off blinking behavior. This suggested that the underlying photophysics was similar across all blinking phenomena observed for PEG-Cy5-aC' dots.

Figure 3G:
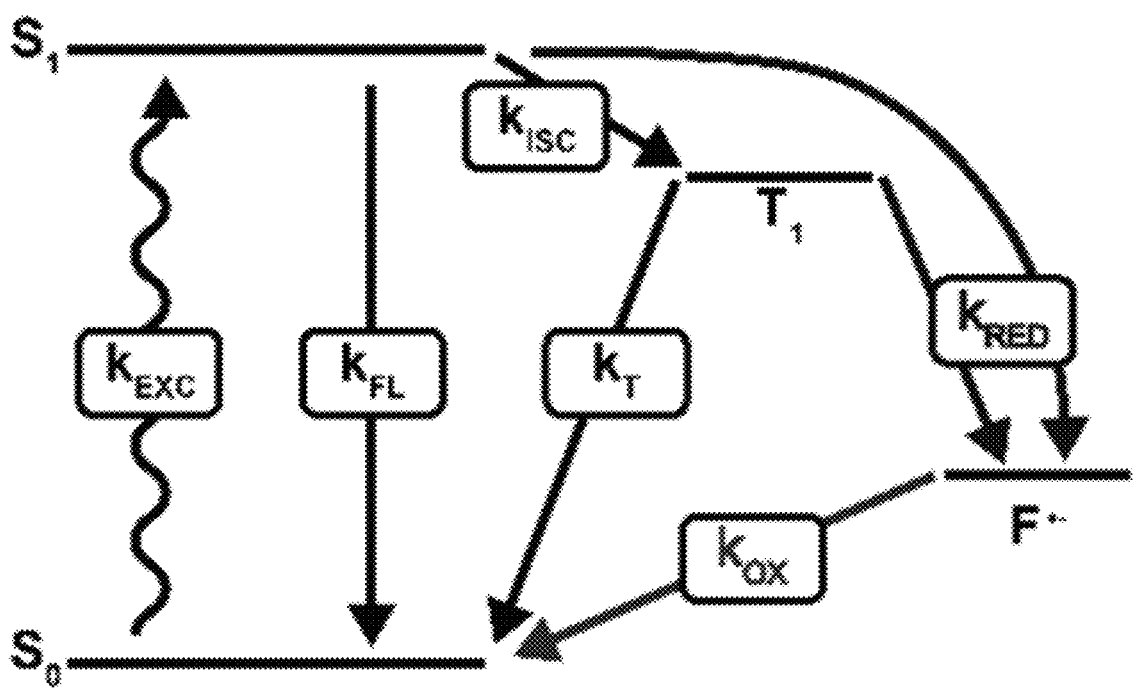

After a dye absorbs a photon to an excited singlet state, it may perform one of the following actions: drop back to its singlet ground state via fluorescence, cross-over via intersystem crossing (ISC) to an excited triplet state, undergo redox interactions to a radical ionic dark state (in case of a neutral dye), or photobleach (see Jablonski diagram, FIG. 3G). In the case of a redox mechanism, a (neutral) dye can either be oxidized into a radical cation dark state and return to its singlet ground state via a reduction step, or it can be reduced to a radical anion dark state and return to the singlet ground state via an oxidation step. However, oxidized dye radical cations typically represent a much higher energy state than reduced radical anions, and therefore are less thermodynamically favorable in the presence of redox agents. The fact that dissolved oxygen also appears to play an important role in the blinking behavior led us to hypothesize that the four-fold coordinated aluminum in aC' dots gives rise to a redox mechanism where the fluorophore Cy5 is first reduced into a dark state (e.g., F.—in case of a neutral fluorophore), and subsequently is oxidized by dissolved oxygen thereby returning to its ground state (FIG. 3G). Please note that dissolved oxygen can reach encapsulated Cy5 dye within the silica core via micropores observed in sol-gel derived silica. To confirm radical-based redox blinking, PEG-Cy5-aC' dots as well as Cy5-dye plus sodium aluminate were exposed in HBSS to 10% (v/v) tert-butanol, a known radical scavenger. As expected, all low duty-cycle blinking at steady-state was suppressed (see representative examples in FIGS. 3A-3D).

The measured $\tau_{off}$~100 ms is somewhat higher than the ~60 ms previously reported for Cy5 immobilized on DNA. It was previously observed that Cy5 $\tau_{off}$ increases if the concentration of reductant is increased. Similarly, a small increase in τoff was observed as the amount of aluminum precursor (ASB) used during the synthesis of PEG-Cy5-aC' dots was increased (FIG. 16), supporting the hypothesis that aluminum plays a role in the reduction of Cy5. Based on a rough calculation shown herein, Cy5 dyes within an aC' dot experience a local four-fold coordinated aluminum concentration of 3M. If aluminum is involved in the redox process, the reductant concentration is several orders of magnitude greater than the highest reported reductant concentrations in solution of up to 1 mM. This may contribute to the higher $\tau_{off}$ values of the Cy5 embedded in the aC' dots.

The 1 ms integration time experiments were repeated with immobilized PEG-Cy5-aC' dots in HBSS and added Trolox, an antioxidant, in order to deplete dissolved oxygen. Under this condition, any obvious blinking was not observed in the temporal fluorescence trace and no meaningful ACF analysis could be performed (FIGS. 17A-17F). Similarly, with 50 ms integration time, when OS system was added to free Cy5-dye plus sodium aluminate, no blinking was observed. However, the blinking was recovered when 1 mM methyl viologen, a known oxidant, was added to the oxygen-depleted solution (FIGS. 18A-18D). These results corroborate that oxygen plays the role of the oxidant and is necessary to observe (redox) blinking of PEG-Cy5-aC' dots.

Figure 3H:
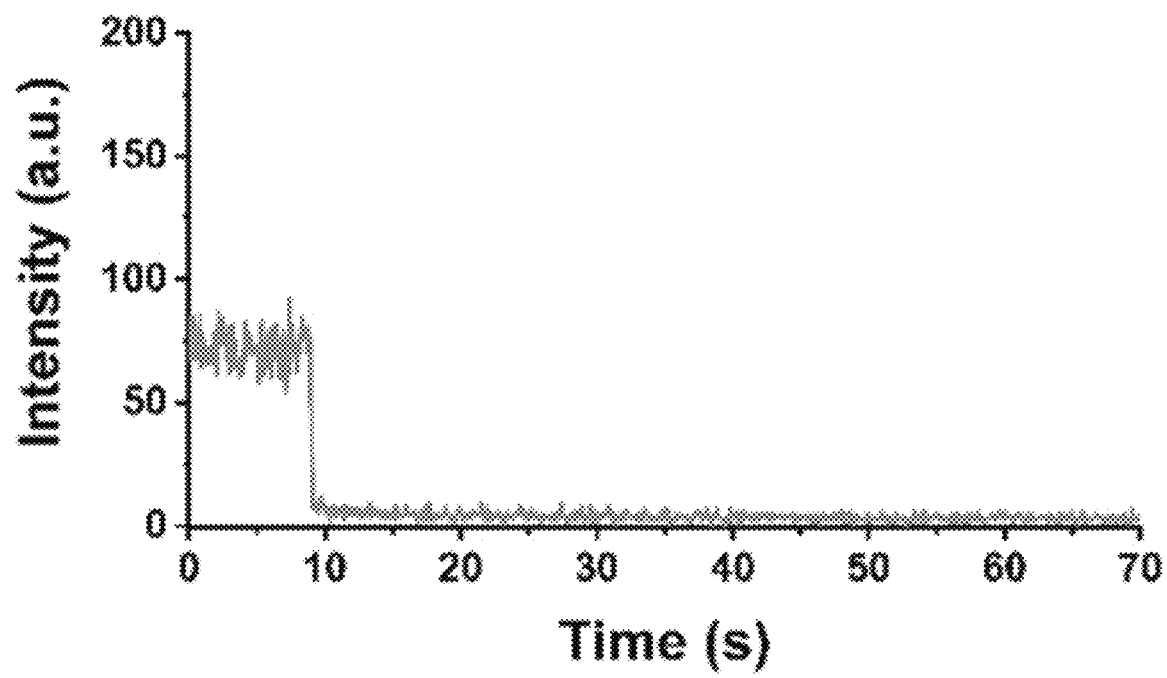
Figure 3I:
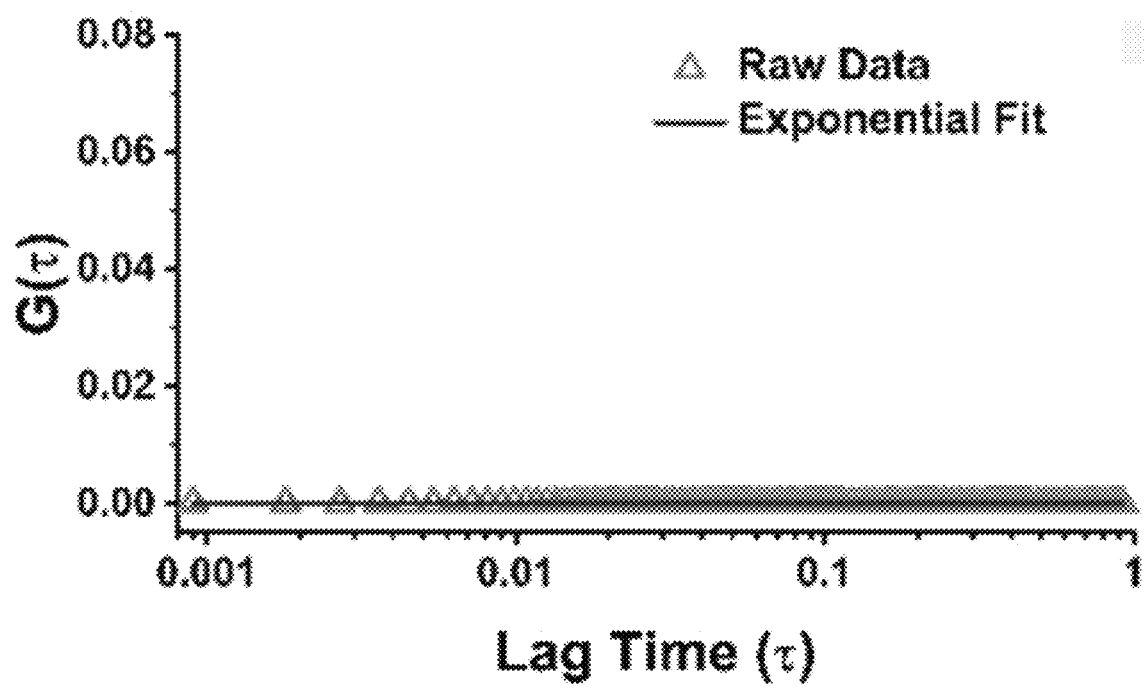
Figure 3J:
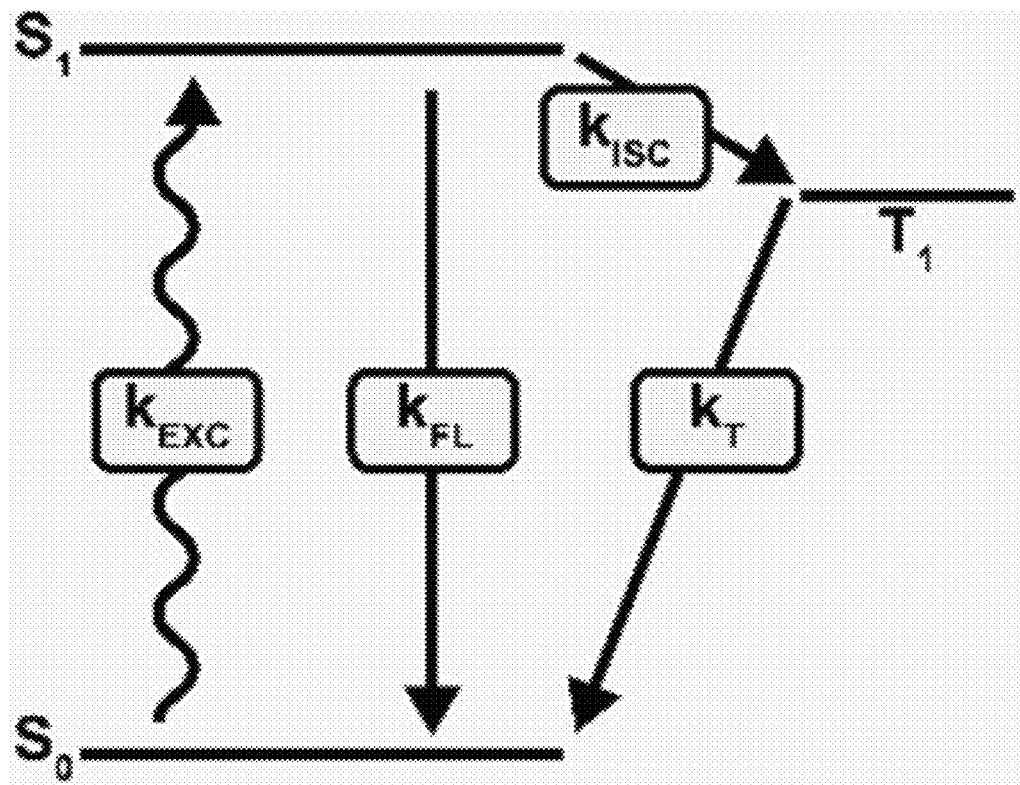

The temporal fluorescence behavior of PEG-Cy5-C' dots differed dramatically from that of PEG-Cy5-aC' dots. In the absence of Al in the PEG-Cy5-C' dots, within the first 10 seconds of collection time, Cy5 irreversibly photo-bleached into a dark state (FIG. 3H), and ACF analysis results (FIG. 3I) were similar to that of the camera background. For PEG-Cy5-C' dots this is consistent with the absence of redox photophysics, where available electronic states can be described by a conventional Jablonski diagram for fluorescent dyes (FIG. 3J).

The fluorescence enhancement as well as blinking capabilities provided by covalent aC' dot encapsulation are not limited to cyanine NIR dye Cy5. As demonstrated in FIGS. 4A-4E, relative to the respective parent free dyes, PEG-dye-aC' dots substantially enhance the fluorescence of a variety of encapsulated dyes such as 7-diethylamino-coumarin-3-carboxylic acid (DEAC; brightness enhancement factor (BE):10.0), fluorescein-5 (F-5; BE: 5.3), Cy3 (BE: 5.5), ATTO647N (BE: 2.0), and Cy7 (BE: 2.9). This list includes a coumarin dye (DEAC), fluorescein (F-5), other cyanines (Cy3 and Cy7), as well as a carbopyronine dye (ATTO647N) with absorption and emission spectra covering almost the entire visible spectrum all the way into the NIR regime (i.e., Em from 473 through 773 nm). Aluminum-containing aC' dots covalently encapsulating all these dyes exhibited excellent blinking behavior with equilibrium duty cycles <0.001 suitable for STORM (FIGS. 4F-4J) in plain HBSS buffer and exposed to only one respective excitation source. Furthermore, these dyes encapsulated in PEG-dye-aC' dots all showed substantially enhanced photostability compared to their free form (FIGS. 4K-4O) with stability enhancement factors (SE) when fit to a single exponential function of: DEAC (SE: 7.8), F-5 (SE: 1.4), Cy3 (SE: 7.7), ATTO647N (SE: 11.2), and Cy7 (SE: 18.6). Other dyes that were tested, and showed enhanced brightness and photostability as well as low equilibrium duty cycles, include Alexa Fluor 647 and Cy5.5 (FIGS. 19A-19F). Optical characteristics together with the net charge of all dyes encapsulated in PEG-dye-aC' dots relative to their free form are summarized in Table 1.

TABLE 1

| Dye-aC' dot | Parent Dye Net Charge | Excitation/ Emission | Brightness Enhancement (BE) | Stability Enhancement (SE) | Duty Cycle (DC) |
|---|---|---|---|---|---|
| DEAC-aC' dot | 0 | 430/473 | 9.98 ± 0.63 | 7.80 ± 0.8 | 0.0002 |
| F-5-aC' dot | 0 | 494/508 | 5.34 ± 0.08 | 1.40 ± 0.24 | 0.0007 |
| Cy3-aC' dot | +1 | 551/555 | 5.49 ± 0.21 | 7.70 ± 2.69 | 0.0009 |
| Cy5-aC' dot | +1 | 647/660 | 4.12 ± 0.04 | 2.83 ± 0.30 | 0.0003 |
| Alexa Fluor 647-aC' dot | −3 | 650/655 | 1.87 ± 0.15 | 0.90 ± 0.04 | 0.0003 |
| ATTO647N-aC' dot | +1 | 651/659 | 2.03 ± 0.19 | 11.16 ± 4.43 | 0.0007 |
| Cy5.5-aC' dot | +1 | 686/691 | 5.82 ± 0.25 | 2.82 ± 0.46 | 0.0005 |
| Cy7-aC' dot | +1 | 754/760 | 3.20 ± 0.19 | 18.64 ± 3.02 | 0.0009 |

Overall enhancement effects are substantial, sometimes an order of magnitude or larger. Differences in brightness and photostability enhancements across different dyes in part are due to dye encapsulation efficiency as a function of dye molar mass and net charge. For example, the dye exhibiting the least enhancement effects upon covalent encapsulation, Alexa Fluor 647, was the only dye studied with a net negative charge (of −3). From earlier studies and corroborated by recent high-performance liquid chromatography (HPLC) analyses, dye charge is highly correlated with encapsulation efficiency into particle cores, with high negative net charge being particularly detrimental. These data suggest that dyes such as DEAC, F-5, Cy3, and Cy5.5 that in free form, due to their structure and fluorescence properties, have severe limitations for STORM applications may be converted into viable probes when encapsulated in aC' dots. Moreover, dyes previously identified as already optimal for STORM applications such as Alexa Fluor 647 and Cy5 may be further enhanced when encapsulated in PEG-aC' dots. It was previously demonstrated that brightness enhancements over free dye indeed directly carry over into photon output enhancements in dye blinking. Taken together, these data point to the emergence of an ultrasmall, bright, and photostable nanoparticle platform for SRM. Building on recent advances, e.g., in bright and photostable nanoprobes including upconversion as well as advanced polymer nanoparticles, ultrasmall aC' dots constitute an attractive platform for bioimaging and SRM that does not contain heavy metals, exhibits on-off fluorescence cycling characteristics optimal for STORM, and takes advantage of a wide spectral range that can be tailored by dye choice.

The highly tunable surface of aC' dots, through post-PEGylation surface modification by insertion (PPSMI) reactions, enables attachment of targeting ligands without compromising particle stability. Through PPSMI and subsequent click chemistry modifications, similar to techniques previously reported, secondary antibodies ($Ab_2$) were covalently attached to aC' dots, e.g., yielding $Ab_2$-PEG-ATTO647N-aC' dots (FIG. 5A). Using confocal FCS (FIG. 20 and Table 2), it was demonstrated that these modified aC' dots bind to primary antibodies ($Ab_1$), and that two $Ab_2$-PEG-ATTO647N-aC' dots can bind to one primary antibody, known as secondary antibody binding amplification, to yield $Ab_1$-$Ab_2$-PEG-ATTO647N-aC' dots.

TABLE 2

| Ab-Particle Complex | Diameter (nm) | Dyes/Complex |
|---|---|---|
| PEG-ATTO647N-aC' dot | 6.0 | 1.1 |
| $Ab_2$-PEG-ATTO647N-aC' dot | 12.3 | 1.1 |
| $Ab_1$-$Ab_2$-PEG-ATTO647N-aC' dot | 21.7 | 1.9 |

Figure 5B:
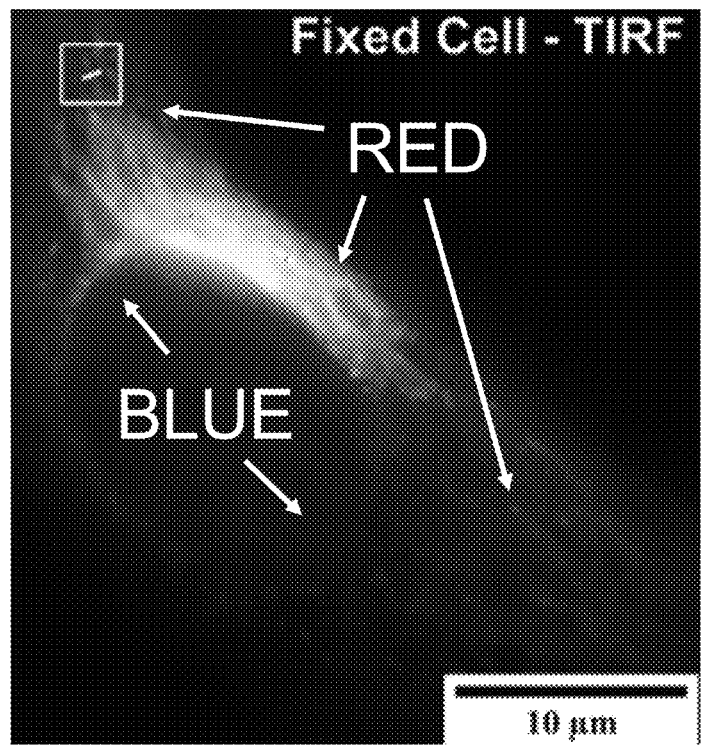
Figure 5C:
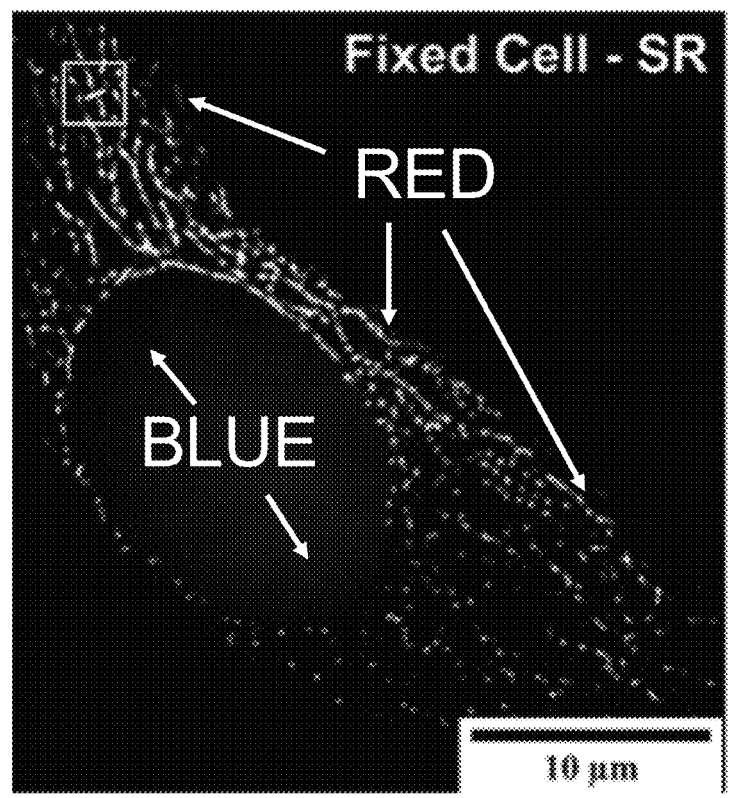
Figure 5D:
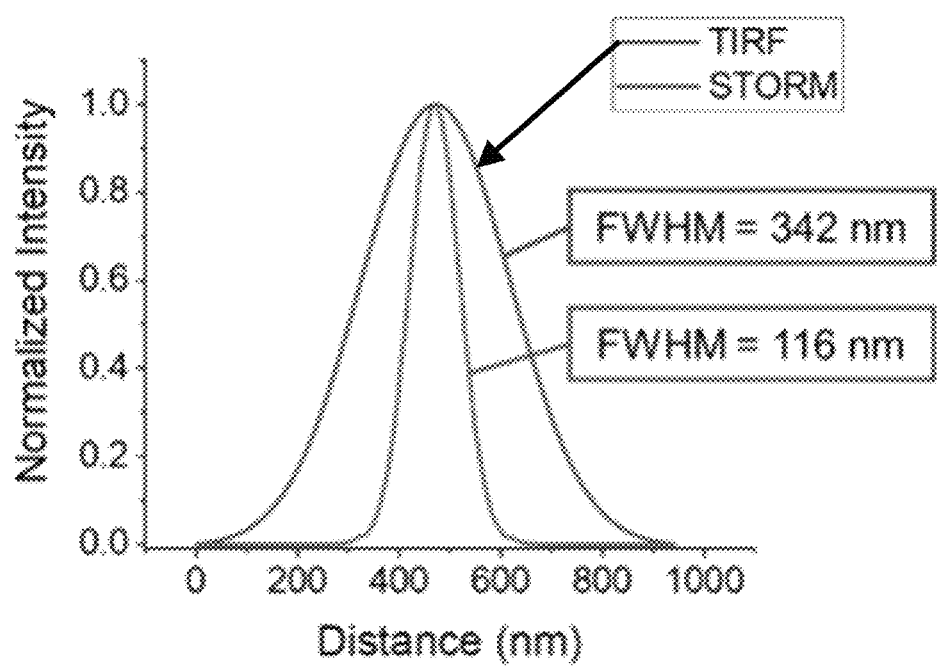

In FIGS. 5B-5C HeLa cells were fixed with 4% paraformaldehyde, permeabilized with NP-40 detergent, and exposed to mouse anti-α-tubulin primary antibodies followed by subsequent goat anti-mouse IgG bearing Abe-PEG-ATTO647N-aC' dot addition as described herein. FIG. 5B shows a diffraction-limited TIRF microscopy image of a resulting cell with a Hoechst 33342 nuclear stain. Some tubulin-like structures can be identified under TIRF microscopy, but due to their overlapping PSFs separating them into individual tubules is not possible. In contrast, when the STORM image in FIG. 5C was reconstructed, the labeled tubulin structures now could be resolved below the diffraction limit and overlapping networks of individual tubules could be identified. These cells were imaged in aqueous phosphate buffer saline (PBS) with a red laser. Intensity profiles across a selected microtubule in both the TIRF and STORM images to show the improvement in resolution can be seen in FIG. 5D.

Figure 6A:
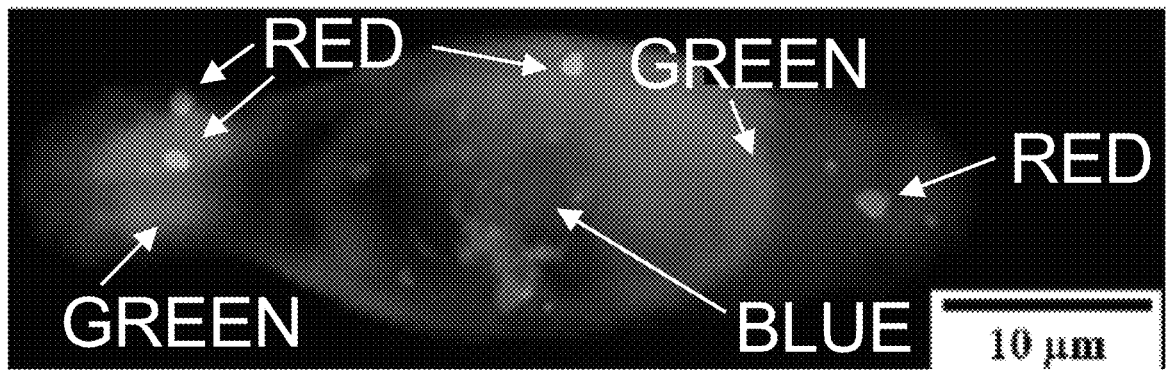
Figure 6B:
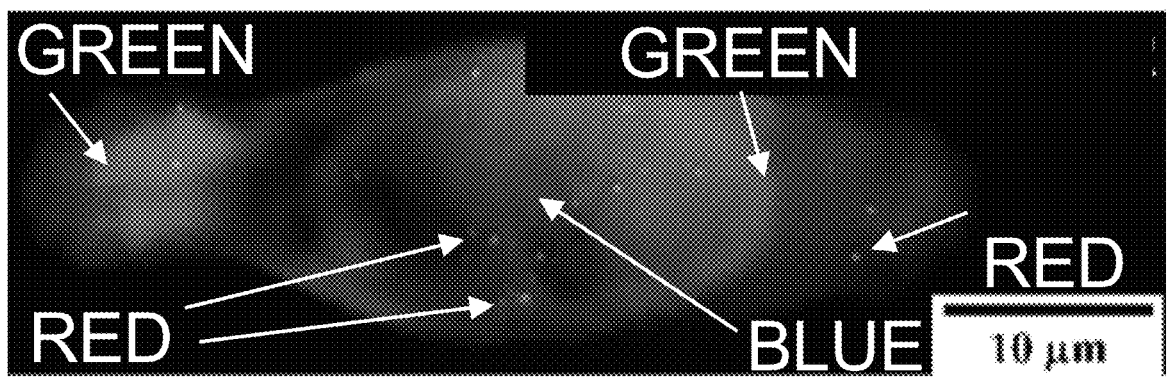
Figure 6C:
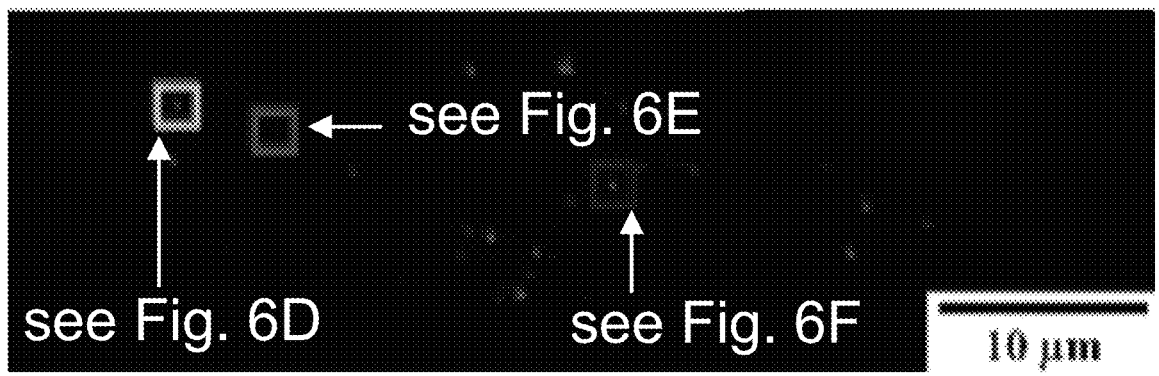
Figure 6D:
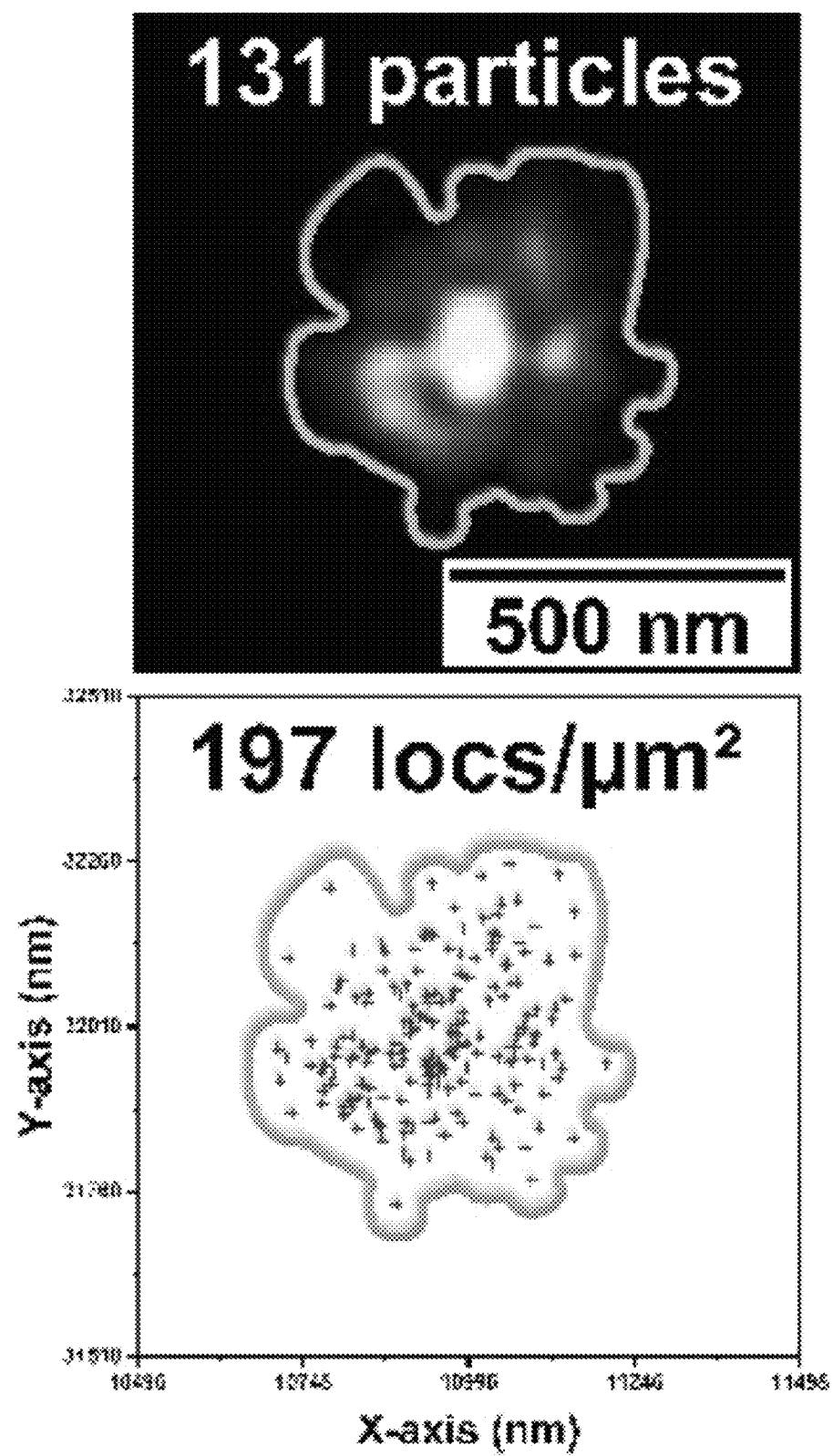
Figure 6E:
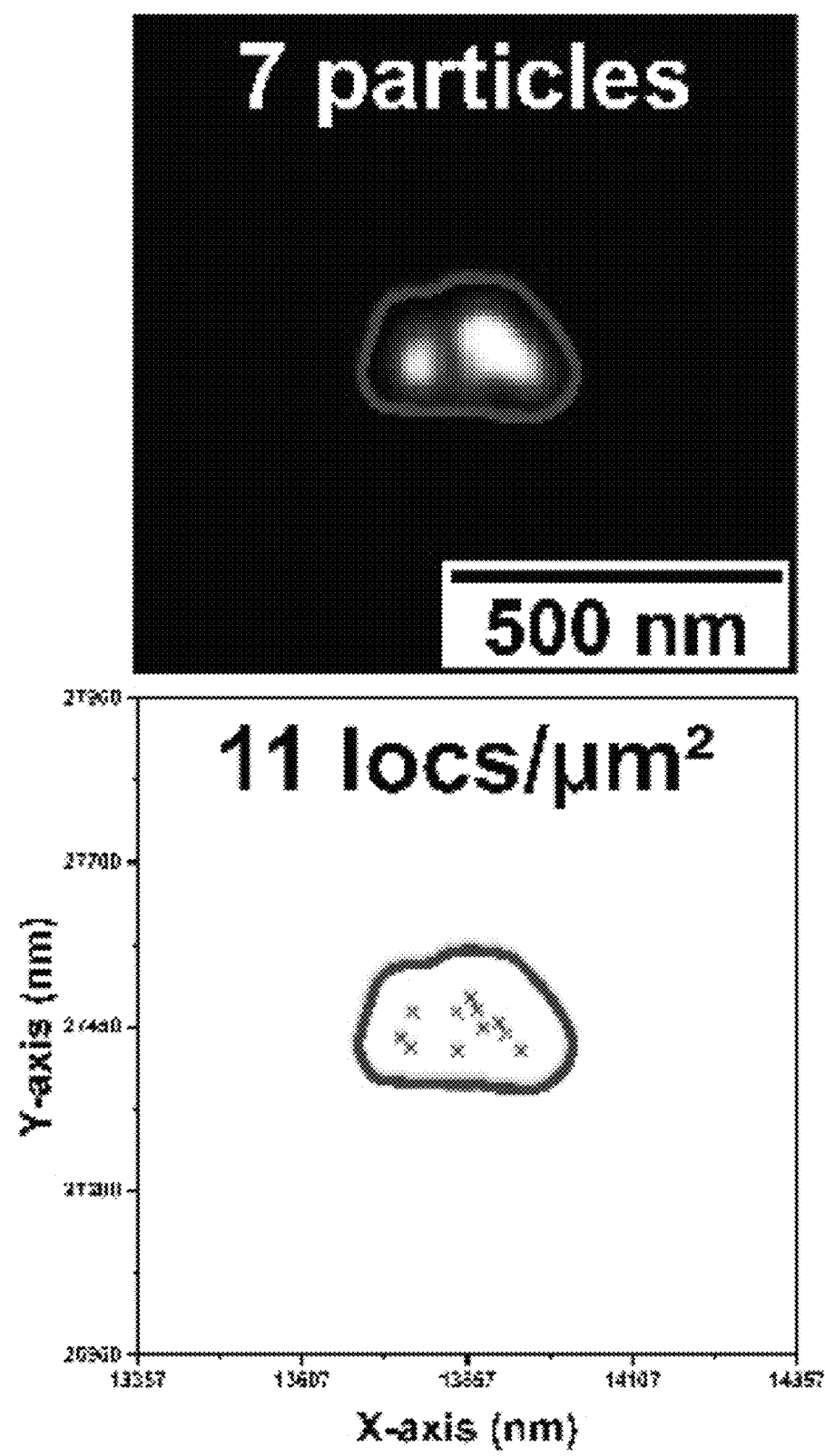
Figure 6F:
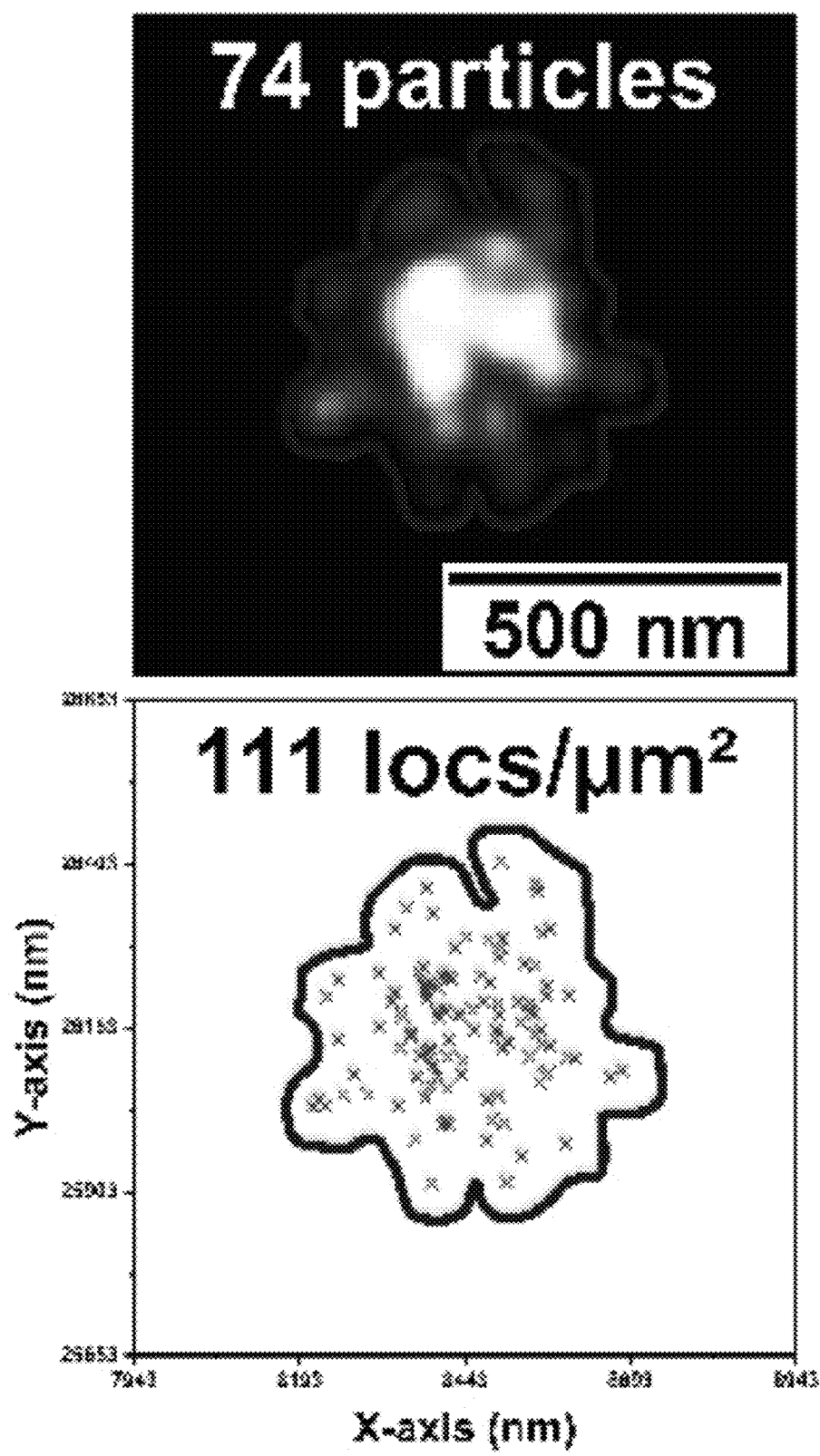
Figure 6G:
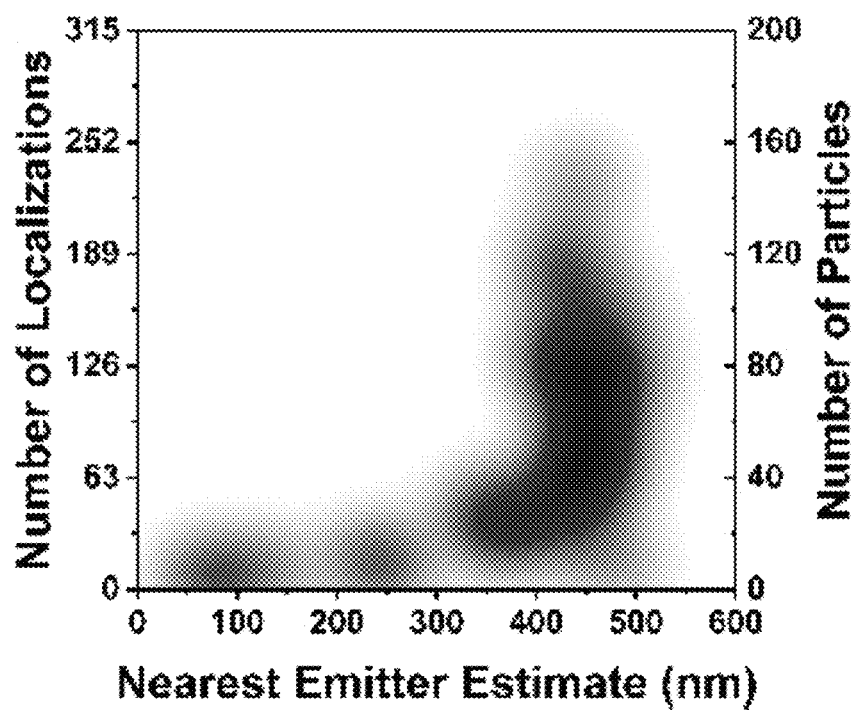
Figure 6H:
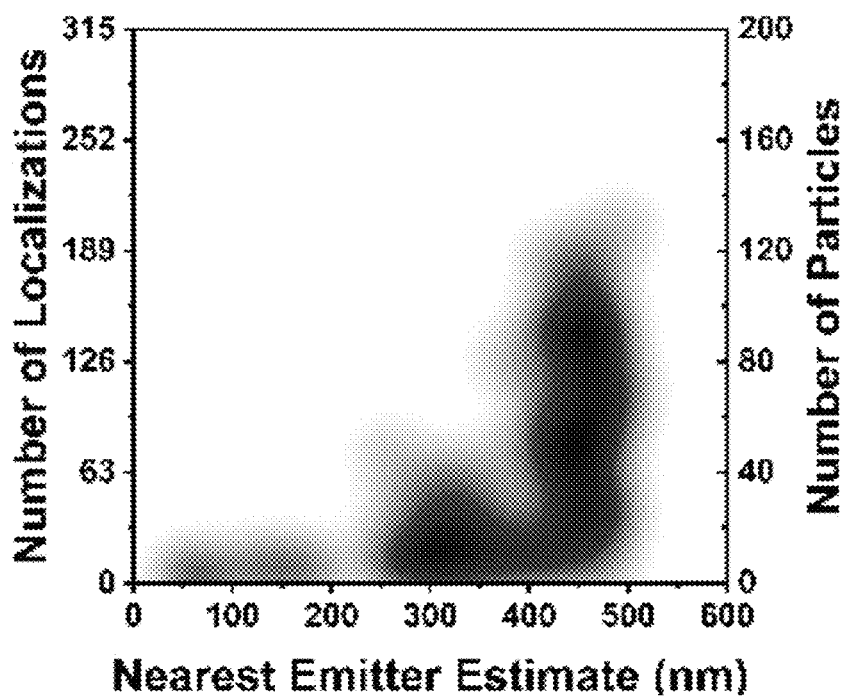
Figure 6I:
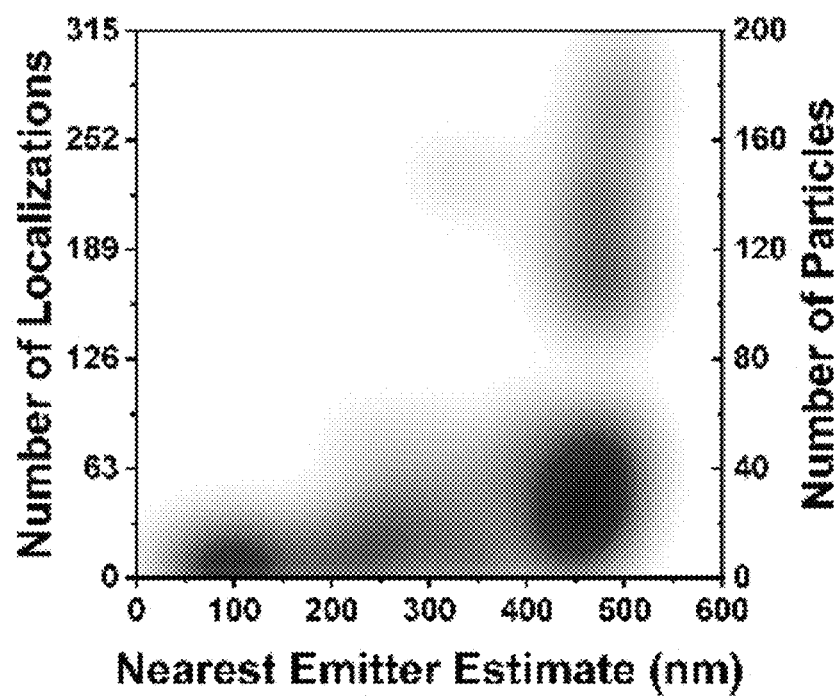
Figure 6J:
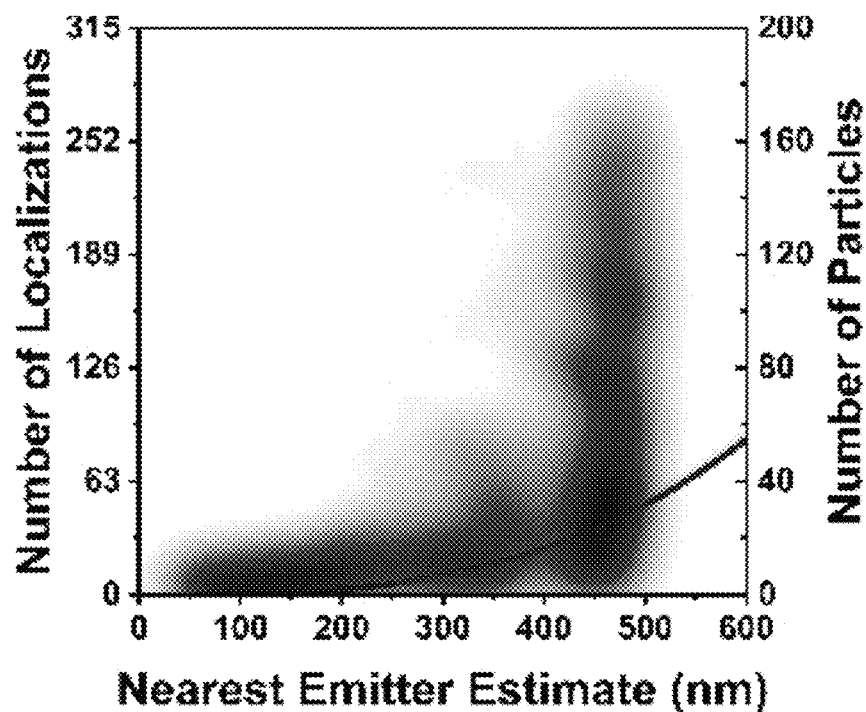

A major advantage of aC' dots over traditional STORM fluorophores is the fact that from numerous in-vivo studies with conventional C' dots, including several human clinical trials with their respective preclinical toxicological investigations, they are expected to show no substantial toxicity. Consistent with that expectation, using a PrestoBlue cell viability assay, there were no significant changes in HeLa and MDA-MB-231 triple negative breast cancer (TNBC) cell viability after exposure to 2 μM aC' dots for 24 hours (FIG. 21). This concentration is 40 times higher than that used for the fixed cell experiments, and 8 times higher than that used in live-cell imaging as shown in FIGS. 6A-6C. To obtain these live-cell images, MDA-MB-231 TNBC cells were starved for 24 hours in serum-free culture media to induce endocytosis of unfunctionalized PEG-Cy5-aC' dots (red) suspended in complete media. As controls, it was shown that 11 mM glutathione, the maximum concentration found in cells, had no effect on PEG-Cy5-aC' dot blinking, and that exposure to culture media for 48 hours does not cause any aggregation (FIG. 22). After 1-hour incubation, excess particles were washed away and the cells were labelled with Hoechst 33342 (blue) and a membrane stain, CellMask Orange (green). Imaging was performed in HBSS buffer with only one excitation (red) laser as described herein. The diffraction limited TIRF image (FIG. 6A) shows relatively heterogeneous and large red fluorescent blobs likely due to particles associated with intracellular vesicles. In contrast, when reconstructed using STORM (FIGS. 6B-6C), smaller more homogeneous red features appeared likely due to particles confined to intracellular vesicles. For 600 such features/vesicles from 13 individual cells, the vesicle size and number of particles per vesicle (estimated from the number of emitter localizations) were determined using an algorithm estimating the maximum emitter distance as described herein. Results for three example vesicles are exhibited in FIGS. 6D-6F, while three example kernel density plots of the number of localizations, and number of particles derived therefrom, as a function of vesicle size derived from three example cells are shown in FIGS. 6G-6I. Identification of the smaller fluorescent features shown in the panels of FIGS. 6D-6F with aC' dots confined in vesicles seemed justified as corroborated by the extracted size information of these features as well as the known mechanisms for particle uptake in living cells. The kernel density plots in FIGS. 6G-6I for individual cells 1-3 suggest well-defined size regimes for these vesicles with particle numbers going up substantially for vesicle sizes of 400-500 nm. This observation is corroborated when the quantitated information from all 13 cells was combined in FIG. 6J. Labelled vesicles ranged from ~50-500 nm in diameter, similar to intracellular vesicle sizes previously reported. Overall, in the low particle number range, as vesicle size increased, the number of localizations and number of particles derived therefrom in each vesicle roughly increased in a cubic fashion, as suggested by comparison with a cubic fit (fit curve) in FIG. 6J. The largest structures/vesicles observed were around 400-500 nm in size. For these largest vesicles, the number of localizations and particles per vesicle sharply increased, well beyond expectations from simple volume arguments (see deviation from fit). These vesicles could be maturing towards a degradation pathway as opposed to a recycling pathway. While the exact analysis of the biology of particle processing in MDA-MB-231 cells, e.g., via colocalization with known markers for different types of vesicles, is beyond the scope of this paper, these proof-of-principle experiments clearly demonstrate that aC' dots with characteristics enabling clinical translation (e.g., ultrasmall size, neutral PEG surface coating, etc.) constitute a powerful optical SRM particle platform for quantitative assessment of cellular structures and processes via live-cell imaging. While very recent studies have observed the size evolution of vesicles at super-resolution, those experiments were performed with fixed cells rather than live cells.

tion. This is particularly noteworthy as the C' dot particle platform encapsulating Cy5 or Cy5.5 has already been clinically translated in multiple human clinical trials (e.g., see clinicaltrials.gov identifiers: NCT01266096, NCT02106598, and NCT04167969). Optical SRM with aC' dots will therefore enable the direct study, in particular, of intracellular particle processing details in live cells relevant to questions associated with the clinical translation of diagnostic as well as therapeutic C' dot applications.

aC' dot synthesis: Cy5-maleimide (0.347 μmol) (Cy5(+), Lumiprobe) was reacted with 8.51 μmol of MPTMS (Sigma) overnight. Additionally, 100 μL of ASB (Sigma) was diluted to 1 mL in isopropanol. Then, 78 μL of TMOS (Sigma), the conjugated Cy5-silane, and 200 μL of the diluted ASB were rapidly added to 10 mL of 20 mM HCl with vigorous stirring at room temperature. The standard TMOS:ASB mol ratio was 87:13. Other ratios used for controls were 93.5:6.5 and 80.5:19.5. After 15 minutes of stirring, 150 μL of PEG-silane (Gelest) was added dropwise. After 5 minutes of stirring, 280 μL of 14% ammonium hydroxide was added and stirred for 12 hrs (hr(s)=hour(s)). Particle solutions were then heated at 80° C. for 12 hrs in an oil bath with no stirring. For aC' dots with Cy7 (Lumiprobe), ATTO647N (ATTO-TEC), sulfo-Cy5 (Cy5(−), Lumiprobe), Cy5.5 (Lumiprobe), Alexa Fluor 647 $C_2$ (Invitrogen), Cy3 (Lumiprobe), and Fluorescein-5 (F-5; Thermo Scientific) the same mol of dye-maleimide underwent the same synthesis protocol as stated above. 255 nmol DEAC, SE (Santa Cruz Biotechnology) was reacted with 6.4 μmol APTES overnight for aC' dots containing DEAC. PEG-Cy5-aC' dots all use Cy5(+) dye, not sulfo-Cy5 (i.e., Cy5(−)), unless specifically denoted.

TABLE 3

| Dye | DEAC | F-5 | Cy3 | Cy5 | sulfo-Cy5 | ATTO647N | Alexa Fluor 647 | Cy5.5 | Cy7 |
| --- | --- | --- | --- | --- | --- | --- | --- | --- | --- |
| Net Charge | 0 | 0 | +1 | +1 | −1 | +1 | −3 | +1 | +1 |

An ultrasmall, bright, and photostable PEGylated fluorescent core-shell aluminosilicate nanoparticle (aC' dot) platform for optical super-resolution microscopy, particularly STORM, in both fixed and live-cell specimens is described. When suspended in simple buffers, such as HBSS or PBS, and exposed to only one excitation light source, aC' dots exhibit fluorescence blinking likely due to a redox mechanism with duty cycles suitable for STORM. With their sub-10 nm diameter, ability to substantially enhance the per dye fluorescence brightness and photostability over free parent dye, the localization precision using aC' dots is high, and dyes not typically suitable for STORM can be converted into viable SRM probes. aC' dot properties reliably address current issues of STORM imaging, which conventionally requires specific fluorophores, cytotoxic imaging media, and multiple lasers. The highly tunable surface of aC' dots enables functionalization, e.g., with antibodies for enhanced targeting capabilities, as demonstrated in fixed cells. Finally, aC' dots are non-toxic to HeLa and MDA-MB-231 cells and can be used for live-cell optical super-resolution microscopy studies as exemplified here for nanoparticle trafficking in TNBC cells. Overall, aC' dots offer opportunities for long-term, multi-color STORM imaging in live cells without the need for expensive and technically demanding instrumental setups and chemically damaging imaging conditions, promising quantitative analysis, e.g., of cellular structures and processes in live cells with sub-diffraction limited resolu- C' dot Synthesis: The same dye conjugation as described above was used. 78 μL of TMOS and the conjugated dye were added dropwise to 10 mL 0.02 M aqueous ammonium hydroxide under vigorous stirring. 24 hrs later, 100 μL PEG-silane was added and stirred for an additional 24 hrs. Particle solutions were then heated without stirring in an oil bath at 80° C. for 24 hrs.

Particle Purification: After heating, particle solutions were dialyzed with 2 L of Milli-Q 18.2 MS/H$_2$O with 3 exchanges. Particle solutions were then syringe filtered across a 0.22 μm PVDF filter (Foxx Life Sciences) and subsequently upconcentrated in a 30 kDa spin filter (Corning) at 24,000×g. Particles were size purified using GPC (Bio-Rad) with 0.9% NaCl (Santa Cruz Biotechnology) running solvent. The fractions that eluted within the FWHM of the resulting chromatogram were collected and resuspended in 18.2 MΩ H$_2$O.

Particle Characterization: Particles or unfunctionalized dye-maleimide were diluted in 3 mL of water in a quartz cuvette and the absorbance spectra were obtained using a Cary 5000 spectrofluorometer. Particle and dye solutions were absorbance matched in the same cuvette by altering their concentrations, and their emission spectra were obtained using a Photon Technologies International Quantamaster fluorometer. Brightness enhancement calculated by dividing the peak fluorescence of the particles by that of the unfunctionalized dye from absorption matched solutions.

Brightness enhancement errors in Table 1 are derived from the standard deviation of three separate measurements.

Hydrodynamic diameter, concentration, and dyes per particle were obtained using fluorescence correlation spectroscopy (FCS) data in combination with absorption measurement data. For FCS, solid-state 445 nm, 488 nm, 633 nm, and 785 nm lasers and a HeNe 543 nm laser were used for particles containing dyes that could be excited by these respective lasers. Reference dyes used were ATTO 425 (ATTO-TEC), ATTO 488 (ATTO-TEC), TMR, Alexa Fluor 647 (Life Technologies), and Cy7. Diluted particles or reference dyes were added to 1.5 coverslip glass dishes (MatTek) and placed onto an inverted water immersion objective (Zeiss Plan-Neofluar 63×NA 1.2). Fluorescence was filtered through a 50 μm pinhole and collected by an avalanche photodiode detector (SPCM-AQR-14, PerkinElmer). Autocorrelation curves were obtained for fifteen 30-second collections from a hardware collector card (Flex03LQ, Correlator.com) and were fit with the correlation function, Equation (1), as well as Equations (2-3), that accounts for cis-trans photoisomerization:

$$G(\tau) = 1 + \frac{1}{N} \cdot \left(1 + \frac{\tau}{\tau_D}\right)^{-1} \cdot \left(1 + \frac{\tau}{\kappa^2 \tau_D}\right)^{-\frac{1}{2}} \cdot \frac{1}{1-T} \cdot \left(1 - T + T \cdot e^{-\frac{\tau}{\tau_F}}\right) \quad (1)$$

$$\kappa = \frac{\omega_z}{\omega_{xy}} \quad (2)$$

$$\tau_D = \frac{\omega_{xy}}{4D} \quad (3)$$

N is the average number of particles in the observation volume, which is defined by its structure factor, κ, the ratio of its axial ($\omega_z$) and radial radii ($\omega_{xy}$). D is the diffusion coefficient, T is the fraction of cis isomers, and $\tau_F$ is the photoisomerization relaxation time. Particle hydrodynamic diameter was calculated using the Stokes-Einstein equation, Equation (4):

$$d = 2 \frac{k_b T}{6\pi \eta D} \quad (4)$$

Here, $k_b$ is the Boltzmann constant, T is temperature, and η is the dynamic viscosity. Average dyes/particle or dyes/conjugate are determined using Equation (5):

$$n = \frac{C_{dye}}{C_{particle/conjugate}} \quad (5)$$

From the measured absorbance and using the extinction coefficient of the fluorophore the concentration, $C_{dye}$, could be determined. The particle or conjugate concentration, $C_{particle/conjugate}$, was calculated from FCS experimental results.

TEM images were obtained from a FEI Tecnai T12 Spirit microscope at 120 kV. Energy-dispersive X-ray spectroscopy (EDS) measurements were carried out on a TESCAN MIRA3 field-emission scanning electron microscope equipped with a Bruker XFlash6160 silicon drift detector. Concentrated particle solution was drop-casted on a silicon wafer and dried at 30° C. for 2 days. The final dry particle layers were about 500 μm thick. EDS spectra were collected at 10 kV accelerating voltage. Zeta potential measurements were collected on a Malvern Zetasizer Nano-SZ. The average and standard deviation were calculated from three separate measurements.

Determination of Photostability from Photobleaching Experiments: Photobleaching experiments were performed based on previously published methods. PEG-aC' dots containing various dyes or the free forms of those dyes were suspended in 18.2 MΩ $H_2O$ to a volume of 100 μL in a 100 μL quartz cuvette (Starna) at an optical density ~0.6 at their respective maximum absorbance wavelengths. 405 nm (DEAC), 488 nm (F-5), 561 nm (Cy3), or 640 nm (Cy5, ATTO647N, Alexa Fluor 647, Cy5.5, and Cy7) lasers (Opto Engine LLC) were expanded and collimated to cover the entire cuvette viewing window at ~40 mW/cm². Samples were exposed to the laser for 0 s, 10 s, 20 s, 30 s, 60 s, 120 s, 240 s, 480 s, 900 s, 1800 s, and 3600 s followed by obtaining the absorbance spectra using a Cary 5000 spectrofluorometer. Maximum absorbance of the dye peak y(t) was plotted versus exposure time (t) and fit to a single exponential function, Equation 6:

$$y(t) = y_0 + A_1 e^{-\frac{x(t)}{t_1}} \quad (6)$$

The photobleaching time scale for a sample is given by its characteristic $t_1$ value. Photostability enhancements were calculated using Equation 7:

$$\text{Photostability Enhancement} = \frac{t_{1,aC'dot}}{t_{1,free\,dye}} \quad (7)$$

The error of stability enhancement measurements presented in Table 1 is the cumulative error of the $t_{1,aC'dot}$ and $t_{1,free\,dye}$ fit standard errors. This was calculated using propagation of error analysis (Equation 8):

$$\text{Error} = \frac{t_{1,aC'dot}}{t_{1,free\,dye}} \sqrt{\left(\frac{SE_{t_{1,aC'dot}}}{t_{1,aC'dot}}\right)^2 + \left(\frac{SE_{t_{1,free\,dye}}}{t_{1,free\,dye}}\right)^2} \quad (8)$$

Particle Biotinylation and Immobilization: Roughly 45 nmol of purified particles were vigorously stirred with 5.73 μmol (3-aminopropyl) trimethoxysilane (APTMS; Sigma) overnight followed by addition of 500 nmol biotin-PEG-NHS ester (Quanta Biodesign) overnight. Biotinylated particles were purified as described above.

MatTek dishes were etched with 1:1 0.5 N HCl:MeOH for 30 min followed by washing with ethanol 3 times. Next, they were exposed to 0.2 M MPTMS for 30 min and washed with $H_2O$ 3 times followed by exposure to 4 mM N-γ-maleimidobutyryl-oxysuccinimide ester (Thermo Scientific) for 30 min and another set of washing. Finally, they were exposed to 0.05 mg/mL streptavidin (Thermo Scientific) overnight at 4° C., washed 3 times with PBS (Quality Biologic), and stored in PBS. Biotinylated particles or dye were interacted with streptavidin dishes for 1 minute followed by washing wish PBS 3 times.

Imaging Setup: All imaging was performed using a 100× oil-immersion TIRF objective with a 405 nm, 488 nm, 561 nm, or 640 nm excitation laser (Opto Engine LLC) depending on the fluorophore. Cell images and fluorescence time traces, except those for high time resolution collections, were acquired using an Andor iXon Life 897 EMCCD camera at 50 ms integration times for 10,000 frames. Integration time is defined as the sum of the exposure time and the readout time, where exposure time is the time the sample is exposed to the light source during the acquisition of a single image and readout time is the length of time required for the camera to read the acquired image. STORM reconstruction of cell images were performed using the ImageJ ThunderSTORM plugin, as described earlier, with localizations with >10 nm uncertainty removed.

Single Particle Fluorescence Time Trace Collection: For trace collection, particle-immobilized dishes were exposed to various combinations of an excitation laser, 405 nm laser, 0.14 M β-mercaptoethanol (Sigma), and an oxygen scavenging system containing 5% w/v glucose (Sigma), 0.5 mg/mL glucose oxidase (Sigma), and 0.04 mg/mL oxygen catalase (Roche Applied Science) in HBSS (Gibco). A custom designed Matlab protocol described in a previous publication was used to analyze photon statistics. Briefly, a maximum intensity projection was performed to locate the initial pixel coordinates using the maximum-likelihood estimation (MLE). A 7×7 pixel region was then formed around the center of the of the positions. To increase speed of analysis, the 2-dimensional Gaussian integration was replaced with the trapezoidal numerical integration method.

Imaging FCS: For Imaging FCS experiments, PEG-Cy5-C' dots, and PEG-Cy5-aC' dots were immobilized on a streptavidin-coated MatTek dishes for 5 minutes at room temperature in HBSS buffer without or with Trolox (2 mM). The measurements were performed with a home-built instrument described elsewhere with a 642-nm diode-pumped solid-state laser (Coherent, Santa Clara, Calif.) and the emission beam was passed through an emission filter (ET655LP, Chroma) before being collected by an EMCCD camera (Andor iXon 897; Andor, Belfast, United Kingdom). A small region of interest (10×10 pixels) on the EMCCD camera were chosen around a single immobilized particle. An EM gain of 1000 was used for all measurements. The raw fluorescence intensity trace was collected with 0.9 ms integration time. The raw autocorrelation function (ACF), $G(\tau)$, a function of lag time ($\tau$) was of the intensity trace was generated using the Imaging FCS 1.491 plug-in (www.dbs.nus.edu.sg/lab/BFL/imfcs_image_j_plugin.html). The raw ACF was fitted with an exponential function as follows, Equation 9:

$$G(\tau) = A \exp\left(-\frac{\tau}{\tau_{off}}\right) \quad (9)$$

where $\tau_{off}$ is the characteristic off-time described in the main text.

Nanoparticle-antibody Conjugation: Roughly 45 nmol of purified particles were vigorously stirred with 5.73 μmol APTMS overnight followed by GPC purification, collecting the FWHM. The remaining roughly 25 nmol of aminated particles were vigorously stirred with 2.5 μmol DBCO-PEG$_4$-NHS ester (Click Chemistry Tools) followed by GPC purification, collecting the entire particle peak. Polyclonal goat-anti-mouse unconjugated secondary antibodies (31182, Invitrogen) were conjugated with azido-PEG$_{12}$-NHS ester (1:20 Ab:NHS mol ratio; Quanta Biodesign) for 2 hrs at room temperature. Next, the Ab-azide was reacted with DBCO-particles (20:1 Ab:NP mol ratio) overnight at room temperature. Excess m-dPEG$_4$-amine (Quanta Biodesign) was added to block unreacted NHS ester from the azido-PEG$_{12}$-NHS ester. The secondary Ab-particle conjugates were purified via GPC as described previously. Nanoparticle-antibody conjugates were characterized using a UV-Vis and FCS as described above. Secondary Ab-particle conjugates were reacted with excess primary antibodies for 30 mins at room temperature before measurements.

Cell Culture: HeLa and MDA-MB-231 cells (ATCC) were cultured in phenol red free RPMI-1640 (Gibco) supplemented with 10% fetal bovine serum (FBS; Corning) and 10,000/10,000 penicillin/streptomycin (Lonza) at 37° C., 5% $CO_2$, and 90% humidity. Cells were detached with trypsin/EDTA (Gibco) and approximately $1\times10^5$ cells were plated in a 1.5 tissue culture treated polymer coverslip imaging dish (Ibidi) and incubated overnight for further processing and labelling for imaging.

Cell Viability Assay: 100 μL of $5\times10^4$ HeLa or MDA-MB-231 cells in complete media were plated in a 96 well plate and allowed to adhere overnight. PEG-Cy5-aC' dots were diluted to 2 μM in complete media and added to replace the existing media. After 24 hr incubation, wells were washed 3 times with PBS. 10% PrestoBlue Reagent (Invitrogen) was added to blank, control, and sample wells and incubated for 2 hrs. Fluorescence with 560/590 ex/em was measured with a SpectraMax M2. Results were normalized to the control samples with no particle exposure.

Hela Cell Fixation, Permeabilization, Tubulin Labeling, and Image Acquisition: Hela cells were fixed with 4% paraformaldehyde for 10 minutes at room temperature and washed 3 times with PBS. Next, they were permeabilized for 10 minutes at room temperature with 0.1% NP-40 (RPI) followed by 3 PBS washes. Cells were then blocked with 10% goat serum (Gibco) for 1 hour and then incubated for another with 1:200 mouse-anti-tubulin primary antibodies (3873S, Cell Signaling Technology) in 10% goat serum and then washed. Finally, the cells were incubated with ~50 nM PEG-ATTO647-aC' dot-secondary antibody conjugates in 10% goat serum overnight at 4° C. followed by 3 washing steps. Prior to imaging, cells were incubated with 1:1000 Hoechst 33342 (Invitrogen) for 5 mins followed by washing. Images were acquired in PBS with a 640 nm excitation laser.

MDA-MB-231, Intracellular Vesicle Labeling, and Image Acquisition: Plated MDA-MB-231 cells were starved for 24 hrs in the same media described above, but without FBS to induce endocytosis. Incomplete media was replaced with complete media containing 250 nM of PEG-Cy5-aC' dots and incubated for 1 hour before washing with HBSS three times. Cells were labeled with Hoechst 33342 as described above as well as 1:1000 CellMask Orange (Invitrogen) in HBSS immediately before imaging. Images were acquired in HBSS with a 640 nm excitation laser.

Vesicle Size and Number of Particle determination: Vesicle size was determined by averaging all localizations on the edge of the object. To remove localizations within the object, which would make the average object side smaller, the following protocol was followed:
1) Determine the maximum emitter-emitter distance for each emitter and store the largest maximum in memory.
2) Remove emitters whose maximum distance is less than 80% of the largest maximum distance.
3) Average the remaining maximum distance for the remaining emitters to get the vesicle diameter.

Number of particles were estimated by dividing the total number localizations in that region by the average number of times a single particle will "blink" within a certain time window. This value was determined by attaching single nanoparticles to streptavidin coated class surfaces then average over several different particles.

Internal Aluminum Concentration Estimation: Assuming a spherical aluminosilicate core with a diameter of 3 nm, its volume would be $1.41 \times 10^{-20}$ cm$^3$. While aC' dots were synthesized with a ratio of 87:13 silane:ASB mol:mol, the intensity ratio of Si to Al from EDS experiments suggested (see FIG. 7B) that the core is comprised of 92% SiO$_2$ and 8% AlO$_2$ units (because both Si and Al are 4-fold coordinated). 8% aluminosilicate glasses have a density of ~2.3 g/cm$^3$. Because both AlO2 and SiO$_2$ have a molar mass ~60 g/mol, Equation S10, S11, and S12 can be combined into Equation S13:

$$\#SiO_2 + \#AlO_2 = \frac{\rho \times V \times N_A}{MW} \quad (10)$$

$$[Al] = \frac{\#AlO_2}{V \times N_A} \quad (11)$$

$$0.08 = \frac{\#AlO_2}{\#SiO_2 + \#AlO_2} \quad (12)$$

$$[Al] = 0.08 \times \frac{\rho}{MW} \quad (13)$$

Where $\rho$ is the core density, V is the core volume, $N_A$ is Avogadro's Number, and MW is the molar mass of SiO$_2$ and AlO$_2$ units. Using Equation 13, the resulting aluminum concentration is found to be ~3M. As a demonstration of the high local concentration of aluminum in aC' dots, even if there is only 1 AlO$_2$ unit in a 3 nm particle core, its concentration would be ~100 mM using Equation 11. These concentrations are much higher than the maximum of 1 mM reducing agent described in the literature.

Although the present disclosure has been described with respect to one or more particular example(s), it will be understood that other examples of the present disclosure may be made without departing from the scope of the present disclosure.

The invention claimed is:

1. A method of obtaining an optical super-resolution image of a sample or a portion thereof or an individual or a portion thereof comprising:
   contacting the sample or a portion thereof or individual or a portion thereof with one or more aluminosilicate nanoparticle(s), each individual aluminosilicate nanoparticle comprising at least one fluorophore molecule or group derived from a fluorophore molecule covalently bonded to the aluminosilicate network of the individual aluminosilicate nanoparticle, wherein the fluorophore molecule(s) or group(s) are encapsulated by the aluminosilicate network, wherein the aluminosilicate nanoparticle(s) do(es) not comprise sulfur or a metal other than aluminum, or a composition comprising the one or more of the aluminosilicate nanoparticle(s), wherein the composition does not comprise sulfur or a metal other than aluminum;
   irradiating the sample or a portion thereof or the individual or a portion thereof with excitation electromagnetic radiation, thereby exciting at least one of the fluorophore molecules of an individual aluminosilicate nanoparticle; and
   obtaining a fluorescence image or a sequence of fluorescence images which can be processed to obtain a super-resolution image of the sample or portion thereof or the individual or a portion thereof.

2. The method of claim 1, wherein the obtaining the fluorescence image or a sequence of fluorescence images comprises:
   detecting electromagnetic radiation, the detected electromagnetic radiation from each individual aluminosilicate particle having been emitted by the at least one excited fluorophore molecule of the individual aluminosilicate particle as a result of excitation by the excitation electromagnetic radiation; and
   processing signals corresponding to the detected electromagnetic radiation to provide one or more fluorescence images of the sample or portion thereof or the individual or a portion thereof.

3. The method of claim 1, wherein at least a portion of the optical super-resolution image exhibits sub-diffraction limit resolution.

4. The method of claim 1, wherein the method is an optical super-resolution microcopy method including, but not limited to, ground state depletion (GSD) microscopy, stochastic optical reconstruction microscopy (STORM), direct stochastic optical reconstruction microscopy (dSTORM), stimulated emission and depletion (STED), or photoactivated localization microscopy (PALM).

5. The method of claim 1, wherein the contacting is administering the composition to the individual or a portion of the individual.

6. The method of claim 5, wherein the electromagnetic radiation is directed into the individual or a portion of the individual.

7. The method of claim 6, wherein the electromagnetic radiation is directed into a region, wherein the region is within the individual or a portion of the individual.

8. The method of claim 1, wherein the electromagnetic radiation comprises one or more wavelength(s) from 400 to 1200 nm.

9. The method of claim 1, wherein the irradiation is carried out using a single laser.

10. The method of claim 1, wherein the electromagnetic radiation is a single wavelength.

11. The method of claim 1, wherein the fluorophore(s) is/are a fluorescent dye or a fluorescent protein.

12. The method of claim 11, wherein the fluorescent dye is chosen from cyanine dyes, rhodamine dyes, coumarin dyes, boron-dipyrromethene (BODIPY) dyes, xanthene dyes, eosin dyes, carbopyronine dyes, methylene blue, fluorescein, Acridine Orange, and a group/groups derived therefrom, and any combination thereof.

13. The method of claim 1, wherein the aluminosilicate nanoparticle(s) individually have at least one dimension of 1 to 30 nm.

14. The method of claim 1, wherein the sample comprises living or fixed tissues and/or cells.

15. The method of claim 1, wherein the sample is a biopsy obtained from an individual.

16. The method of claim 1, wherein the individual is suspected of having cancer or has been diagnosed with cancer.

17. The method of claim 1, wherein the aluminosilicate nanoparticle or at least a portion of the aluminosilicate nanoparticles comprises one or more targeting ligand(s).

18. The method of claim 17, wherein the sample comprises at least one targeting moiety that is complementary to the targeting ligand(s).

* * * * *